United States Patent
Blackwell et al.

(10) Patent No.: US 11,247,976 B2
(45) Date of Patent: Feb. 15, 2022

(54) SYNTHETIC LIGANDS THAT MODULATE THE ACTIVITY OF THE RHLR QUORUM SENSING RECEPTOR

(71) Applicant: Wisconsin Alumni Research Foundation, Madison, WI (US)

(72) Inventors: Helen Blackwell, Middleton, WI (US); Michelle E. Boursier, Madison, WI (US); Joseph D. Moore, Wayne, PA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/097,541

(22) PCT Filed: Apr. 30, 2017

(86) PCT No.: PCT/US2017/030314
§ 371 (c)(1),
(2) Date: Oct. 29, 2018

(87) PCT Pub. No.: WO2017/190116
PCT Pub. Date: Nov. 2, 2017

(65) Prior Publication Data
US 2019/0144407 A1 May 16, 2019

Related U.S. Application Data

(60) Provisional application No. 62/376,291, filed on Aug. 17, 2016, provisional application No. 62/329,942, filed on Apr. 29, 2016.

(51) Int. Cl.
| | | |
|---|---|---|
| *C07D 307/33* | (2006.01) | |
| *C07D 333/36* | (2006.01) | |
| *C07D 207/09* | (2006.01) | |
| *C07D 207/273* | (2006.01) | |
| *C07D 307/14* | (2006.01) | |
| *C07C 233/06* | (2006.01) | |
| *C07C 233/61* | (2006.01) | |
| *C07C 235/22* | (2006.01) | |
| *C07C 201/00* | (2006.01) | |
| *C07D 307/22* | (2006.01) | |
| *C07C 233/58* | (2006.01) | |
| *C07C 233/60* | (2006.01) | |
| *C07C 233/32* | (2006.01) | |

(52) U.S. Cl.
CPC .......... *C07D 307/33* (2013.01); *C07C 201/00* (2013.01); *C07C 233/06* (2013.01); *C07C 233/32* (2013.01); *C07C 233/58* (2013.01); *C07C 233/60* (2013.01); *C07C 233/61* (2013.01); *C07C 235/22* (2013.01); *C07D 207/09* (2013.01); *C07D 207/273* (2013.01); *C07D 307/14* (2013.01); *C07D 307/22* (2013.01); *C07D 333/36* (2013.01); *C07C 2601/04* (2017.05); *C07C 2601/08* (2017.05)

(58) Field of Classification Search
CPC .................................................... C07D 307/33
USPC ........................................................ 514/424
See application file for complete search history.

(56) References Cited

U.S. PATENT DOCUMENTS

| | | |
|---|---|---|
| 5,776,974 A | 7/1998 | Bycroft et al. |
| 7,642,285 B2 * | 1/2010 | Blackwell ............ C07D 307/33 514/471 |
| 7,737,164 B2 | 6/2010 | Blackwell et al. |
| 7,910,622 B2 | 3/2011 | Blackwell et al. |
| 8,227,616 B2 | 7/2012 | Blackwell et al. |
| 8,269,024 B2 | 9/2012 | Blackwell et al. |
| 8,350,061 B2 | 1/2013 | Iyer et al. |
| 8,367,680 B2 | 2/2013 | Blackwell et al. |
| 8,618,327 B2 | 12/2013 | Blackwell et al. |
| 8,624,063 B2 | 1/2014 | Blackwell et al. |
| 8,815,943 B2 | 8/2014 | Blackwell et al. |
| 9,758,472 B2 | 9/2017 | Blackwell et al. |
| 9,796,694 B2 | 10/2017 | Blackwell et al. |
| 10,322,122 B2 | 6/2019 | Blackwell et al. |

(Continued)

FOREIGN PATENT DOCUMENTS

| | | |
|---|---|---|
| WO | 1999/027786 | 6/1999 |
| WO | 2001/018231 | 3/2001 |
| WO | 2003/106445 | 12/2003 |

OTHER PUBLICATIONS

Geske et al. Bioorganic & Medicinal Chemistry Letters (2008),18(22), 5978-5981.*
Search Report and Written Opinion, dated Sep. 7, 2017, corresponding to International Application No. PCT/US2017/030314 (filed Apr. 30, 2017), parent of the present application, 11 pp.
Boursier et al. (May 2018) "A comparative study of non-native N-acyl l-homoserine lactone analogs in two Pseudomonas aeruginosa quorum sensing receptors that share a common native ligand yet inversely regulate virulence," ACS Chem. Biol. 13(9):2655-2662.

(Continued)

*Primary Examiner* — Kahsay Habte
(74) *Attorney, Agent, or Firm* — Leydig, Voit & Mayer, Ltd.

(57) ABSTRACT

RhlR modulators including agonist and antagonists which are useful for modulating QS phenotypes in Gram-negative bacteria. Certain compounds of general formula A-W-HG having various carbocyclic ad heterocyclic head groups (HG) and various tail groups (A), where —W— is —CO—NH—, —SO$_2$—NH—, —CO—NH—CH$_2$—, or —SO$_2$—NH—CH$_2$— are RhlR agonists or antagonists. The compounds are useful in methods of modulating quorum sensing in Gram-negative bacteria, particularly in *Pseudomonas*. Compositions including certain RhlR modulators are useful for decreasing the virulence of Gram-negative bacteria. Pharmaceutical compositions comprising certain RhlR modulators are useful for treatment of infections of Gram-negative bacteria.

18 Claims, 19 Drawing Sheets

(56) References Cited

U.S. PATENT DOCUMENTS

| | | |
|---|---|---|
| 10,807,943 B2 | 10/2020 | Blackwell et al. |
| 2003/0171421 A1 | 9/2003 | Davies et al. |
| 2004/0033549 A1 | 2/2004 | Greenberg et al. |
| 2017/0369462 A1 | 12/2017 | Blackwell et al. |
| 2020/0115356 A1 | 4/2020 | Blackwell et al. |

OTHER PUBLICATIONS

Chen et al. (Apr. 2011) "A strategy for antagonizing quorum sensing," Mol. Cell 42:199-209.

Eibergen et al. (2015) "Potent and Selective Modulation of the RhlR Quorum Sensing Receptor by Using Non-Native Ligands: An Emerging Target for Virulence Control in *Pseudomonas aeruginosa*," Chem BioChem 16:2348-2356.

Galloway et al. (2011) "Quorum sensing in Gram-negative bacteria: small-molecule modulation of AHL and AI-2 quorum sensing pathways," Chem. Rev., 111,28-67.

Gerdt & Blackwell (2014). Competition studies confirm two major barriers that can preclude the spread of resistance to quorum-sensing inhibitors in bacteria. ACS Chem. Biol., 9,469 2291-2299.

Geske et al. (2008) "Evaluation of a focused library of N-aryl L-homoserine lactones reveals a new set of potent quorum sensing modulators," Bioorg. Med. Chem. Lett., 18, 5978-5981(a).

Geske et al. (2008) "Comparative analyses of N-acylated homoserine lactones reveal unique structural features that dictate their ability to activate or inhibit quorum sensing," ChemBioChem 9, 389-400 (b).

Geske et al. (2007) "Modulation of bacterial quorum sensing with synthetic ligands: systematic evaluation of N-acylated homoserine lactones in multiple species and new insights into their mechanisms of action," J. Am. Chem. Soc., 129, 13613-13625.

Geske et al. (2005) "Small molecule inhibitors of bacterial quorum sensing and biofilm formation," J. Am. Chem. Soc. 127, 12762-12763.

Geske et al. (May 2007) "N-Phenylacetanoyi-L-Homoserine Lactones Can Strongly Antagonize or Superagonize Quorum Sensing in Vibrio fischeri," ACS Chem. Biol. 2(5):315-320.

Geske et al. (Jun. 2008) "Expanding Dialogues: From Natural Autoinducers To Non-Natural Analogues that Modulate Quorum Sensing In Gram-Negative Bacteria" Chem. Soc. Rev. 37:1432-1447.

Hodgkinson et al. (2012). Design, synthesis and biological evaluation of non-natural modulators of quorum sensing in Pseudomonas aeruginosa. Org. Biomol. Chem., 10, 6032-6044.

Ikeda et al. (2001) "The Synthesis of Optically Pure Enantiomers of N-Acyl-Homoserine Lactone Autoinducers and Their Analogues," Chem. Lett. 30(4):314-315.

Ishida et al. (2007) "Inhibition of Quorum Sensing in Pseudomonas aeruginosa by N-Acyl Cyclopentylamides," Appl. Environ. Microbiol. 73, 3183-3188.

Jog et al. (Feb. 2006) "Stereoisomers of *P. aeruginosa* Autoinducer Analog to probe the Regulator Binding Site," *Chem. Biol.* 13:123-128.

Mattmann et al. (2011) "Potent and Selective Synthetic Modulators of a Quorum Sensing Repressor in Pseudomonas aeruginosa Identified from Second-Generation Libraries of N-Acylated L-Homoserine Lactones" ChemBioChem 12:942-949.

Mattmann et al. (2008). Synthetic ligands that activate and inhibit a quorum-sensing regulator in Pseudomonas aeruginosa. Bioorg. Med. Chem. Lett. 18, 3072-075.

McInnis et al. (2011) "Thiolactone Modulators of Quorum Sensing Revealed Through Library Design and Screening" Bioorg. Med. Chem. 19:4820-4828.

McInnis et al. (2011) "Design, synthesis, and biological evaluation of abiotic, nonlactone modulators of LuxR-type quorum sensing," Biorgan. Med. Chem. 19, 4812-4819.

Moore et al. (2015). A comparative analysis of synthetic quorum sensing modulators in Pseudomonas aeruginosa: New insights into mechanism, active efflux susceptibility, phenotypic response, and next-generation ligand design. J. Am. Chem. Soc., 137(46), 14626-14639.

Moore et al. (2014) Active efflux influences the potency of quorum sensing inhibitors in Pseudomonas aeruginosa. ChemBioChem 15, 435-442.

Morkunas et al. (2012). Inhibition of the production of the Pseudomonas aeruginosa virulence factor pyocyanin in wild-type cells by quorum sensing autoinducer-mimics. Org. Biomol., 42, 8452-8464.

O'Loughlin et al. (2013). A quorum-sensing inhibitor blocks Pseudomonas aeruginosa virulence and biofilm formation. Proc. Natl. Acad. Sci. U. S. A., 110, 17981-17986.

Reverchon et al. (2002) New synthetic analogues of N-acyl homoserine lactones as agonists or antagonists of transcriptional regulators involved in bacterial quorum sensing. Bioorg. Med. Chem. Lett. 12, 1153-1157.

Welsh et al. (2015) Small molecule disruption of quorum sensing cross-regulation in Pseudomonas aeruginosa causes major and unexpected alterations to virulence phenotypes. J. Am. Chem. Soc., 137, 1510-1519.

\* cited by examiner

SYNTHETIC LIGANDS THAT MODULATE THE ACTIVITY OF THE RHLR QUORUM SENSING RECEPTOR

CROSS-REFERENCE TO RELATED APPLICATIONS

This application is a U.S. National Stage Application under 35 U.S.C. § 371 of International Application No. PCT/US2017/030314, filed Apr. 30, 2017, which claims the benefit of U.S. provisional applications 62/329,942, filed Apr. 29, 2016, and U.S. provisional application 62/376,291, filed Aug. 17, 2016. Each of these applications is hereby incorporated by reference in its entirety.

STATEMENT REGARDING GOVERNMENT FUNDING

This disclosure was made with government support under GM 109403 awarded by the National Institutes of Health. The government has certain rights in the invention.

BACKGROUND

Many bacterial species are capable of coordinating population density with genome expression using an intercellular signaling process known as quorum sensing (QS). Generally, QS bacteria use small-molecule signals to synchronize the display of group-beneficial phenotypes only at high populations.[1, 2] In Gram-negative bacteria, this cell-cell communication mechanism is commonly mediated by N-acylated homoserine lactones (AHLs), which are constitutively synthesized by LuxI-type synthases.[3] These small molecules freely diffuse across the cell membrane (though in select cases, export is facilitated by efflux pumps),[4] and as population density increases, the AHLs reach a concentration at which they productively bind LuxR-type receptors. The ligand-activated QS receptors then serve as transcriptional factors capable of activating gene expression. Pathogenic bacteria use QS throughout the process of infecting host organisms: at early stages of infection, the pathogen produces few virulence factors in order to evade the immune response of a host, and only at sufficiently high populations do the bacteria begin to produce invasive machinery capable of degrading host tissue.[5] During later stages of chronic infections, QS often heavily regulates architecture and integrity of biofilms, which can be responsible for infection persistence.[6, 7] Increasing numbers of bacterial infections are becoming resistant to traditional antibiotic therapies;[8] thus, QS systems that are closely tied to virulence have emerged as attractive alternative targets for infection treatment.[9, 10] Additionally, recent studies indicate that applying such "antivirulence" approaches to treating infections—as opposed to targeting whole-cell growth—minimize selective pressure for resistant mutants to emerge.[11-13] More fundamentally, chemical interventions provide novel insights— ones that might not be readily elucidated using traditional genetic methods[14, 15]—into the molecular mechanisms of QS. This disclosure identifies new small-molecule modulators that target the QS systems in certain virulent bacterial species, particularly Gram-negative bacteria, including bacteria of the genus *Pseudomonas* and more specifically of the species *Pseudomonas aeruginosa*.

The Gram-negative pathogen *Pseudomonas aeruginosa*, a bacterium well known for its complex QS circuitry, has been heavily studied due to its remarkable recalcitrance to antibiotic treatment, most notably in chronic infections located in the lungs of cystic fibrosis patients.[16-18] *P. aeruginosa* is an opportunistic pathogen; thus, it commonly affects immunocompromised patients (those suffering from HIV, burn wounds, chronic wounds, etc.).[19] In fact, *P. aeruginosa* is the leading cause of hospital-acquired pneumonia.[20] Many virulence factors produced by *P. aeruginosa* are controlled by a complex network of QS circuits (FIG. 1). This pathogen uses multiple LuxI/LuxR pairs to regulate virulence factor expression during the course of infection: The LuxI-type synthase LasI produces N-(3-oxododecanoyl) HL (OdDHL; FIG. 2), and RhlI produces N-butanoyl HL (BHL; FIG. 2).[21] These two signaling molecules are recognized by the receptors LasR and RhlR, respectively. Both QS circuits regulate a large number of virulence factors—for example, the Las system regulates the production of elastase, alkaline protease, and exotoxin A;[22] and the Rhl system regulates rhamnolipid production (a rhamnose-based biosurfactant) and the toxic exofactors hydrogen cyanide and pyocyanin.[23] In addition to culture-based virulence factor assays, studies using animal models have shown that genetic mutation of these circuits attenuates virulence in vivo;[24-26] thus, disruption of QS using small-molecule modulators is of significant clinical importance.

Adding to the complexity of the *P. aeruginosa* QS system, each of the QS circuits is intertwined, allowing intricate genome regulation based on social and environmental cues.[27, 28] Generally considered to be at the top of the *P. aeruginosa* QS hierarchy is LasR, which regulates the rhl circuit by activating both the rhlI and rhlR genes.[29, 30] Because effectively antagonizing LasR could feasibly inhibit multiple QS circuits, this receptor has been the primary target of chemical modulation research. There are multiple literature report concerning the generation and/or screening of libraries to find small molecules capable of modulating LasR.[31, 32] A large subsection of these molecules are higher in molecular weight (generally >250 Da), designed to fit the larger binding pocket (which accommodates OdDHL) of LasR.

Fewer research efforts have been directed toward RhlR, likely due to its perceived lower position in the *P. aeruginosa* QS hierarchy. However, a number of reports have begun to upend this traditional view of the QS regulatory blueprint. Broadly, both the nutrient conditions and stage of bacterial growth are influential in rerouting QS regulatory circuitry. It has been reported that starvation can restore phenotypes known to be controlled by RhlR.[33] More recently, it has been reported that pyocyanin can be expressed in lasR mutants and that RhlR in particular (in late stationary phase) is able to overcome the absence of the las system by activating functions previously thought to be regulated solely by LasR.[34] It has also been reported that though las function is lost in mid-stage infection of cystic fibrosis patients, virulence factors are still produced via the rhl system.[17, 35] Very recently, the discovery of a new signaling molecule, IQS, that facilitates the activation of the rhl system (independently of LasR) under phosphate-limited conditions was reported.[36] Finally, studies using small-molecule modulators have reported that the rhl system is implicated in the direct regulation of virulence factors. In a study using halogenated thiolactone AHL mimics, it has been reported that these mimics exert their phenotypic effect by primarily acting upon the rhl system.[37] The compound mBTL, a RhlR partial agonist, was reported to reduce *P. aeruginosa* virulence in a *C. elegans* infection model. We have more recently shown that small-molecule inhibition of pyocyanin can be achieved via agonism of RhlR.[38] This inverse phenotypic effect occurs through RhlR's downstream repression of the pqs quorum sensing circuit (FIG. 1).

As a whole, the RhlR receptor presents a significantly underdeveloped opportunity for *P. aeruginosa* virulence phenotype modulation; furthermore, agonism of this receptor can decrease virulence factor production and overall pathogenicity. Additional synthetic agonists and antagonist of RhlR are of interest in the art for modulation of virulence in Gram-negative bacteria, particularly bacteria of the genus *Pseudomonas* and more specifically of the species *Pseudomonas aeruginosa*. New modulators of RhlR are useful in various applications including therapeutic applications and as research tools for the further investigation of Quorum sensing systems.

SUMMARY

The disclosure provides RhlR modulators including agonist and antagonists which are useful for modulating QS phenotypes in Gram-negative bacteria. Certain compounds of formulas I, II, III and IV are provided as are methods of using the compounds. Compositions useful for decreasing the virulence of Gram-negative bacteria are provided including one or more of the compounds of formula I, II, III and IV. In embodiments, compounds as claimed exclude those which are natural QS modulators. In embodiments, compounds as claimed exclude those which are natural QS modulators in *P. aeruginosa*. Pharmaceutical compositions comprising the RhlR modulators are provided. In embodiments, compounds as claimed exclude those which are BHL, D8 and S4 as defined herein. In an embodiment, compounds as claimed are those having a head group other than AHL.

The disclosure provides a method of modulating RhlR of a Gram-negative bacterium having such a QS receptor by contacting the bacterium with a compound of formula I, II, III or IV herein.

The disclosure provides a method of inhibiting RhlR of a Gram-negative bacterium having such a QS receptor by contacting the bacterium with a compound of formula I, II, III or IV herein which is an RhlR antagonist.

The disclosure provides a method of activating RhlR of a Gram-negative bacterium having such a QS receptor by contacting the bacterium with a compound of formula I, II, III or IV herein which is an RhlR agonist.

Certain compounds of the disclosure are useful in treating infections of Gram-negative bacteria by administering to an individual in need of such treatment a RhlR modulator as disclosed herein.

DETAILED DESCRIPTION

Figure 1:
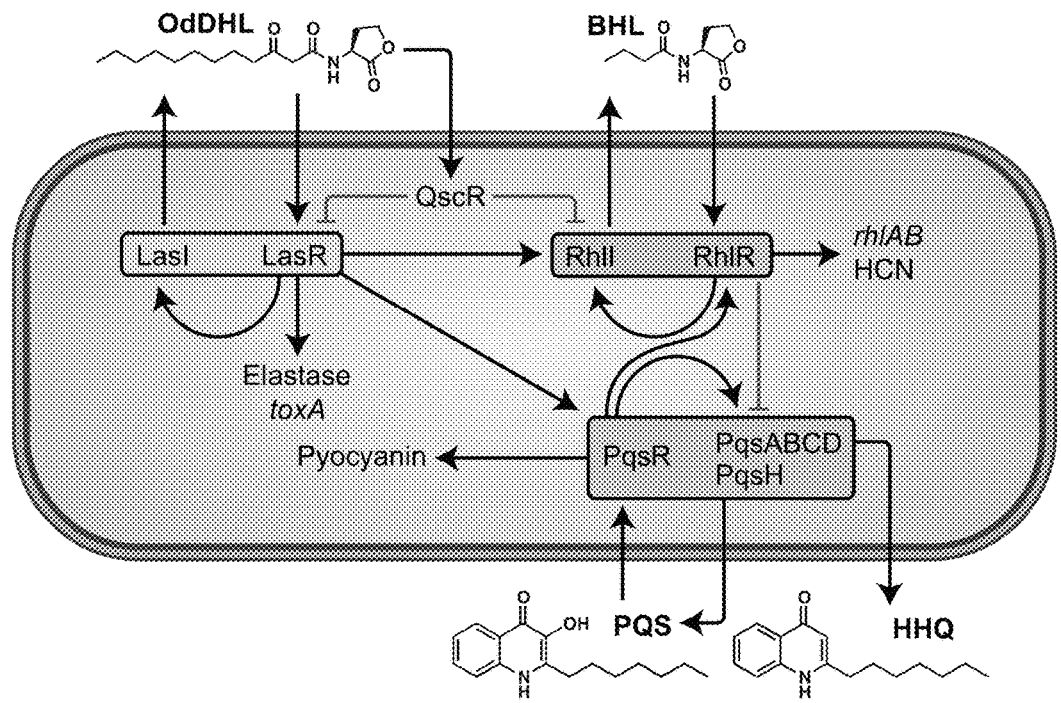
FIG. 1: Simplified scheme of the *Pseudomonas aeruginosa* quorum sensing network. Arrows represent positive feedback (autoinducer synthesis/transcriptional regulation/receptor binding, etc.). Flat arrows represent negative regulation.
Figure 2:
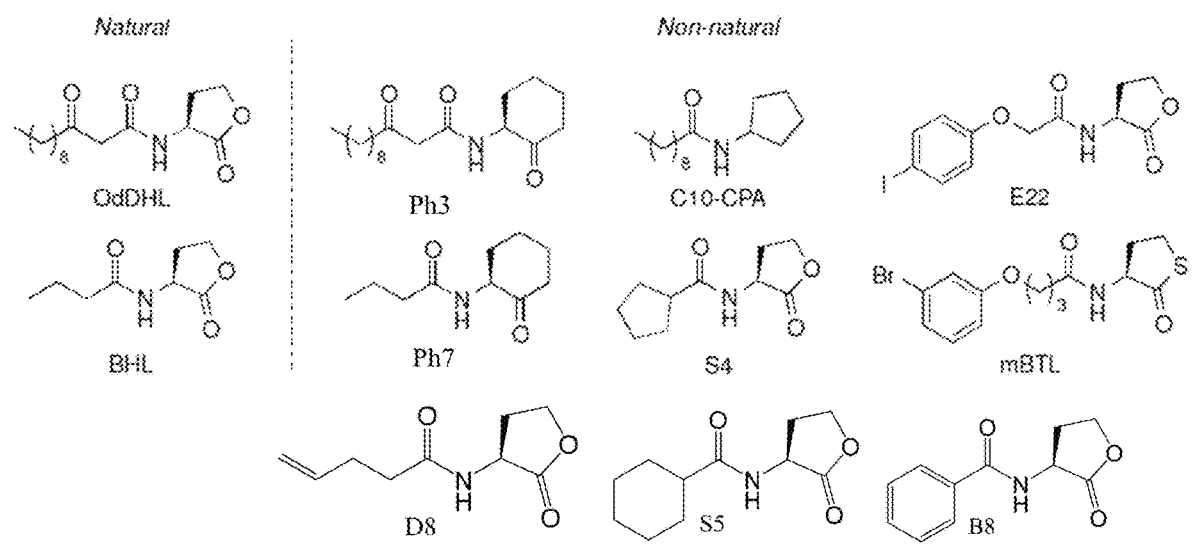
FIG. 2: General structure of AHLs and selected examples of natural and non-natural modulators of QS in *P. aeruginosa*. Non-natural compounds Ph3 and Ph7 are at least described in Smith et al. (2003) Chemistry & Biology 10:81; C10-CPA is at least described in Ishida et al. (2007) Applied Environ. Microbiology 73:3183; S4 and E22 are at least described in Eibergen et al. (2015) ChemBioChem 16:2348 and mBTL is at least described in O'Loughlin et al. (2013) Proc. Natl. Acad. Sci. USA 110:17981. Each of which is incorporated by reference herein in its entirety for such description.

The present disclosure relates to modulation of the QS receptor RhlR. The RhlR system of *P. aeruginosa* was employed as an exemplary RhlR system.

A reference, and associated supporting information available on-line from the journal, relating to modulation of the RhlR Quorum Sensing Receptor: Eibergen et al. 2015[51] is incorporated by reference herein in its entirety at least for additional synthetic methods or details of methods applicable to the synthesis of compounds herein, additional methods or details of methods of assessment of modulation of RhlR, and for structures of additional RhlR modulators.

A reference, and associated supporting information available on-line from the journal, relating more generally to Quorum Sensing modulation in *P. aeruginosa*: Moore, et al. 2015[52] is incorporated by reference herein in its entirety at least for additional synthetic methods or details of methods applicable to the synthesis of compounds herein, additional methods or details of methods of assessment of modulation of QS receptors and for structures of certain QS modulators. Additionally Moore et al. 2015 discusses details of active efflux on QS modulators.

A reference, and associated supporting information available on-line from the journal, relating more generally to modulators of a LuxR-Type QS receptor: O'Reillly et al. 2016[53] is incorporated by reference herein in its entirety at least for additional synthetic methods or details of methods applicable to the synthesis of compounds herein, additional methods or details of methods of assessment of modulation of QS receptors and for structures of certain QS modulators.

A reference, and associated supporting information available on-line from the journal, relating to QS cross-regulation: Welsh et al. 2015[38] is incorporated by reference herein in its entirety at least for additional synthetic methods or details of methods applicable to the synthesis of compounds herein, additional methods or details of methods of assessment of modulation of QS receptors and for structures of certain QS modulators.

A reference, and associated supporting information available on-line from the journal relating to this invention: Boursier et al. (2018)[72] is incorporated by reference herein in its entirety at least for additional details of methods applicable to the synthesis of compounds herein, additional methods or details of methods of assessment of modulation of QS receptors and for any additional structures of certain QS modulators.

Compounds were assessed using a bioassay that reports on the activity of heterologously expressed RhlR. Because, in certain growth conditions, RhlR is particularly susceptible to regulation by other QS receptors (which might also recognize these AHL analogs), a heterologous (*E. coli*) reporter strain that recombinantly expresses rhlR was used to isolate RhlR activity from the remainder of the complex *P. aeruginosa* QS circuitry and enable the determination of direct AHL-RhlR SARs.

The most potent hits of this library were then assessed using an RhlR reporter in *P. aeruginosa* to confirm the efficacy of these compounds in a more directly relevant bacterial system. Among these compounds, some of the most potent RhlR agonists yet characterized were identified, and additional structural features that facilitate potent RhlR activation were identified.

In one aspect, RhlR modulators of the disclosure include compounds of formula I:

A-W-HG where:
—W— is —CO—NH—, —SO$_2$—NH—, —CO—NH—CH$_2$—, or —SO$_2$—NH—CH$_2$—;
A is selected from one or more of:
(1) an unsubstituted straight-chain alkyl group having 2-5 carbon atoms;
(2) an unsubstituted branched alkyl group having 3-7 carbon atoms, where the carbon alpha to W carries one or two hydrogen;
(3) an unsubstituted cycloalkyl group having a total 3-7 carbon atoms with a 3-5 member carbon ring, where the carbon alpha to W carries one or two hydrogen;
(4) an unsubstituted straight-chain or branched alkenyl group having 3-6 carbon atoms, where the carbon alpha to W carries one or two hydrogen; and
(5) an unsubstituted straight-chain or branched alkynyl group having 3-6 carbon atoms, where the carbon alpha to W carries one or two hydrogen; and HG (head group) is selected from carbocyclic and heterocyclic cyclic groups of formula:

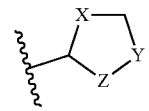

where:
X is CH$_2$, O, S or NH;
Y is CH$_2$, O, S or NH; and
Z is CH$_2$, C=O or CH(OH);
with the exception that the compound is not BHL.

In a specific embodiment of the RhlR modulators of formula I, the modulator is a compound other than BHL, D8 or S4 (the structures of which are shown herein). In a specific embodiment of the RhlR modulators of formula I, the modulator is a compound other than BHL. In a specific embodiment of the RhlR modulators of formula I, the modulator is a compound other than D8. In a specific embodiment of the RhlR modulators of formula I, the modulator is a compound other than S4.

In specific embodiments, X is CH$_2$, Y is O and Z is CO. More specifically, HG is:

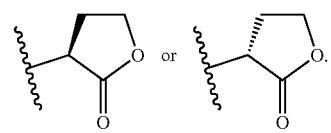 [SMILES: *[C@H]1CCOC1=O ; *[C@@H]1CCOC1=O]

In specific embodiments, X is CH$_2$, Y is S and Z is CO. More specifically, HG is:

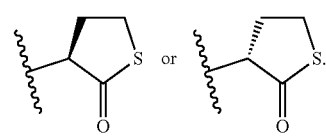 [SMILES: *[C@H]1CCSC1=O ; *[C@@H]1CCSC1=O]

In specific embodiments, each of X, Y and Z is CH$_2$.
In specific embodiments, X is O and both of Y and Z are CH$_2$.
In specific embodiments, X is S and both of Y and Z are CH$_2$.
In specific embodiments, X is NH and both of Y and Z are CH$_2$.
In specific embodiments, both X and Y are CH$_2$ and Z is CO. More specifically HG is:

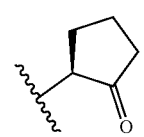 [SMILES: *[C@H]1CCCC1=O]

In specific embodiments, both X and Y are CH$_2$ and Z is CH(OH). More specifically HG is:

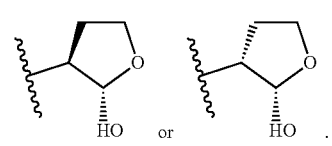 [SMILES: *[C@H]1CCO[C@@H]1O ; *[C@@H]1CCO[C@@H]1O]

In specific embodiments, —W— is —CO—NH—CH$_2$—, and all of X, Y and Z are CH$_2$.

In specific embodiments, —W— is —CO—NH—CH$_2$—, X is O and, both of Y and Z are CH$_2$.

In specific embodiments, —W— is —CO—NH—CH$_2$—, X is NH and both of Y and Z are CH$_2$.

In specific embodiments, —W— is —CO—NH—CH$_2$—, X is S and both of Y and Z are CH$_2$.

In specific embodiments, when —W— is —CO—NH—, HG is a group other than AHL:

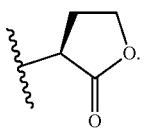

In specific embodiments, when A is an unsubstituted straight-chain alkyl group having 2-5 carbon atoms, HG is a group other than AHL. In specific embodiments, when A is an unsubstituted branched alkyl group having 3-7 carbon atoms, where the carbon alpha to W carries one or two hydrogen, HG is a group other than AHL. In specific embodiments, when A is an unsubstituted cycloalkyl group having a total 3-7 carbon atoms with a 3-5 member carbon ring, where the carbon alpha to W carries one or two hydrogen, HG is a group other than AHL. In specific embodiments, when A is an unsubstituted straight-chain or branched alkenyl group having 3-6 carbon atoms, where the carbon alpha to W carries one or two hydrogen, HG is a group other than AHL. In specific embodiments, when A is an unsubstituted straight-chain or branched alkynyl group having 3-6 carbon atoms, where the carbon alpha to W carries one or two hydrogen, HG is a group other than AHL.

In another aspect, the disclosure relates to compounds of formula II:

AII-L-W-HGII where:
—W— is —CO—NH—, —SO$_2$—NH—, —CO—NH—CH$_2$—, or —SO$_2$—NH—CH$_2$—;
L is —(CH$_2$)$_n$—, or —O—(CH$_2$)$_m$—, where n is 1, 2 or 3 and m is 1 or 2;
AII is selected from one or more of:
(1) a phenyl group substituted with one or more halogen, nitro group, alkyl group having 1-3 carbon atoms, haloalkyl group having 1-3 carbon atoms, an —O—R$_{II}$, and an —S—R$_{II}$ group, where R$_{II}$ is an alkyl or haloalkyl group having 1-3 carbon atoms;
(2) an optionally substituted naphthyl group; or
(3) when L is —(CH$_2$)$_3$—, an optionally substituted cyclopentyl or cyclohexyl group,
where the groups of (2) or (3) are optionally substituted with one or more halogen, nitro group, alkyl group having 1-3 carbon atoms, haloalkyl group having 1-3 carbon atoms, an —O—R$_{II}$, and an —S—R$_{II}$ group, where R$_{II}$ is an alkyl or haloalky group having 1-3 carbon atoms; and
HGII is a cyclic group other than AHL of formula:

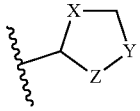

where:
X is CH$_2$, O, S or NH;
Y is CH$_2$, O, S or NH; and
Z is CH$_2$, C═O or CH(OH).

In specific embodiments, HGII is

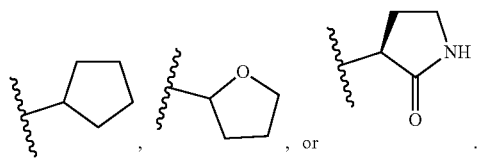

In specific embodiments, HGII is

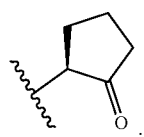 [SMILES: *[C@H]1CCCC1=O]

In more specific embodiments, HGII is

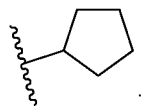

In more specific embodiments, HGII is

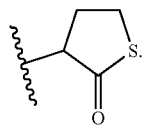

In more specific embodiments, HGII is

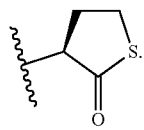

In more specific embodiments, HGII is

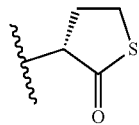

In specific embodiments, AII is p-I-phenyl. In specific embodiments, AII is p-I-phenyl and L is —O—(CH$_2$)$_m$—, where m is 1 or 2. In specific embodiments, AII is p-I-phenyl and L is —O—(CH$_2$)$_m$—, where m is 1 or 2, and W is —CO—NH— or —CO—NH—CH$_2$—. In specific embodiments, AII is p-I-phenyl, L is —O—(CH$_2$)$_m$—, where m is 1 or 2, and W is —CO—NH—. In specific embodiments, AII is p-I-phenyl, L is —O—(CH₂)—, and W is —CO—NH—.

In specific embodiments, AII is p-I-phenyl and HGII is

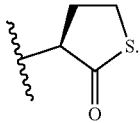

In specific embodiments, AII is p-I-phenyl and L is —O—(CH$_2$)$_m$—, where m is 1 or 2 and HGII is

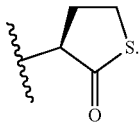

In specific embodiments, AII is p-I-phenyl and L is —O—(CH$_2$)$_m$—, where m is 1 or 2, and W is —CO—NH— or —CO—NH—CH$_2$— and HGII is

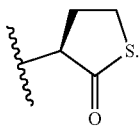 [SMILES: *[C@H]1CCSC1=O]

In specific embodiments, AII is p-I-phenyl, L is —O—(CH$_2$)$_m$—, where m is 1 or 2, and W is —CO—NH— and HGII is

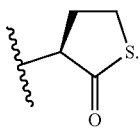

In specific embodiments, AII is p-I-phenyl, L is —O—(CH$_2$)—, and W is —CO—NH— and HGII is

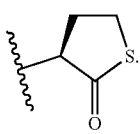

In embodiments, the compound of formula II is

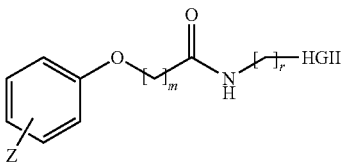

IIB where Z represents substitution of the phenyl ring with 1-5 halogens, m is 1 or 2, r is 0 or 1 and HG II is as defined above for formula II. In specific embodiments, m is 1 and r is 0. In specific embodiments, m is 1 and r is 1.

In specific embodiments, Z represents substitution of the phenyl ring with 1, 2 or 3 halogens. In specific embodiments, Z represents substitution of the phenyl ring with 1, 2 or 3 halogens including a halogen in the para-ring position. In specific embodiments, Z represents substitution of the phenyl ring with 1, 2 or 3 halogens including a iodine in the para ring position. In specific embodiments, Z represents two halogens substituted on the phenyl ring. In specific embodiments, Z represents two halogens substituted on the phenyl ring. In specific embodiments, Z represents two halogens substituted on the phenyl ring with one of the halogens in the para ring position on the ring. In specific embodiments, Z represents two halogens substituted on the phenyl ring with one iodine in the para ring position on the ring. In specific embodiments, Z represents one halogen substituted on the phenyl ring. In specific embodiments, Z represents one halogen substituted on the phenyl ring in the para ring position. In specific embodiments, the halogens are I, Cl or F. In specific embodiments, the halogens are Br. In specific embodiments, the halogens are F. In specific embodiments, the halogens are I.

In specific embodiments of formula IIB, HGII is

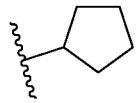

In specific embodiments of formula IIB, HGII is

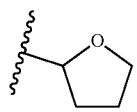

In further embodiments of this HGII group, r is 1.

In specific embodiments of formula IIB, HGII is

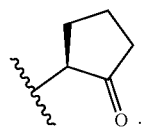

In specific embodiments of formula IIB, HGII is:

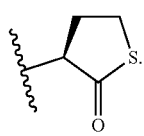

In specific embodiments, the compounds of formula IIB are QS antagonists of a Gram-negative bacterium having a RhlR QS receptor. In specific embodiments, the Gram-negative bacterium is a species of the genus *Pseudomonas*. In specific embodiments, the Gram-negative bacterium is *Pseudomonas aeruginosa*. In specific embodiments, the *Pseudomonas* species is *P. putida*, or *P. syringae*. In specific embodiments, the Gram-negative bacterium is a species of the genus *Burkholderia*. In specific embodiments, the species of *Burkholderia* is *B. cepacia*, *B. pseudomallei*, or *B. mallei*.

In specific embodiments, the compounds of formula IIB are those which exhibit $IC_{50}$ measured as described herein in the *E. coli* reporter screen of 50 µM or less. In specific embodiments, the compounds of formula IIB are those which exhibit $IC_{50}$ measured as described herein in the *E. coli* reporter screen of µM or less.

In specific embodiments, the compounds of formula IIB are those which exhibit $IC_{50}$ measured as described herein in the *P. aeruginosa* reporter screen of 50 µM or less. In specific embodiments, the compounds of formula IIB are those which exhibit $IC_{50}$ measured as described herein in the *P. aeruginosa* reporter screen of 25 µM or less.

In specific embodiments, the compounds of formula IIB are those which exhibit maximum inhibition measured as described herein in the *E. coli* reporter screen of 30% or more with respect to 10 µM BHL. In specific embodiments, the compounds of formula IIB are those which exhibit maximum inhibition measured as described herein in the *E. coli* reporter screen of 50% or more with respect to 10 µM BHL. In specific embodiments, the compounds of formula IIB are those which exhibit maximum inhibition measured as described herein in the *E. coli* reporter screen of 75% or more with respect to 10 µM BHL.

In specific embodiments, the compounds of formula IIB are those which exhibit maximum inhibition measured as described herein in the *P. aeruginosa* reporter screen of 30% or more. In specific embodiments, the compounds of formula IIB are those which exhibit maximum inhibition measured as described herein in the *P. aeruginosa* reporter screen of 50% or more. In specific embodiments, the compounds of formula IIB are those which exhibit maximum inhibition measured as described herein in the *P. aeruginosa* reporter screen of 75% or more.

In specific embodiments, the RHlR modulator is a compound of formula III:

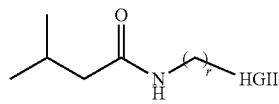

where:
r is 0 or 1 and HGII is a cyclic group other than AHL as defined for formula II.

In specific embodiments, r is 1 and HGII is

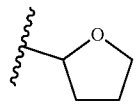

In specific embodiments, r is 0 and HGII is

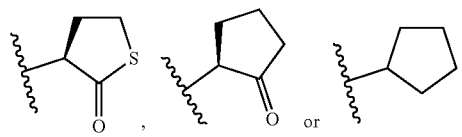

The disclosure relates to a method for modulating RhlR in a Gram-negative bacterium employing RhlR modulators of formula I or II. The modulation may be agonism or antagonism. Compounds of the disclosure can be selected as agonist or antagonists in view of information provided herein. Agonism and antagonism include partial agonism and partial antagonism, respectively.

In an embodiment, RhlR agonists are those of formula I, where:
W is as defined above;
A is selected from one or more of:
(1) an unsubstituted straight-chain alkyl group having 2-5 carbon atoms;
(2) an unsubstituted branched alkyl group having 3-7 carbon atoms, where the carbon alpha to W carries one or two hydrogen;
(3) an unsubstituted cycloalkyl group having a total 3-7 carbon atoms with a 3-5 member carbon ring, where the carbon alpha to W carries one or two hydrogen; and
HG is

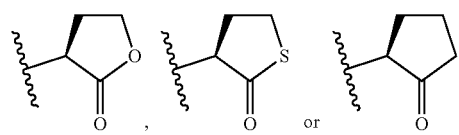

In specific embodiments, RhlR agonists are those of formula I, where:
W and A are as defined above; and HG is

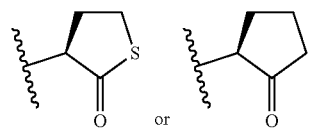

In specific embodiments, the disclosure provides compounds of formula I where when A is an unsubstituted straight-chain alkyl group having 2-5 carbon atoms and —W— is —CO—NH—CH$_2$—, and HG is

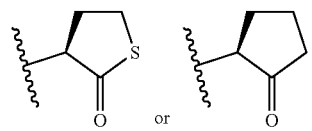

In specific embodiments, the disclosure provides RhlR agonists of formula I where —W— is —CO—NH—CH$_2$—, HG is

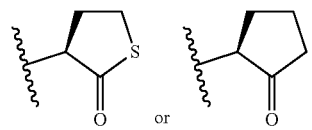

and
A is cyclopentyl, cyclobutyl, cyclopropylmethyl, cis-but-2-enyl, isopropyl (1-methylethyl), 1-methyl propyl, or 2-methyl propyl.

In specific embodiments, the disclosure provides RhlR agonists of formula I where —W— is —CO—NH—CH$_2$—, HG is AHL

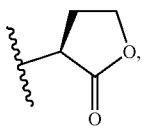 [SMILES: *[C@H]1CCOC1=O]

and

A is cyclopentyl, cyclobutyl, cyclopropylmethyl, (Z)-but-2-enyl, isopropyl (1-methylethyl), 1-methylpropyl, or 2-methylpropyl and more specifically A is cyclobutyl, cyclopropylmethyl, cis-but-2-enyl, isopropyl (1-methylethyl), 1-methyl propyl, or 2-methyl propyl or yet more specifically A is cyclopropylmethyl, isopropyl (1-methylethyl), 1-methyl propyl, or 2-methyl propyl.

In an embodiment, RhlR antagonist are compounds of formula I where —W— is —CO—NH—, —SO$_2$—NH—, —CO—NH—CH$_2$—, or —SO$_2$—NH—CH$_2$—;
A is selected from"
(1) an unsubstituted straight-chain alkyl group having 2-5 carbon atoms;
(2) an unsubstituted branched alkyl group having 3-7 carbon atoms, where the carbon alpha to W carries one or two hydrogen;
(3) an unsubstituted cycloalkyl group having a total 3-7 carbon atoms with a 3-5 member carbon ring, where the carbon alpha to W carries one or two hydrogen;
(4) an unsubstituted straight-chain or branched alkenyl group having 3-6 carbon atoms, where the carbon alpha to W carries one or two hydrogen; and
(5) an unsubstituted straight-chain or branched alkynyl group having 3-6 carbon atoms, where the carbon alpha to W carries one or two hydrogen; and
HG is selected from

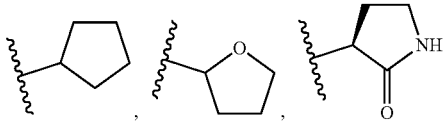

or
when —W— is -SO$_2$—NH—, or —SO$_2$—NH—CH$_2$—, HG can also be

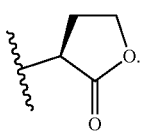

In specific embodiment, antagonists are compounds of formula I where:
—W— is —CO—NH—, or —SO$_2$—NH—, A is an unsubstituted alkyl having 3-5 carbon atoms or an unsubstituted cyclobutyl or cyclopentyl; and HG is HG is selected from:

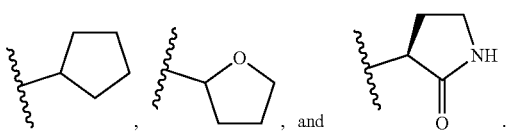

In other embodiments, RhlR antagonist are compounds of formula II.
In other embodiments, RhlR antagonists are compounds of formula IV:

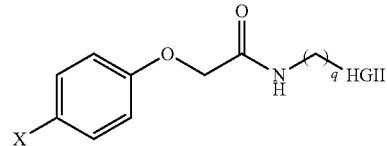

where q is 0 or 1;
Y is I, Br, Cl, CH$_3$, CF$_3$, O—CH$_3$, or O—CF$_3$, and HGII is

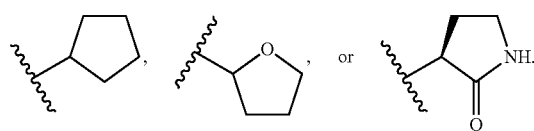

In specific embodiments of formula IV, q is 0 and HGII is

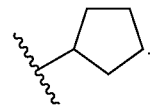 [SMILES: *C1CCCC1]

In more specific embodiments of formula IV, q is 1 and HGII is

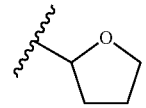

In more specific embodiments of formula IV, q is 0, HGII is

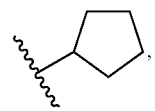

and
X is I, Br or CF$_3$.

Figures 1, 5:
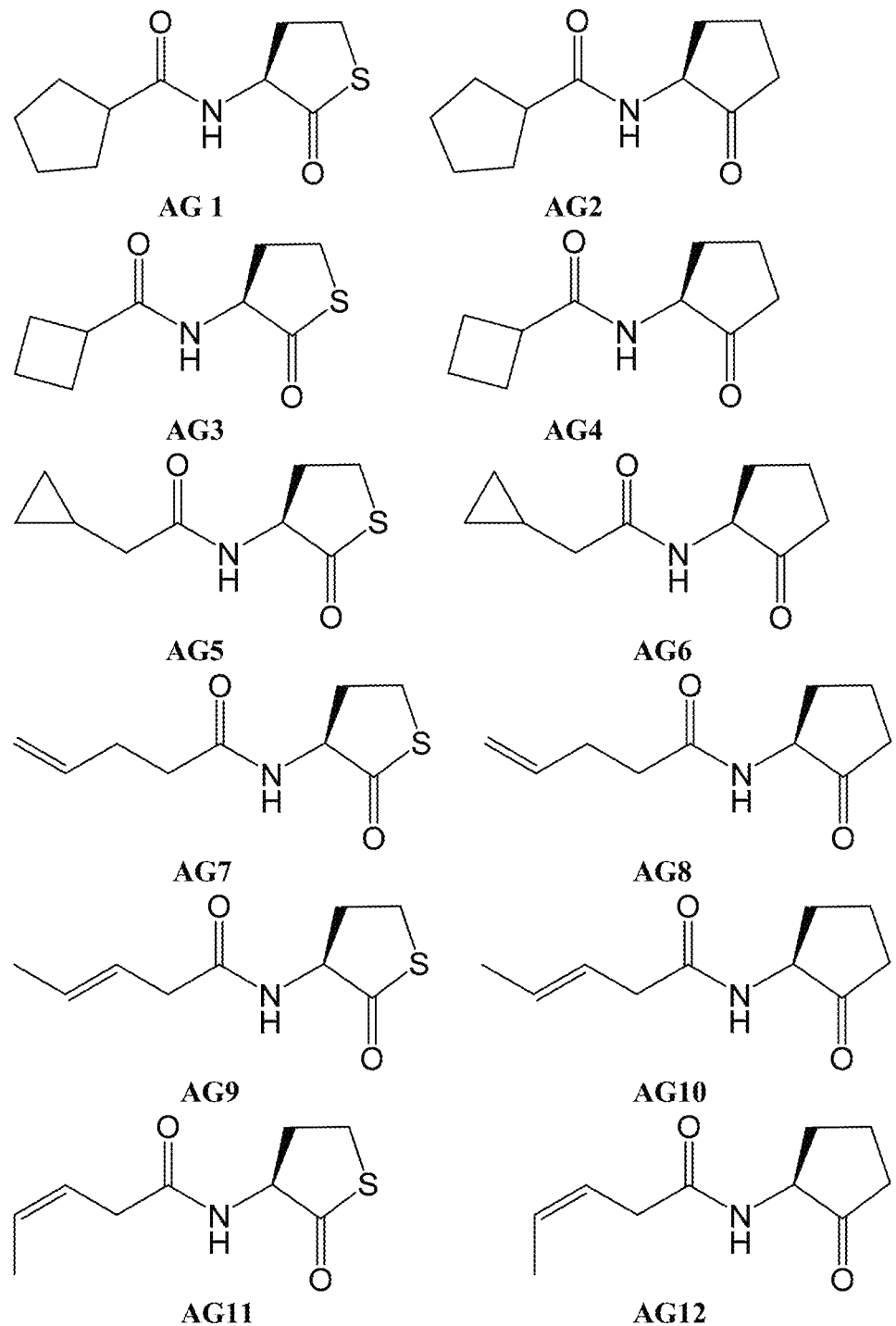
FIG. 5 (2 sheets) illustrate structures of exemplary RhlR modulators ih heterocyclic headgroups.
Figures 2, 5:
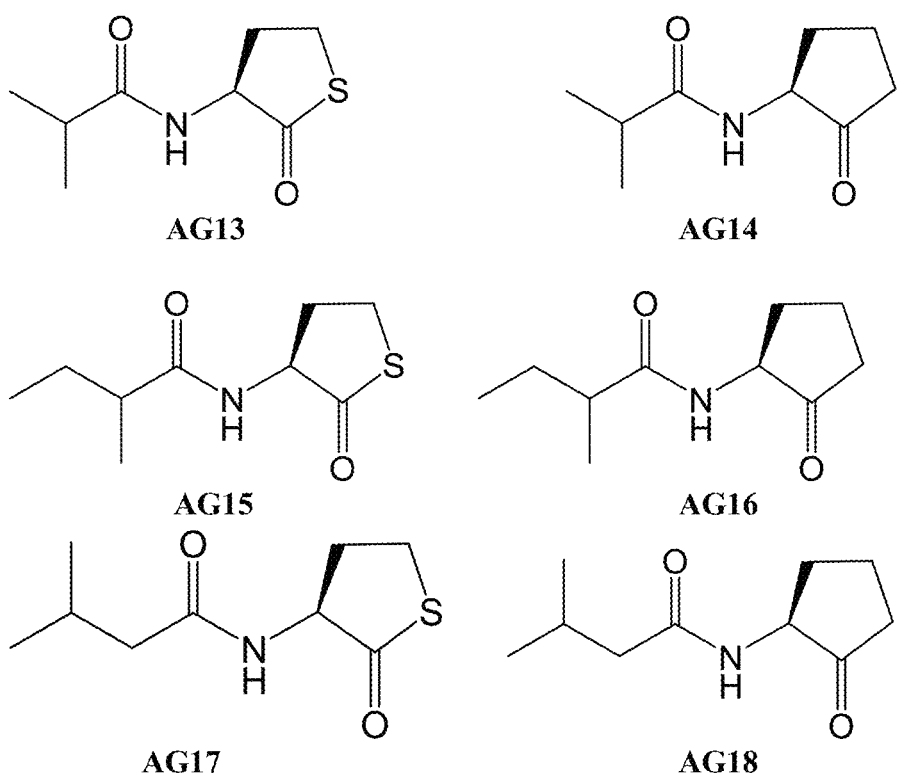
Figure 6:
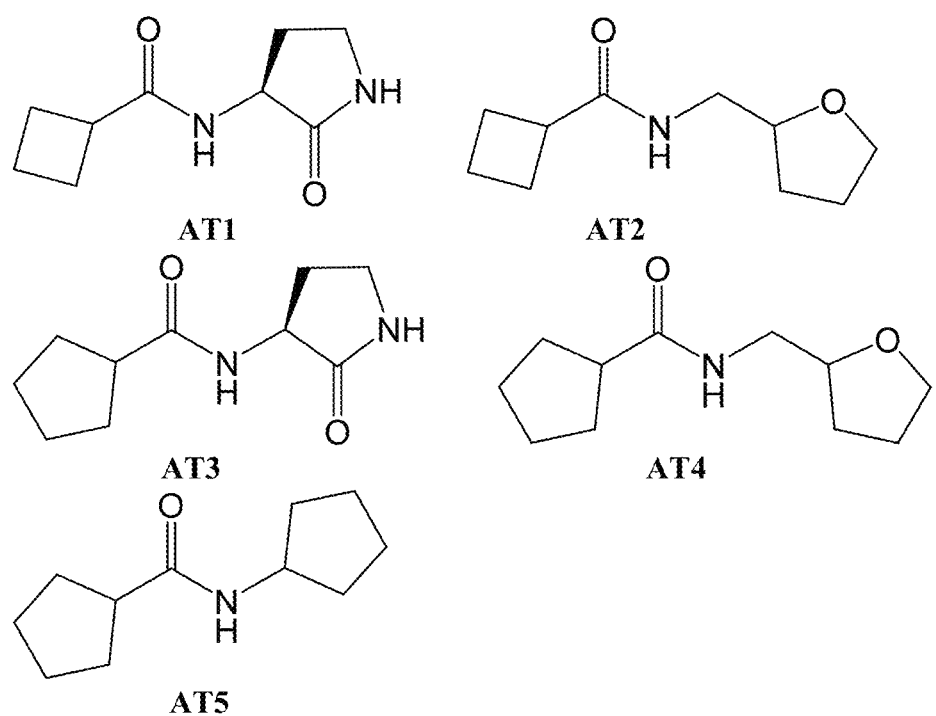
FIG. 6 illustrates structures of exemplary RhlR modulators with cycloalkyl tails.
Figures 1, 7:
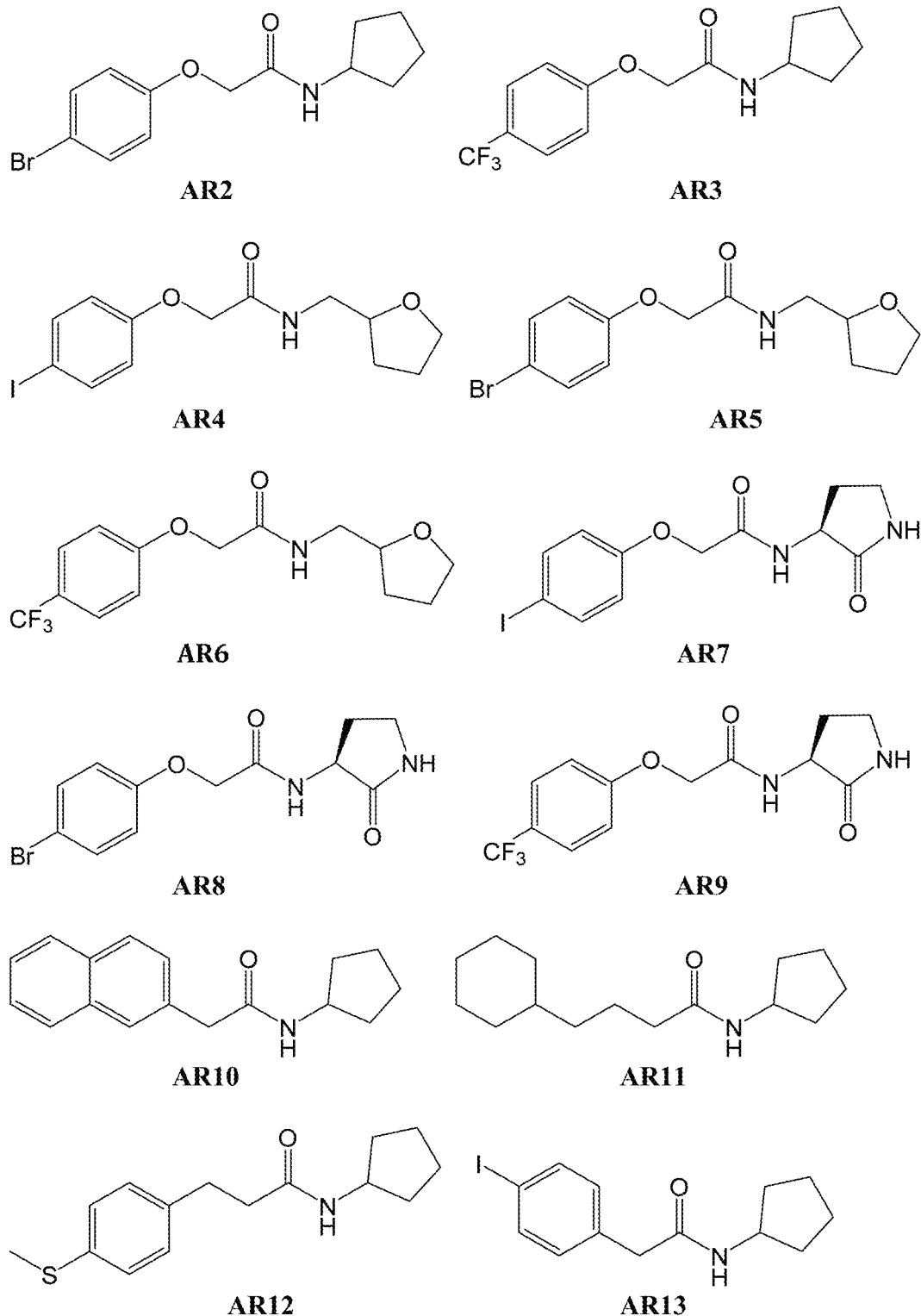
FIG. 7 (pages 1 and 2) illustrate structures of additional exemplary RhlR modulators.
Figures 2, 7:
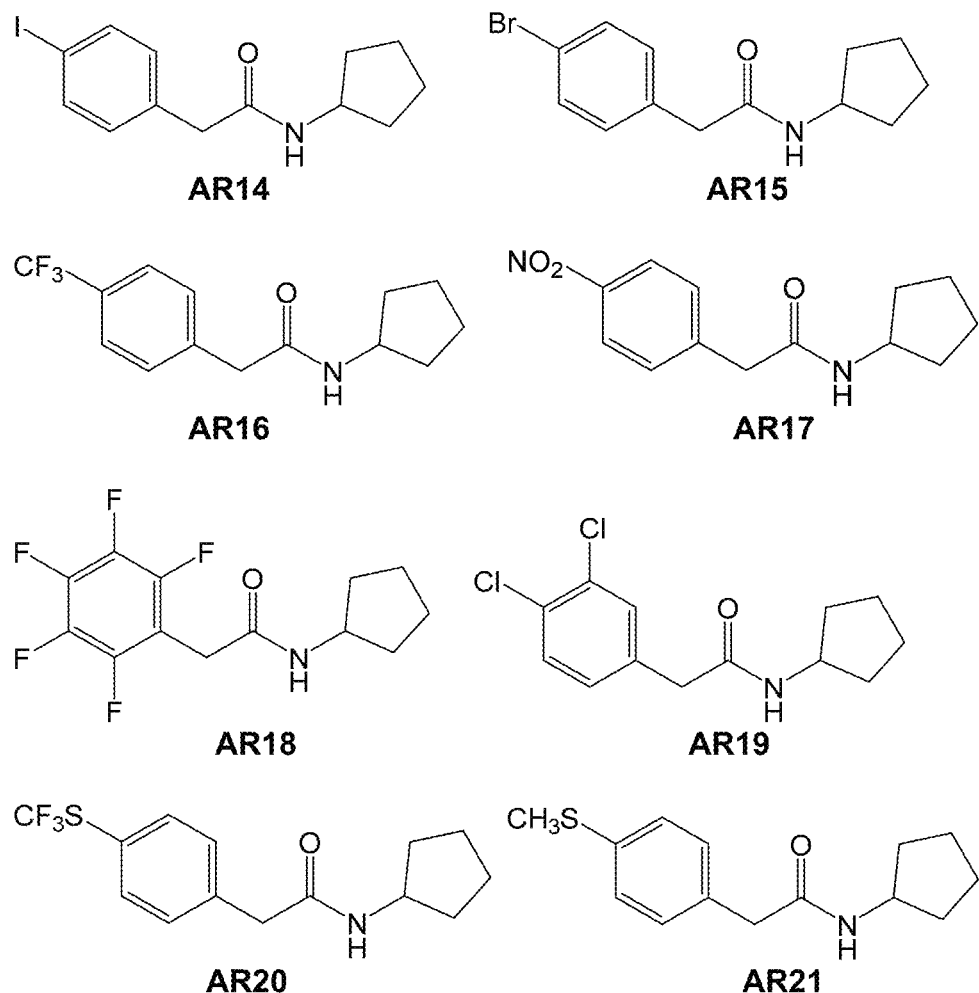
Figure 8A:
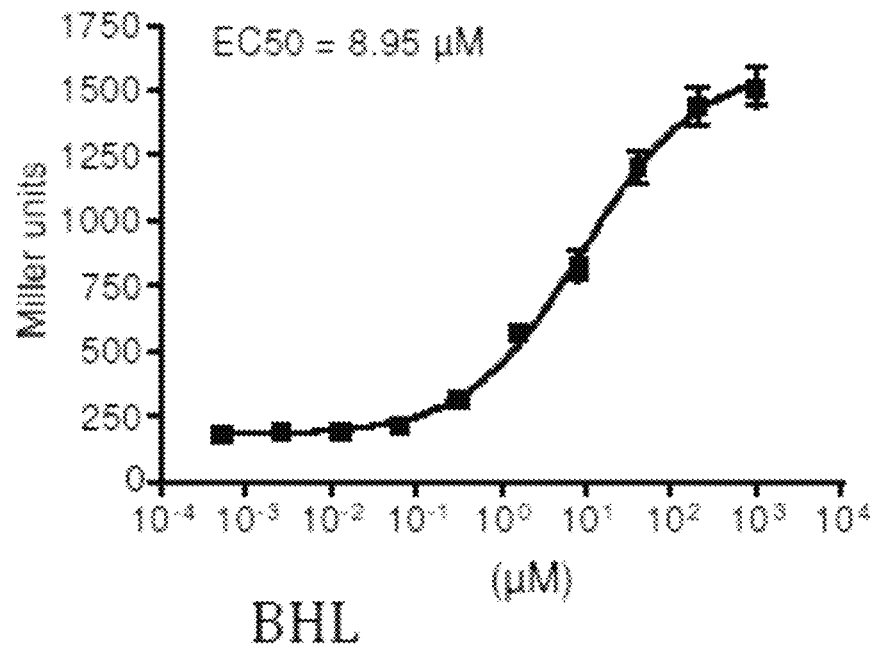
FIGS. 8A-8J illustrate a series of exemplary dose-response curves for RhlR agonism by BHL and certain synthetic AHLs. The compound for which the curve was measured is indicated on each figure. Assays were performed using the *E. coli* JLD271/pJN105R2/pSC11-rhlI* reporter strain. % Activity is defined as the activity of the synthetic AHL relative to maximum possible RhlR activity (i.e., activity effected by BHL at 1 mM). $EC_{50}$ values (in each figure) were calculated using GraphPad Prism. Error bars, SEM of n=3 trials.
Figure 8B:
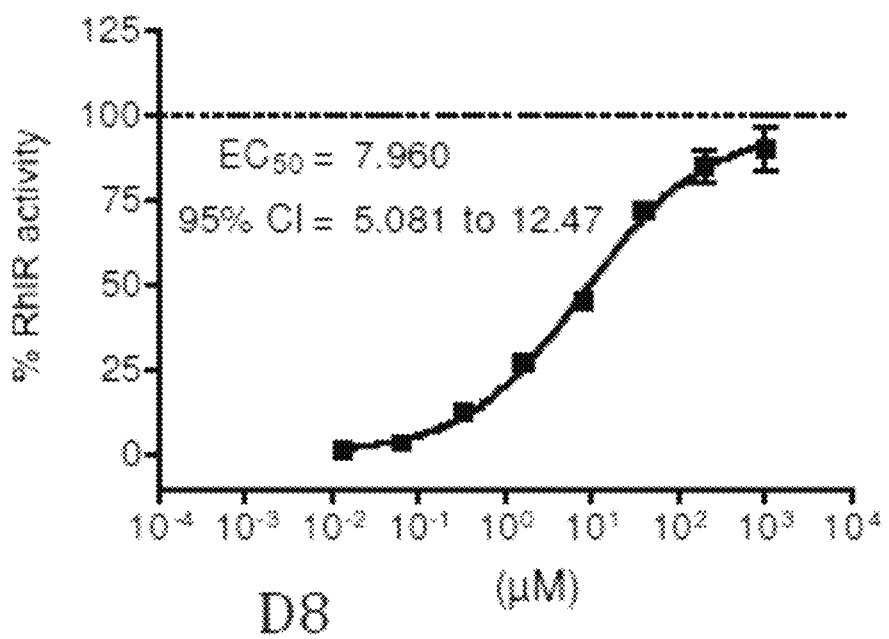
Figure 8C:
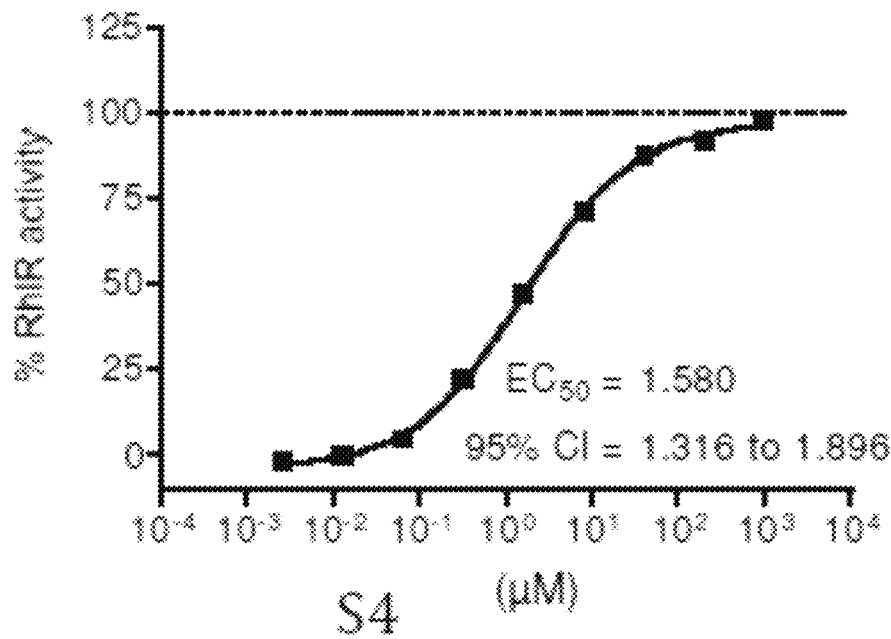
Figure 8D:
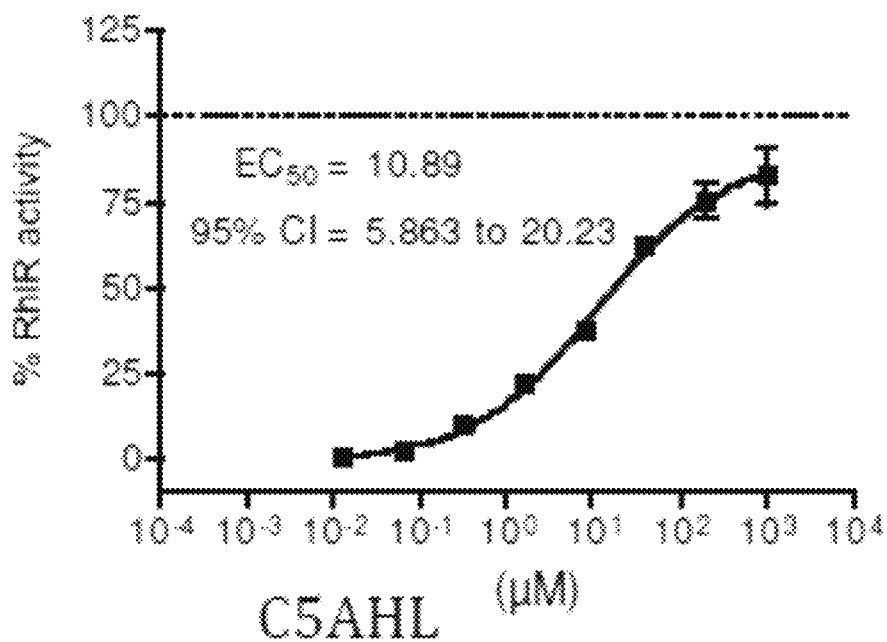
Figure 8E:
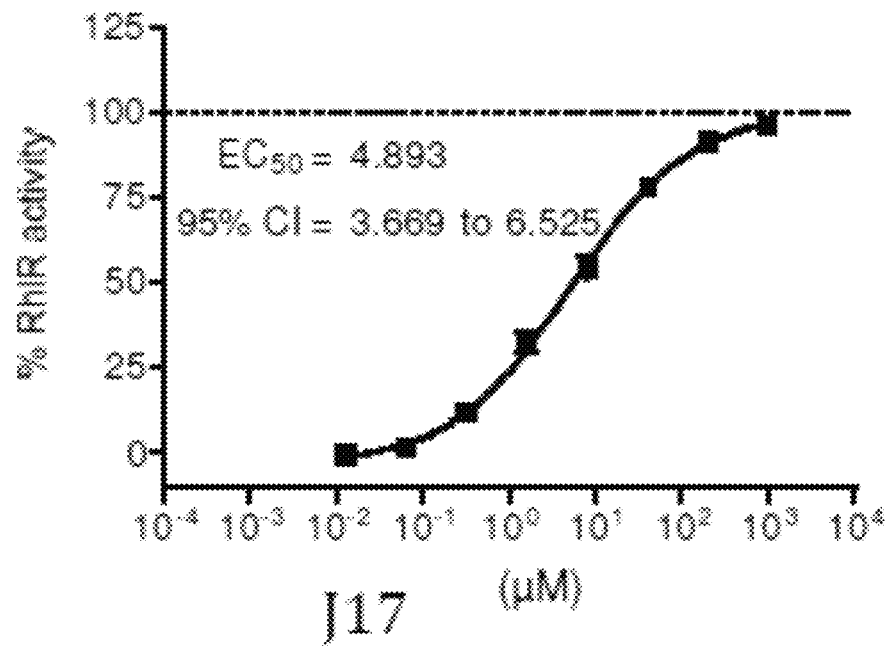
Figure 8F:
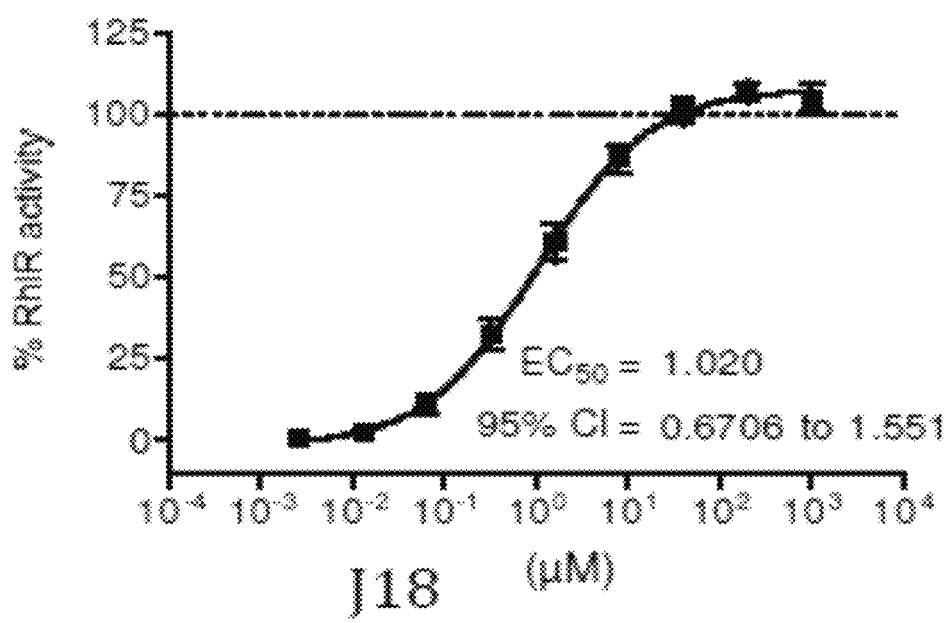
Figure 8G:
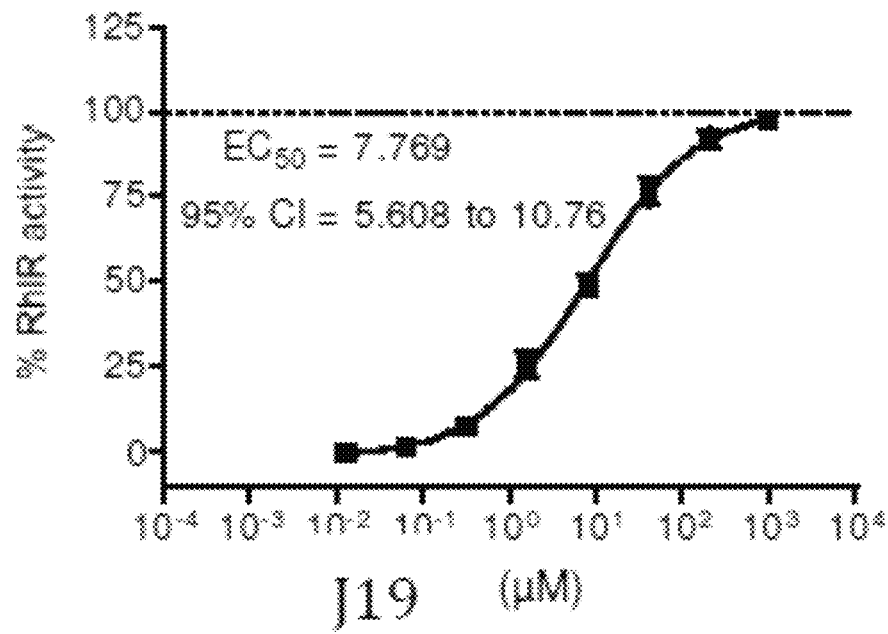
Figure 8H:
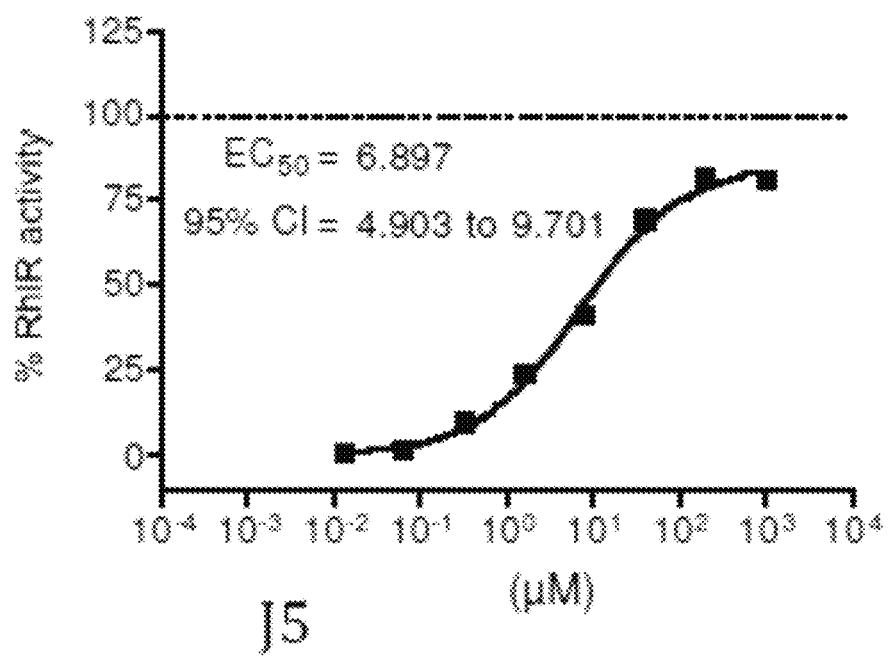
Figure 8I:
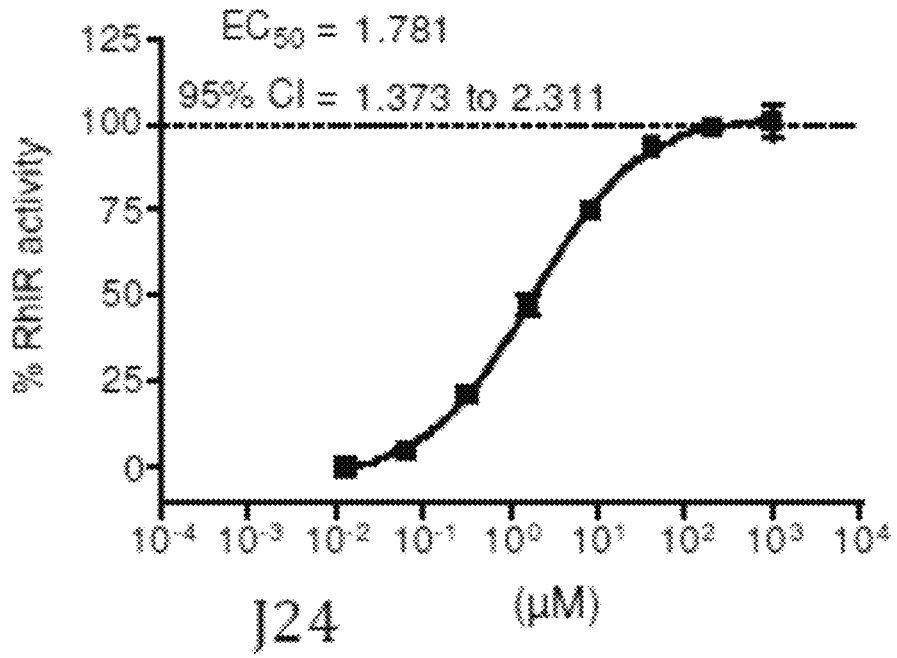
Figure 8J:
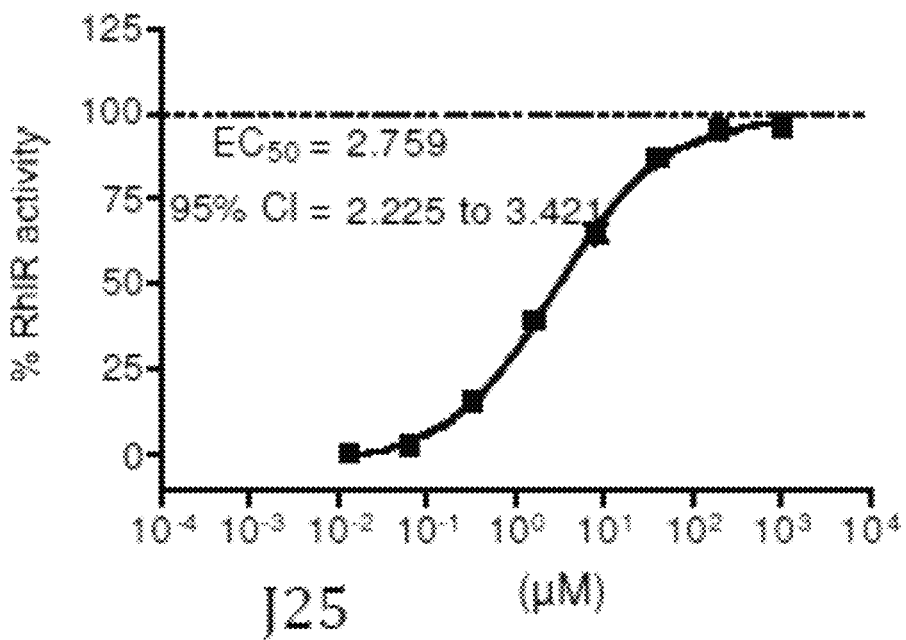
Figure 9A:
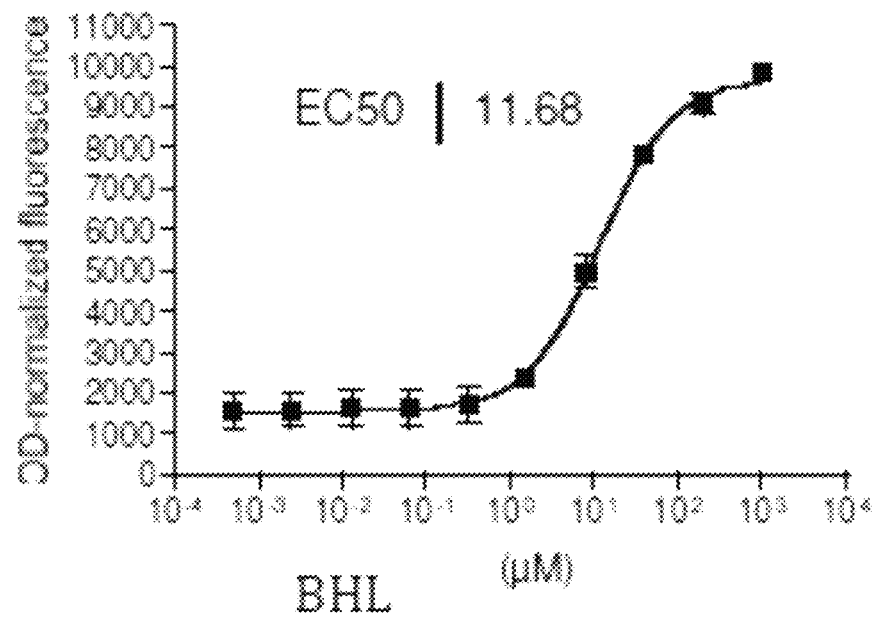
FIGS. 9A-9D illustrate exemplary dose-response curves for RhlR agonism in *P. aeruginosa* by BHL and certain synthetic AHLs. The compound for which he curve was measured is indicated in each figure. Assays were performed using the *P. aeruginosa* PAO-JP2/prhlI-LVAgfp reporter strain. % Activity is defined as the activity of the synthetic AHL relative to maximum possible RhlR activity (i.e., activity effected by BHL at 1 mM). The $EC_{50}$ values for the synthetic compounds were calculated from the region of the dose-response curve that indicated RhlR agonism. $EC_{50}$ values and associated 95% Confidence Intervals (CI; shown on each plot) were calculated using GraphPad Prism. Error bars, SEM of n=3 trials.
Figure 9B:
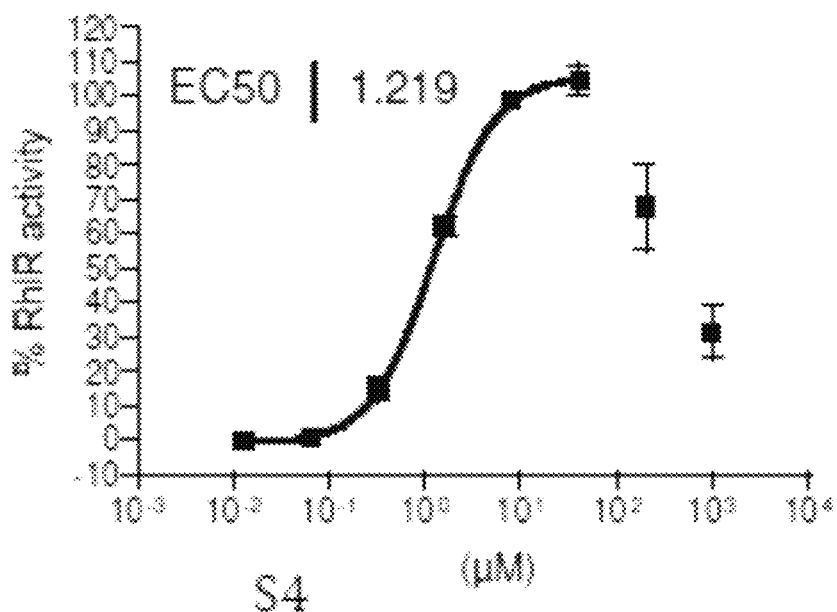
Figure 9C:
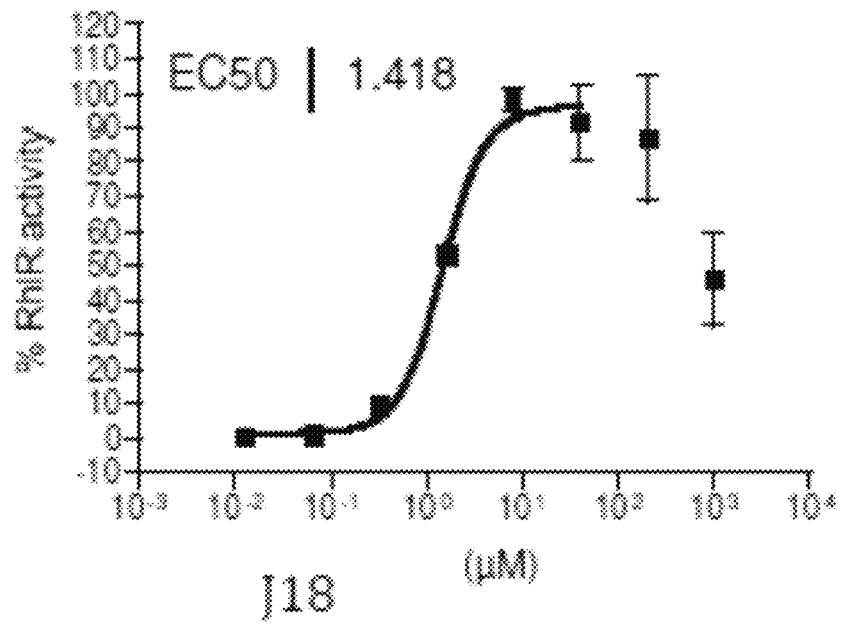
Figure 9D:
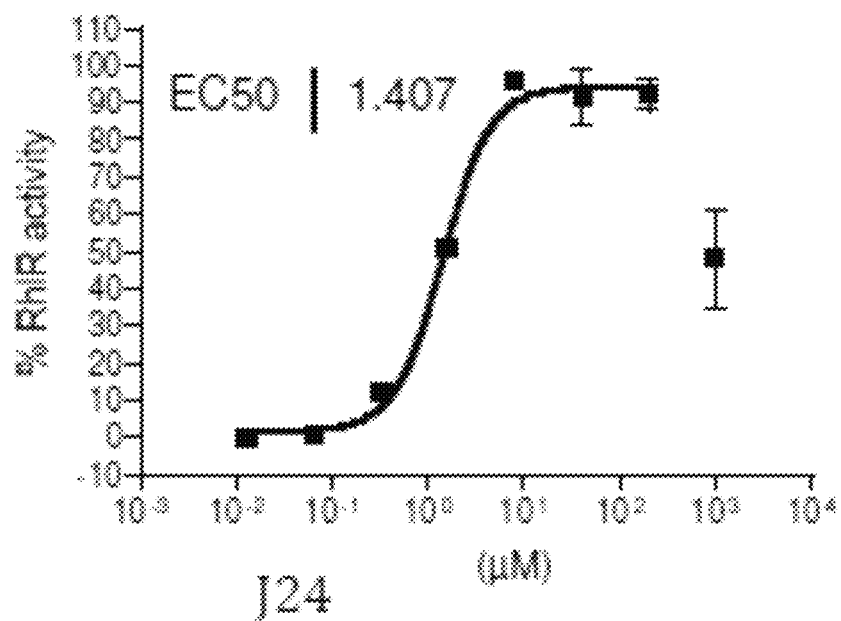

RhlR modulators of the disclosure include compounds AG1-AG18, AT1-AT5 and AR2-AR21 (see FIGS. 5, 6 and 7). In an embodiment, compounds AG1-AG18 are RhlR agonists. In an embodiment, compounds AT1-AT5 are antagonists of RhlR. In an embodiment, compounds AR2-AR21 are antagonists of RhlR.

In specific embodiments herein, RhlR modulators as claimed are other than C3AHL or C5AHL. In specific embodiments herein, RhlR modulators as claimed are other than J3, J5, J6, J7 or J8. In specific embodiments herein, RhlR modulators as claimed are other than J17, J18, J20, or J21. In specific embodiments herein, RhlR modulators as claimed are other than RN3 or RN3OH. In specific embodiments herein, RhlR modulators as claimed are other than RN5, RN6, RN7, or RN8. In specific embodiments herein, RhlR modulators as claimed are other than BHL, OdDHL, D8, S4 or E22.

Certain compounds of the invention exhibit selectivity for agonism or antagonism of RhlR compared to agonism or antagonism of LasR. Certain compounds exhibit selectivity for agonism of RhlR receptor over LasR (See Table 6). Compounds of the formulas here can exhibit at least 2 fold selectivity for agonism of RhlH compared to LasR. More specifically, compounds herein can exhibit 4, 10, 20, 50, 100, 150 or 200 fold or more selectivity for agonism of RhlR over agonism for LasR. Certain compounds exhibit selectivity for antagonism of RhlR receptor over LasR (See Table 7). Compounds of the formulas here can exhibit 1.3 fold or more selectivity for antagonism of RhlH compared to LasR. More specifically, compounds herein can exhibit 5, 10, 20, 50, 70 or 100 fold or more selectivity for antagonism of RhlR over antagonism for LasR.

The disclosure relates to a method for inhibiting quorum sensing in vivo or in vitro of a Gram-negative bacterium employing contacting the bacterium or an environment containing the bacterium with a modulator of RhlR. In specific embodiments, the small molecule modulators of the QS systems herein exclude the native activators of the QS system. In a specific embodiment, inhibiting quorum sensing inhibits virulence. In a specific embodiment, inhibiting quorum sensing inhibits biofilm formation. In a specific embodiment, activity of the modulator of RhlR exhibits a dependence upon the environment of the bacterium. In specific embodiments, the activity of the modulator of RhlR exhibits a dependence upon the levels of nutrients in the environment of the bacterium. In specific embodiments, the activity of the modulators of RhlR exhibits a dependence upon the levels of phosphate in the environment of the bacterium. In specific embodiments, the activity of the modulators of RhlR exhibits a dependence upon the levels of iron in the environment of the bacterium.

In specific embodiments, the Gram-negative bacterium is of the family Pseudomonadacae. In specific embodiments, the Gram-negative bacterium is a species of the genus *Pseudomonas*. In specific embodiments, the Gram-negative bacterium is *Pseudomonas aeruginosa*. In specific embodiments, the *Pseudomonas* species is *P. putida*, or *P. syringae*. In specific embodiments, the Gram-negative bacterium is a species of the genus *Burkholderia*. In specific embodiments, the species of *Burkholderia* is *B. cepacia, B. pseudomallei*, or *B. mallei*.

The disclosure also relates to a method for inhibiting quorum sensing in vivo or in vitro of a Gram-negative bacterium which has an RhlR QS system employing contacting the bacterium or an environment containing the bacterium with a small molecule modulators of RhlR as disclosed herein. In specific embodiments, the small molecule modulators of the RhlR exclude the native activators of QS systems. In a specific embodiment, inhibiting quorum sensing inhibits virulence. In a specific embodiment, inhibiting quorum sensing inhibits biofilm formation in the bacterium. In a specific embodiment, RhlR of the QS systems of the Gram-negative bacterium is mediated in nature by an N-acylhomoserine lactone signal molecule (i.e., the native activator of the QS system is an N-acylhomoserine lactone) and more specifically is mediated in nature by BHL. In specific embodiments, the Gram-negative bacterium is of the family Pseudomonadacae. In specific embodiments, the Gram-negative bacterium is a species of the genus *Pseudomonas*. In specific embodiments, the Gram-negative bacterium is *Pseudomonas aeruginosa*. In specific embodiments, the *Pseudomonas* species is *P. putida*, or *P. syringae*. In specific embodiments, the Gram-negative bacterium is a species of the genus *Burkholderia*. In specific embodiments, the species of *Burkholderia* is *B. cepacia, B. pseudomallei*, or *B. mallei*.

The disclosure provides a method for treatment of an infection of a Gram-negative bacterium by inhibiting virulence in the bacterium employing a combination of two or more modulators each of which modulates a different QS system of the bacterium. In a specific embodiment, the method comprises the step of administering, to an individual in need of treatment for such infection, a combination of two or more small molecule antagonists of a QS system controlling virulence in the bacterium. More specifically, the two or more antagonists include one or more antagonists of one QS system of the bacterium and one or more antagonists of a second QS system of the bacterium. In a specific embodiment, activity of the modulators of one or more of the multiple QS systems of the bacterium exhibits a dependence upon the environment of the bacterium. In specific embodiments, the activity of the modulators of one or more of the multiple QS systems of the bacterium exhibits a dependence upon the levels of nutrients in the environment of the bacterium. In specific embodiments, the activity of the modulators of one or more of the multiple QS systems of the bacterium exhibits a dependence upon the levels of phosphate in the environment of the bacterium. In specific embodiments, the activity of the modulators of one or more of the multiple QS systems of the bacterium exhibits a dependence upon the levels of iron in the environment of the bacterium. In specific embodiments, the Gram-negative bacterium has three or more QS systems each of the systems having a different receptor and more specifically has three or more such QS systems exhibiting interaction among at least two of the systems. In an embodiment, the combination of small molecule modulators is a combination of two or more antagonists of different QS receptors of the QS system. In specific embodiments, the QS system of the bacterium has at least one QS system having a LuxR-type receptor and at least a second QS system having a receptor other than a LuxR-type receptor. In specific embodiments, the QS system of the bacterium has at least two QS systems each having a LuxR-type receptor and at least a third QS system having a receptor other than a LuxR-type receptor. In specific embodiments, the gram-negative bacterium is of the species *Pseudomonas*. In specific embodiments, the gram-negative bacterium is *Pseudomonas aeruginosa*.

In specific embodiments, the disclosure provides a method for treatment of an infection in an animal including a mammal and including a human of a Gram-negative bacterium by inhibiting virulence in the bacterium employing a combination of two or modulators each of which modulates a different QS system of the bacterium. In another specific embodiment, the infection is an infection of a combination of bacteria at least one of which have multiple QS systems. In another specific embodiment, the infection is an infection of a combination of species of bacteria of the genus *Pseudomonas* and *Burkholderia*. In a specific embodiment, the infection is an infection of the bacterium *P. aeruginosa*. In another specific embodiment, the infection is an infection of a combination of bacteria, including *P. aeruginosa*. In another specific embodiment, the infection is an infection of a combination of *P. aeruginosa* and *Burkholderia cepacia*. In specific embodiments, the infection is an infection of the lungs. In an embodiment, the infection is an infection of a burn wound. In an embodiment, the infection is an infection in an immune-compromised individual. In an embodiment, the infection is an infection in an individual with cystic fibrosis. In an embodiment, the infection is an infection in an individual with HIV.

The disclosure in addition provides a virulence inhibiting composition comprising two or more small molecule QS modulators, each of which modulates a different QS system of a selected Gram-negative bacterium. In a specific embodiment, the virulence inhibiting composition is a pharmaceutically acceptable composition. In a specific embodiment, the virulence inhibiting composition comprises the two or more small molecule QS modulators as active ingredients in combination with a pharmaceutically acceptable carrier.

In another aspect, the disclosure relates to certain combinations of Rhl modulators of this disclosure in combination with modulators of Las and/or Pqs which exhibit improved inhibition of virulence in comparison to the respective individual modulators. In specific embodiments, certain combinations of modulators exhibit such improved inhibition in nutritionally depleted (with respect to the bacterium) environments. In specific embodiments, certain combinations of modulators exhibit such improved inhibition in environments depleted in phosphate. In specific embodiments, certain combinations of modulators exhibit such improved inhibition in environments depleted in iron.

The disclosure provides a method of modulating RhlR of a Gram-negative bacterium by contacting the bacterium with one or more compounds of formulas I, II, IIB, III, or IV. More specifically, the method employs compounds of formula II. More specifically, the method employs compounds of formula III. More specifically, the method employs compounds of formula IIB. More specifically, the method employs compounds of formula IV. More specifically the method employs one or more compound designated herein as AG1-AG18, AT1-AT5 or AR2-AR21. More specifically, the method employs compound RN17, RN22, RN 23 or E22 or mixtures thereof. More specifically, the method employs compound RN17, RN22, RN 23 or mixtures thereof. More specifically, the method employs compound RN22, RN 23 or mixtures thereof.

In a specific embodiment of the method, modulating is activating and the modulator is a compound of formula I, II, III or IV where the HG or HGII is cyclopentyl.

Combination of QS modulators with Rhl modulators herein includes chemically different modulators wherein the modulators affect either the Las or Pqs QS systems. In some cases, a given modulator in a combination may affect more than one QS system. In the case where a given modulator affects more than one QS system, the modulator will be designated based on the QS system for which it exhibits the highest level of effect. The effect of a given modulator on a given QS system may depend upon the level of nutrients, the carbon source or other components or conditions (e.g., pH) of the environment of the bacterium, where such environment can, for example, be an in vivo environment infected by the bacterium. Preferably, the combination contains chemically different modulators Rhl with one of a Las modulator or a Pqs modulator. In specific embodiments, the combination of modulators is a combination of one or more antagonist of LasR with one or more antagonist of RhlR herein. In specific embodiments, the combination of modulators is a combination of one or more antagonists of RhlR with one or more antagonist of PqsR. In specific embodiments, the relative molar amounts of the antagonist or the more than one antagonist of LasR and the antagonist or the more than one antagonist of RhlR in the combination ranges from 0.1 to 10. In specific embodiments, the relative molar amounts of the antagonist or the more than one antagonist of LasR and of the antagonist or the more than one antagonist of RhlR in the combination ranges from 0.5 to 5. In specific embodiments, the relative molar amounts of the antagonist or the more than one antagonist of RhlR and the antagonist or the more than one antagonist of PqsR in the combination ranges from 0.1 to 10. In specific embodiments, the relative molar amounts of the antagonist or the more than one antagonist of RhlR and the antagonist or the more than one antagonist of PqsR in the combination ranges from 0.5 to 5.

The disclosure also relates to a method for inhibiting quorum sensing in vivo or in vitro of a Gram-negative bacterium which has a plurality of QS systems employing contacting the bacterium or an environment containing the bacterium with a combination of small molecule modulators of two or more of the QS systems. In specific embodiments, the small molecule modulators of the QS systems exclude the native activators of the OS systems. In a specific embodiment, inhibiting quorum sensing inhibits virulence and the plurality of QS systems together control virulence of the bacterium. In a specific embodiment, inhibiting quorum sensing inhibits biofilm formation and the plurality of QS systems modulate biofilm formation in the bacterium. In a specific embodiment, the QS systems of the Gram-negative bacterium include at least one QS system which is mediated in nature by an N-acylhomoserine lactone signal molecule (i.e., the native activator of the QS system is an N-acylhomoserine lactone). In a specific embodiment, activity of the modulators of one or more of the multiple QS systems of the bacterium exhibits a dependence upon the environment of the bacterium. In specific embodiments, the activity of the modulators of one or more of the multiple QS systems of the bacterium exhibits a dependence upon the levels of nutrients in the environment of the bacterium. In specific embodiments, the activity of the modulators of one or more of the multiple QS systems of the bacterium exhibits a dependence upon the levels of phosphate in the environment of the bacterium. In specific embodiments, the activity of the modulators of one or more of the multiple QS systems of the bacterium exhibits a dependence upon the levels of iron in the environment of the bacterium. In specific embodiments, the Gram-negative bacterium has three or more QS systems each of the systems having a different receptor and more specifically has three or more such QS systems exhibiting interaction among at least two of the systems. In an embodiment, the combination of small molecule modulators is a combination of two or more antagonists of different QS receptors of the QS system. In specific embodiments, the QS system of the bacterium has at least one QS system having a LuxR-type receptor and at least a second QS system having a receptor other than a LuxR-type receptor. In specific embodiments, the QS system of the bacterium has at least two QS systems each having a LuxR-type receptor and at least a third QS system having a receptor other than a LuxR-type receptor. In specific embodiments, the Gram-negative bacterium is of the family Pseudomonadacae. In specific embodiments, the Gram-negative bacterium is a species of the genus *Pseudomonas*. In specific embodiments, the Gram-negative bacterium is *Pseudomonas aeruginosa*. In specific embodiments, the *Pseudomonas* species is *P. putida*, or *P. syringae*. In specific embodiments, the Gram-negative bacterium is a species of the genus *Burkholderia*. In specific embodiments, the species of *Burkholderia* is *B. cepacia, B. pseudomallei*, or *B. mallei*. The disclosure provides a method for treatment of an infection of a Gram-negative bacterium by inhibiting virulence in the bacterium employing a combination of two or modulators each of which modulates a different QS system of the bacterium. In a specific embodiment, the method comprises the step of administering, to an individual in need of treatment for such infection, a combination of two or more small molecule antagonists of a QS system controlling virulence in the bacterium. More specifically, the two or more antagonists include one or more antagonists of one QS system of the bacterium and one or more antagonists of a second QS system of the bacterium. In a specific embodiment, activity of the modulators of one or more of the multiple QS systems of the bacterium exhibits a dependence upon the environment of the bacterium. In specific embodiments, the activity of the modulators of one or more of the multiple QS systems of the bacterium exhibits a dependence upon the levels of nutrients in the environment of the bacterium. In specific embodiments, the activity of the modulators of one or more of the multiple QS systems of the bacterium exhibits a dependence upon the levels of phosphate in the environment of the bacterium. In specific embodiments, the activity of the modulators of one or more of the multiple QS systems of the bacterium exhibits a dependence upon the levels of iron in the environment of the bacterium. In specific embodiments, the Gram-negative bacterium has three or more QS systems each of the systems having a different receptor and more specifically has three or more such QS systems exhibiting interaction among at least two of the systems. In an embodiment, the combination of small molecule modulators is a combination of two or more antagonists of different QS receptors of the QS system. In specific embodiments, the QS system of the bacterium has at least one QS system having a LuxR-type receptor and at least a second QS system having a receptor other than a LuxR-type receptor. In specific embodiments, the QS system of the bacterium has at least two QS systems each having a LuxR-type receptor and at least a third QS system having a receptor other than a LuxR-type receptor. In specific embodiments, the gram-negative bacterium is of the species *Pseudomonas*. In specific embodiments, the gram-negative bacterium is *Pseudomonas aeruginosa*.

In specific embodiments, the disclosure provides a method for treatment of an infection in an animal including a mammal and including a human of a Gram-negative bacterium by inhibiting virulence in the bacterium employing a combination of two or modulators each of which modulates a different QS system of the bacterium. In another specific embodiment, the infection is an infection of a combination of bacteria at least one of which have multiple QS systems. In another specific embodiment, the infection is an infection of a combination of species of bacteria of the genus *Pseudomonas* and *Burkholderia*. In a specific embodiment, the infection is an infection of the bacterium *P. aeruginosa*. In another specific embodiment, the infection is an infection of a combination of bacteria, including *P. aeruginosa*. In another specific embodiment, the infection is an infection of a combination of *P. aeruginosa* and *Burkholderia cepacia*. In specific embodiments, the infection is an infection of the lungs. In an embodiment, the infection is an infection of a burn wound. In an embodiment, the infection is an infection in an immune-compromised individual. In an embodiment, the infection is an infection in an individual with cystic fibrosis. In an embodiment, the infection is an infection in an individual with HIV.

The disclosure in addition provides a virulence inhibiting composition comprising two or more small molecule QS modulators, each of which modulates a different QS system of a selected Gram-negative bacterium. In a specific embodiment, the virulence inhibiting composition is a pharmaceutically acceptable composition. In a specific embodiment, the virulence inhibiting composition comprises the two or more small molecule QS modulators as active ingredients in combination with a pharmaceutically acceptable carrier.

Further aspects and embodiments of the disclosure will be apparent to one of ordinary skill in the art on consideration of the drawings and examples.

Bacteria can have multiple quorum sensing systems which are distinct. Distinct quorum sensing systems are defined by having distinct proteins involved in regulation of quorum sensing and distinct molecules which activate a given quorum sensing system. A compound which is a modulator of a selected quorum sensing system in a given bacterium (e.g., LasR, RhlR or PqsR in *Pseudomonas*) may exhibit some level of activity as a modulator of a different quorum sensing system in that bacterium. For example, a given modulator, particularly a synthetic non-native small molecule may acts as an inhibitor of RhlR and an agonist of LasR. More specifically, a compound which is an inhibitor of one quorum sensing system may also inhibit other quorum sensing systems in the same bacterium. The relative amount of inhibition (or activation) that a given compound exhibits for each quorum sensing system in a bacterium can be assessed, for example, as demonstrated in Welsh et al. (2015) J. Am. Chem. Soc. 137:1510-1519 Moore et al. 2015 and Eibergen et al. (2015) ChemBioChem, 16:2348-2356 by determining the relative levels of antagonism or agonism exhibited by a given compound with respect to different quorum sensing systems present in a bacterium. The text and supplemental information for each of these references is provided in Appendices to this application at least for assay methods for determining relative levels of antagonism and agonism of a given compound for a given quorum sensing system.

The terms "inhibitor" and "antagonist" are used interchangeably herein. The terms "activator" and "agonist" are used interchangeably herein.

In the combinations of quorum sensing modulators of the present disclosure, a given compound is defined as an antagonist or agonist of a given quorum sensing system based on the quorum sensing system for which it exhibits the highest level of antagonism or agonism in a given bacterium. For use in the methods of this disclosure, modulators which exhibit selective inhibition (or selective agonism) of a given quorum sensing system in a given bacterium are preferred. A selective inhibitor (antagonist) of a quorum sensing system, exhibits 60% or higher antagonism of the quorum sensing system for which it is selective and exhibits 40% or less antagonism of other quorum sensing systems in the bacterium. A more preferred selective inhibitor of a given quorum sensing system exhibits less than 40% agonism of another quorum sensing system in the bacterium.

A more preferred selective inhibitor of a given quorum sensing system exhibits less than 40% antagonism of a quorum sensing system other than the quorum sensing system for which it is selective in the bacterium. A more preferred selective inhibitor of a given quorum sensing system exhibits less than 30% antagonism of a quorum sensing system other than the quorum sensing system for which it is selective in the bacterium. A more preferred selective inhibitor of a given quorum sensing system exhibits less than 20% antagonism of a quorum sensing system other than the quorum sensing system for which it is selective in the bacterium. A more preferred selective inhibitor of a given quorum sensing system exhibits less than 10% antagonism of a quorum sensing system other than the quorum sensing system for which it is selective in the bacterium.

A more preferred selective inhibitor of a given quorum sensing system exhibits less than 30% agonism of another quorum sensing system in the bacterium. A more preferred selective inhibitor of a given quorum sensing system exhibits less than 20% agonism of another quorum sensing system in the bacterium. A more preferred selective inhibitor of a given quorum sensing system exhibits less than 10% agonism of another quorum sensing system in the bacterium. A more preferred selective inhibitor of a given quorum sensing system exhibits equal to or less than 5% agonism of another quorum sensing system in the bacterium.

In specific embodiments, a more preferred selective inhibitor exhibits 60% or higher antagonism of the quorum sensing system for which it is selective, exhibits 30% or less antagonism of other quorum sensing systems in the bacterium and exhibits less than 30% agonism of other quorum sensing systems in the bacterium. In specific embodiments, a more preferred selective inhibitor exhibits 60% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 10% or less antagonism of other quorum sensing systems in the bacterium and exhibits less than 10% agonism of another quorum sensing system in the bacterium.

In specific embodiments, a more preferred selective inhibitor exhibits 70% or higher antagonism of the quorum sensing system for which it is selective, exhibits 40% or less antagonism of other quorum sensing systems in the bacterium and exhibits less than 30% agonism of other quorum sensing systems in the bacterium. In specific embodiments, a more preferred selective inhibitor exhibits 70% or higher antagonism of the quorum sensing system for which it is selective, exhibits 30% or less antagonism of other quorum sensing systems in the bacterium and exhibits less than 30% agonism of another quorum sensing system in the bacterium. In specific embodiments, a more preferred selective inhibitor exhibits 70% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 60% or higher antagonism of the quorum sensing system for which it is selective, exhibits 10% or less antagonism of other quorum sensing systems in the bacterium and exhibits less than 10% agonism of another quorum sensing system in the bacterium.

In specific embodiments, a more preferred selective inhibitor exhibits 80% or higher antagonism of the quorum sensing system for which it is selective, exhibits 40% or less antagonism of other quorum sensing systems in the bacterium and exhibits less than 30% agonism of another quorum sensing system in the bacterium. In specific embodiments, a more preferred selective inhibitor exhibits 80% or higher antagonism of the quorum sensing system for which it is selective, exhibits 30% or less antagonism of other quorum sensing systems in the bacterium and exhibits less than 30% agonism of another quorum sensing system in the bacterium. In specific embodiments, a more preferred selective inhibitor exhibits 80% or higher antagonism of the quorum sensing system for which it is selective, exhibits 20% or less antagonism of other quorum sensing systems in the bacterium and exhibits less than 20% agonism of another quorum sensing system in the bacterium. In specific embodiments, a more preferred selective inhibitor exhibits 80% or higher antagonism of the quorum sensing system for which it is selective, exhibits 10% or less antagonism of other quorum sensing systems in the bacterium and exhibits less than 10% agonism of another quorum sensing system in the bacterium.

In specific embodiments of the above, the selective inhibitor is a LasR inhibitor which is selective with respect to inhibition of RhlR and PqsR and is selective with respect to activation (agonism) of RhlR and PqsR. In specific embodiments of the above, the selective inhibitor is a RhlR inhibitor which is selective with respect to inhibition of LasR and PqsR and is selective with respect to activation (agonism) of LasR and PqsR. In specific embodiments of the above, the selective inhibitor is a PqsR inhibitor which is selective with respect to inhibition of LasR and RhlR and is selective with respect to activation (agonism) of LasR and RhlR.

In specific embodiments, inhibitors of LasR, RhlR and PqsR are employed in combination of the disclosure. In specific embodiments, selective inhibitors of LasR, RhlR and PqsR are employed in combination of the disclosure.

U.S. provisional application 62/294,921, filed Feb. 12, 2016, and U.S. application Ser. No. 15/431,295, filed Feb. 13, 2017, are each incorporated by reference herein for descriptions of exemplary LasR and PqsR modulators which may be used in combination with RhlR modulators of this disclosure.

The Rhl and Pqs systems work in tandem to drive virulence factor production in nutrient limiting conditions, while Las is only a minor contributor under such nutrient limiting conditions. LasR inhibitors display reduced activity in low iron and phosphate environments, and as a result, cocktails (mixtures) of RhlR and PqsR inhibitors can attenuate virulence in a broad range of conditions where Las antagonists are inactive. The activity trends uncovered herein are also predictive of compound activity in infection relevant environments, including the CF airway, which are nutrient limiting condition for the bacterium. Thus, the present work indicates unique roles for the *P. aeruginosa* QS systems in tailoring virulence factor production to the environment, and provides novel insights into pathways that, with further development, could potentially be targeted to fight this pathogen.

The terms "nutrient limiting" or "nutrient depleted" refer to bacterial environments that are limited or depleted with respect to the nutritional needs of a given bacterium such that growth of the bacterium is limited under such conditions. Certain quorum sensing systems are sensitive to such "nutrient limiting" or "nutrient depleted" condition such that the systems are modulated in response to such limitation or depletion. The present work investigates quorum sensing inhibition and activation and the interaction of quorum sensing systems in such depleted or limited environments. Such limited or depleted environments ca, for example, be bacterial infection sites, such as the CF airway, a burn or other wound site, the intestine or other in vivo site after surgery. Nutrient limitation or depletion in an in vivo environment can affect virulence of the bacteria in that environment and can affect the extent or virulence of a given infection. The term depleted and limited for a given nutrient are used relative to the level of that nutrient that supports unlimited growth of the bacterium or that is sufficiently high that a given quorum sensing system is not affected by the level of nutrient present. The amount of a given nutrient that results in such growth limitation or quorum sensing modulation will depend on the bacterium and may also depend upon other nutrients in the environment. One of ordinary skill in the art can determine if a given environment is depleted or limiting for a given bacterium without resort to undue experimentation using methods that are known in the art.

The RhlR modulators of this disclosure can be employed in any in vivo or in vitro application for inhibition of virulence of Gram-negative bacteria, alone or in combination with other QS modulators. Contact or administration of the modulators or combinations with other QS modulators can be achieved by various means known in the art by combined or separate contact or combined or separate administration of component compounds of the combinations. Each component of a combination can be formulated separately or the combination of components can be formulated together.

Geske et al. 2007a[43], Geske et al. 2007b[49], Geske et al. 2008a[44] and Geske et al. 2008b[50] are each incorporated by reference herein in its entirety to provide comparisons of QS activity as agonists or antagonists of compounds therein to compounds herein.

The disclosure also provides a method for treating infections of Gram-negative bacteria in an individual in need of such treatment wherein a therapeutically effective amount of one or more RhlR modulators of this disclosure of formula I, II, III or IV herein or a pharmaceutically acceptable salt thereof are administered to said individual. As described herein above, combinations of the modulators of this disclosure can be combined in such application with modulators of LasR and/or PqsR.

The disclosure also provides therapeutic compositions for treating infections of Gram-negative bacteria comprising a therapeutically effective amount of an RhlR modulator of this disclosure of formulas herein or a pharmaceutically acceptable salt of the compounds herein and a pharmaceutically acceptable carrier. In a specific embodiment, such therapeutic compositions comprise at least two quorum sensing compounds of formulas herein or a pharmaceutically acceptable salt thereof.

The disclosure also provides methods for making a medicament for treatment of a bacterial infection, particularly of a Gram-negative bacterium, and more particularly of a strain of *Pseudomonas* or a strain of *Burkholderia*, in which one or more RhlR modulators of the disclosure, particularly which are which are quorum sensing inhibitors, and which are particularly selective quorum sensing inhibitors. In an embodiment, combinations of modulators, including inhibitors of different quorum sensing systems in the bacterium are combined to provide for enhanced inhibition. Such medicaments can further include a pharmaceutically acceptable carrier or excipient as are known in the art.

In an additional embodiment, the disclosure provides one or more RhlR modulators or combinations thereof with other QS modulators and methods employing the same for reducing bacterial virulence and increasing susceptibility of quorum sensing bacterial to biocides and/or antibiotics.

For methods of inhibiting virulence or treating infections herein, one or more compounds (or salts thereof) are administered to a patient or applied to an environment in an amount effective for inhibition of a given quorum sensing system. Generally an effective amount will be dependent upon the bacterium and the environment of the bacterium. In an embodiment for inhibiting a given bacterium in a given environment, the effective amount of a given compound is equal to or greater than the $IC_{50}$ of that compound for a given quorum sensing system. In an embodiment for administration to a mammal, the effective amount of a given compound for inhibition ranges from the $IC_{50}$ or $EC_{50}$ of the compound for inhibition to less than the toxicity level of the compound for mammalian cells. As defined herein, "contacting" means that a compound of the present disclosure is provided such that it is capable of making physical contact with another element, such as a microorganism, a microbial culture, a biofilm, or a substrate or other environment of a bacterium. In another embodiment, the term "contacting" means that a compound of the present disclosure is introduced into an individual receiving treatment, and the compound is allowed to come in contact in vivo. The term "administering" is also used for providing a compound or pharmaceutical composition to an individual in need of treatment. Various administration methods can be employed as will be appreciated by one of ordinary skill in the art.

The term "effective amount" is used generically herein to refer to the amount of a given compound or in case of a combination of compounds the combined amount of mixed components that provides a measurable effect for a listed function. In certain aspects of the disclosure, the effective amount is for treating an infection (see however, the more specific therapeutically effective amount below). In certain embodiments, the effective amount is for inhibition of virulence. In certain embodiments, the effective amount is for inhibition growth of a bacterium. One or more compounds herein or combinations thereof with other QS modulators, in certain embodiments, can inhibit growth or establishment of a biofilm. One or more compounds herein or combinations thereof with other QS modulators, in certain embodiments, can disperse an already formed biofilm.

For example, in certain aspects of the disclosure, a compound of the disclosure is contacted with an element (a substrate, a surface a tool an instrument or the like) in order to prevent formation of or disrupt a biofilm and in this case, the effective amount or combined effective amount of the compound or compounds is that amount that shows a measurable disruption of a biofilm. The effective amount will vary dependent upon the stated function, the environment or element being contacted, the organism forming the biofilm or which is to be contacted, the state of development of the biofilm, among other conditions of the use of the compound. It will be understood by one of ordinary skill in the art, that for a given application, the effective amount can be determined by application of routine experimentation and without undue experimentation by methods that are described herein or that are known in the art.

The term "therapeutically effective amount" is used generically herein to refer to the amount of a given compound or in case of a combination (the individual amount of components or the combined amount of a mixture components when administered to the individual (including a human, or non-human animal) that provides a measurable therapeutic effect for a listed disease, disorder or condition to at least partially ameliorate a symptom of such disease, disorder or condition. The present disclosure provides methods of treating disorders, diseases conditions and symptoms in a human or non-human animal and particularly in a human, by administering to an individual in need of treatment or prophylaxis, a therapeutically effective amount of one or more compounds of this disclosure to the individual in need thereof. The result of treatment can be partially or completely alleviating, inhibiting, preventing, ameliorating and/or relieving the disorder, condition or one or more symptoms thereof. As is understood in the art, the therapeutically effective amount of a given compound will depend at least in part upon, the mode of administration, any carrier or vehicle (e.g., solution, emulsion, etc.) employed, the extent of damage and the specific individual (human or non-human) to whom the compound is to be administered (age, weight, condition, sex, etc.). The dosage requirements needed to achieve the "therapeutically effective amount" vary with the particular compositions employed, the route of administration, the severity of the symptoms presented and the particular individual being treated. Based on the results obtained in standard pharmacological test procedures, projected daily dosages of active compound can be determined as is understood in the art.

Administration is intended to encompass administration of a compound (or combination of compounds as discussed herein), pharmaceutically acceptable salt, solvate or ester thereof alone or in a pharmaceutically acceptable carrier thereof or administration of a prodrug derivative or analog of a compound of this disclosure which will form an equivalent amount of the active compound or substance within the body. An individual in need of treatment or prophylaxis includes those who have been diagnosed to have a given disorder or condition and to those who are suspected, for example, as a consequence of the display of certain symptoms, of having such disorders or conditions.

Compounds and combinations of compounds of this disclosure can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage can vary within wide limits and as is understood in the art will have to be adjusted to the individual requirements in each particular case. By way of general guidance, the daily oral dosage can vary from about 0.01 mg to 1000 mg, 0.1 mg to 100 mg, or 10 mg to 500 mg per day of a compound of formulas herein or of the corresponding amount of a pharmaceutically acceptable salt thereof. The daily dose may be administered as single dose or in divided doses and, in addition, the upper limit can also be exceeded when this is found to be indicated.

Any suitable form of administration can be employed in the methods herein. The compounds of this disclosure can, for example, be administered in oral dosage forms including tablets, capsules, pills, powders, granules, elixirs, tinctures, suspensions, syrups and emulsions. Oral dosage forms may include sustained release or timed release formulations. The compounds of this disclosure may also be administered topically, intravenously, intraperitoneally, subcutaneously, or intramuscularly, all using dosage forms well known to those of ordinary skill in the pharmaceutical arts. Topical application can include those in which the biofilm-inhibitory compound is formulated in a hydrogel or encapsulated in microspheres or nanospheres, for example.

Compounds and combinations of compounds of this disclosure can also be administered in intranasal form by topical use of suitable intranasal vehicles. For intranasal or intrabronchial inhalation or insulation, the compounds of this disclosure may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

The compounds and combinations of compounds of this disclosure can also be administered to the eye, preferably as a topical ophthalmic formulation. The compounds and combinations of compounds of this disclosure can also be combined with a preservative and an appropriate vehicle such as mineral oil or liquid lanolin to provide an ophthalmic ointment. The compounds and combinations of compounds of this disclosure may be administered rectally or vaginally in the form of a conventional suppository. The compounds and combinations of compounds of this disclosure may also be administered transdermally through the use of a transdermal patch containing the active compound and a carrier that is inert to the active compound, is non-toxic to the skin, and allows delivery of the agent for systemic absorption into the blood stream via the skin.

The compounds and combinations of compounds of the disclosure may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this disclosure comprise one or more compounds of any of formula I, II, III or IV in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety.

The disclosure also encompasses method for making a medicament employing a combination of two or more compounds of this disclosure which exhibit a combined therapeutic effect.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

Compounds of the disclosure and of formulas I, II, III or IV include pharmaceutically acceptable salts, if any, of various compounds. The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. Compounds herein may also be present in the form of zwitterions.

Compounds of the disclosure can be in the form of salts which in specific embodiments are non-toxic and more specifically pharmaceutically-acceptable. Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

Compounds of the disclosure can have prodrug forms. Prodrugs of the compounds of the disclosure are useful in the methods of this disclosure. Any compound that will be converted in vivo to provide a biologically, pharmaceutically or therapeutically active form of a compound of the disclosure is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The disclosure expressly includes pharmaceutically usable solvates of compounds according to formulas herein. The compounds can be solvated, e.g. hydrated. The solvation can occur in the course of the manufacturing process or can take place, e.g. as a consequence of hygroscopic properties of an initially anhydrous compound of formulas herein (hydration).

Well-known methods for assessment of drugability can be used to further assess active compounds of the disclosure for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, Experimental and computational approaches to estimate solubility and permeability in drug discovery and development settings, Adv. Drug Del. Rev., 2001, 46, 3-26 and Arup K. Ghose, Vellarkad N. Viswanadhan, and John J. Wendoloski, A Knowledge-Based Approach in Designing Combinatorial or Medicinal Chemistry Libraries for Drug Discovery, J. Combin. Chem., 1999, 1, 55-68.)

In general a preferred drug for oral administration exhibits no more than one violation of the following rules:
(1) Not more than 5 hydrogen bond donors (e.g., nitrogen or oxygen atoms with one or more hydrogens);
(2) Not more than 10 hydrogen bond acceptors (e.g., nitrogen or oxygen atoms);
(3) Molecular weight under 500 g/mol and more preferably between 160 and 480; and
(4) log P less than 5 and more preferably between −0.4 to +5.6 and yet more preferably −1<log P<2.

Compounds of this disclosure preferred for therapeutic application include those that do not violate one or more of 1-4 above.

Compounds of this disclosure preferred for therapeutic application include those having log P less than 5 and more preferably between −0.4 to +5.6 and yet more preferably −1<log P<2.

The compounds of this disclosure may contain one or more chiral centers. Accordingly, this disclosure is intended to include racemic mixtures, diastereomers, enantiomers and mixture enriched in one or more stereoisomer. The scope of the disclosure as described and claimed encompasses the racemic forms of the compounds as well as the individual enantiomers and non-racemic mixtures thereof.

It is understood that this disclosure is not limited to the particular methodology, protocols, cell lines, and reagents described, as these may vary. It is also to be understood that the terminology used herein is for the purpose of describing particular embodiments only, and is not intended to limit the scope of the present disclosure which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

As used herein, the term "treating" includes preventative as well as disorder remittent treatment. In an embodiment, treating herein includes treatment other than prevention. As used herein, the terms "reducing", "suppressing" and "inhibiting" have their commonly understood meaning of lessening or decreasing.

In certain embodiments, the present disclosure encompasses administering the compounds useful in the present disclosure to a patient or individual. A "patient" or "individual", used equivalently herein, refers to an animal. In particular, an animal refers to a mammal, preferably a human. The patient either: (1) has (is diagnosed to have or is believed to have) a condition remediable or treatable by administration of a compound of the disclosure; or (2) is susceptible to a condition that is preventable by administering a compound of this disclosure.

Additional embodiments of the disclosure include the following.

In an embodiment, the present disclosure provides a surface coating or polymer having incorporated therein a combination of compounds of the present disclosure. The amount of compounds or polymer in the surface coating is that sufficient to provide antifouling effect or provide for bacterial inhibition. In an embodiment, the compounds or combinations thereof of the disclosure are useful as an antifouling agent or surface sterilizing agent. In specific embodiments, the compounds of this disclosure exhibit no substantial antimicrobial effect. Compounds of the disclosure are further useful in a medical, scientific, and/or biological application.

In one aspect, the disclosure provides a composition comprising one, two or more compounds of the disclosure and a carrier or diluent. In a preferred embodiment, the carrier or diluent comprises a liquid. Such a liquid may comprises an aqueous solvent or a non-aqueous solvent. An exemplary solvent comprises one or more organic solvents. The carrier or diluent may also comprise an ionic liquid. In an embodiment of this aspect, the composition comprises an organic or inorganic polymeric substance. The polymeric substance may comprise one or more compounds of the present disclosure, admixed with a polymer, bound to a polymer, or adsorbed on to a polymer. In an exemplary embodiment of this aspect, the composition is in the form of a solution or suspension of said at least one compounds of the disclosure, preferably in an aerosol or powder formulation.

In an embodiment, the composition comprising one or more RhlR modulators is formulated as a disinfectant or cleaning formulation. In another embodiment, the composition is in the form of a powder, a solution, a suspension, a dispersion, an emulsion, or a gel. In an exemplary embodiment, the composition is in the form of a pharmaceutical composition comprising a pharmaceutically acceptable carrier, diluent, and/or excipient and one or more compounds of the present disclosure. The composition may be in a form suitable for parenteral or non-parenteral administration. A preferred composition may be formulated for topical, intradermal, intramuscular, intraperitoneal, intravenous, subcutaneous, intranasal, epidural, ophthalmic, or oral administration. In an embodiment of this aspect the composition is formulated for administration by infusion or bolus injection, absorption through epithelial or mucocutaneous linings and may be administered together with other biologically active agents. In an embodiment, the composition may further be formulated for use in an inhaler or nebulizer.

In another aspect, the present disclosure provides a method of treating an infection in a human or animal, the method comprising administration to the individual (human or animal) of a therapeutically effective amount of one or more compounds of the disclosure. In an embodiment, the treatment is therapeutic or prophylactic.

In a related embodiment, the present disclosure provides a method of treating an infection or condition in an individual that is characterized by biofilm formation, the method comprising administering one or more compounds of the disclosure. In an embodiment, the condition is cystic fibrosis. In an embodiment, the condition is dental caries, periodonitis, otitis media, muscular skeletal infections, necrotizing fasciitis, biliary tract infection, osteomyelitis, bacterial prostatitis, native valve endocarditis, cystic fibrosis pneumonia, or meloidosis. In an embodiment, the condition is a nosocomial infection; preferably the infection is ICU pneumonia or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, orthopedic devices, or penile prostheses. In an embodiment, the infection is a skin infection, a burn infection, or a wound infection. According to this aspect, the individual may preferably be an immune-compromised individual.

In specific embodiments herein, contacting is achieved by release of one or more inhibitory compounds of the disclosure from a polymer film, multilayer film, hydrogel, or coating that contains the one or more biofilm-inhibitory compounds of the disclosure. In general, any art-known type of film, hydrogel or coating can be employed for containing and thereafter releasing one or more biofilm-inhibitory compounds of the disclosure. It will be appreciated that the film or coating (e.g., polymer) must be chemically compatible with and not inactivate the inhibitory compound. In other specific embodiments, contacting is achieved by encapsulation of and later release of one or more inhibitory compounds of the disclosure into the environment to be. Encapsulation can be by any art known method and can be in the form of micro- or nanoencapsulation.

Methods of this disclosure can be implemented employing thin films, multilayers, coatings, hydrogels, encapsulation and related delivery methods where the biofilm-inhibitory compounds are loaded in the films, coatings, hydrogels or are encapsulated for delivery over time to an environment having existing biofilms or which is susceptible to biofilm formation. Encapsulation can be in various forms including among others microspheres or nanospheres. The use of such delivery methods can provide for release of one or more biofilm-inhibitory compounds over time extending from days to week to months dependent upon the methods and specific materials employed. In specific embodiments, a surface is protected from biofilm formation by application of a thin film, a multilayer, a coating or the like to at least a portion of the surface. In a related embodiment, surfaces are protected from biofilm formation or cleaned of biofilms by application of a thin film, a multilayer, a coating or the like to a surface in the vicinity of the surfaces to be protected in order to release an effective amount of biofilm-inhibitory compound of the disclosure into the vicinity of the surfaces to be protected. In specific embodiments, films, multilayers, coatings or encapsulation methods provide a level of the biofilm-inhibitory compound to the surface or to the vicinity of a surface to be protected which ranges from the $IC_{50}$ of the compound for biofilm inhibition to less than the toxicity level of the compound for mammalian cells. In specific embodiments, the concentration of biofilm-inhibitory compounds provided by such films, multilayers, coatings or encapsulation methods to the environment to be protected ranges from the IC50 of the compound to less than 0.25 mM. More specifically, the concentration provided to the environment to be protected ranges from 10-100 micromolar.

In specific embodiments, films, multilayers and coatings generated using one or more polymers and which contain from about 0.001 to 1 mg or more preferably from 0.01 to 1 mg/gram of biofilm-inhibitory compound/gram of polymer are useful for biofilm inhibition or dispersion. In a specific embodiment, biofilm-inhibitory compounds of the disclosure are provided to a surface or a portion of a surface in film formed from a poly(lactide-co-glycolide).

The present disclosure further provides a method for treating or preventing biofilm formation on a surface, the method comprising contacting said surface with combined compounds of the disclosure in an amount effective for affecting biofilm formation of the present disclosure. In an embodiment, the surface is a non-biological surface. In an embodiment, the surface is a natural surface. In an embodiment, the surface is a surface of a plant, seed, wood, fiber or hair. In an embodiment, the surface is a biological surface; preferably the surface is a surface of a tissue, membrane, or skin. In an embodiment, the surface is a hard surface; preferably the surface comprises a metal, an organic polymer, an inorganic polymer, a natural elastomer, a synthetic elastomer, glass, wood, paper, concrete, rock, marble, gypsum, or ceramic. In an embodiment, the said surface is coated or wherein the surface is a coating; in a preferred embodiment, the coating comprises enamel, varnish, or paint.

In an embodiment of this aspect, the surface is a soft surface, and may be the surface of a fiber comprising a yarn, a textile, a vegetable fiber, or rock wool. In another embodiment, the surface is a porous surface. In an embodiment, the surface is a surface of process equipment or components of cooling equipment. In a preferred embodiment, the process equipment is or is a component of a cooling tower, a water treatment plant, a dairy processing plant, a food processing plant, a chemical process plant, or a pharmaceutical process plant. In a preferred embodiment the surface is that of a filter or a membrane filter.

In an embodiment of this aspect, the surface is a surface of a toilet bowl, a bathtub, a drain, a high-chair, a counter top, a vegetable, a meat processing room, a butcher shop, food preparation areas, an air duct, an air-conditioner, a carpet, paper or woven product treatment, a diaper, personal hygiene products and a washing machine. In another embodiment, the surface is an industrial surface or a medical surface; preferably the surface is a surface in a hospital, a veterinary hospital, a mortuary, or a funeral parlor.

In another aspect, the RhlR modulators of the disclosure are useful as a component of a dentifrice, a mouthwash, or a composition for the treatment of dental caries; for treatment of acne; or for cleaning and/or disinfecting contact lenses. The compounds of the disclosure are further useful for incorporation into the surface of a medical device or an implant device. Preferably the implant device is an artificial heart valve, hip joint, an indwelling catheter, pacemaker, or surgical pin. The compounds of the disclosure are further useful as an antifouling coating. The disclosure further provides an optical lens, wherein at least a part of a surface of the lens is associated with one or more compounds of the disclosure. Preferably, the optical lens is a contact lens.

In another aspect, the disclosure provides a biofilm removing or inhibiting composition comprising one or more compounds of the disclosure in an amount effective for removing or inhibiting biofilm formation and a vehicle or carrier, wherein the amount of the mixture is effective to remove or disrupt a bacterial biofilm or inhibit normal biofilm formation. An embodiment of this aspect may further comprise a surfactant selected from the group consisting of an anionic surfactant, a nonionic surfactant, an amphoteric surfactant, a biological surfactant, and any combination of these; or a compound selected from the group consisting of a biocide, a fungicide, an antibiotic, and any combination of these.

The term antibacterial agent refers generically to chemical species that exhibit bacteriostatic or bactericidal effect. Of particular interest are antibacterial agents effective against one or more Gram-negative bacteria and particularly those that are effective against *Pseudomonas*, and more particularly against *P. aeruginosa*. Antibacterial agents include disinfectants such as chlorine, bromine and chlorine dioxide and quaternary ammonium compounds as well as antibiotics. A variety of antibiotics are known in the art and one of ordinary skill in the art can select one or more antibiotics appropriate for use against a given species or strain of Gram-negative bacteria. Antibiotics useful in the method of this disclosure include among others gentamicin, kanamycin neomycin, streptomycin and other aminoglycoside antibiotics which are of particular use against *P. aeruginosa* infections.

Additional exemplary classes of antibiotics include among others Penicillins, Cephalosporins, Carbapenems, Tetracyclines, Macrolides, Quinolones and Sulfonamides. One of ordinary skill in the art can readily chose amongst known antibiotics of these classes for use in the methods herein.

In another embodiment, the disclosure provides a film, multilayer film, hydrogel or coating, for application to a surface or in the vicinity of a surface, containing a combination of compounds of the disclosure to inhibit or prevent biofilm formation on the surface.

In another embodiment, the disclosure provides a combination of compounds o the disclosure, such as a pharmaceutical composition, a disinfectant composition, an encapsulated formulation, a coating for application to a surface or similar composition. Such compositions are useful to regulate a symbiotic behavior of quorum sensing bacteria. This symbiotic behavior may be biofilm formation. Other symbiotic behaviors that may be regulated include swarming, motility, sporulation, conjugation, bioluminescence and/or production of pigments, antibiotics and enzymes. Quorum sensing molecules of the formulas of this disclosure may in one embodiment inhibit, decrease or attenuate a behavior of quorum sensing bacteria, particularly Gram-negative quorum sensing bacteria, particularly Pseudomonas and more particularly P. aeruginosa.

In an embodiment, a coating containing one or more RhlR modulators can be applied to a variety of surfaces using methods that are well-known in the art. The coating may be in the form of a film, including a multi-layer film, or a gel, particularly a hydrogel, comprising one or more of the compounds of this disclosure. Coatings can be employed in medical and non-medical applications. Specific applications include coated medical devices (e.g., stents, catheters, and feminine hygiene products) and industrial coatings (e.g., ship hulls and heat exchangers). The coating may be applied to the surfaces of interest using a variety of known methods. In specific embodiments, the coating loaded with one or more inhibitory compounds of this disclosure is formed by solvent casting. In other embodiments, the loaded coating is formed by spin coating. In other embodiments, the loaded coating is formed by dip coating. In other embodiments, one or more of solvent casting, spin coating or dip coating is employed to form surfaces carrying inhibitory loaded films of this disclosure.

In an embodiment, inhibitory compounds and combinations thereof the disclosure can be encapsulated in thin bulk films of conventional polymers, such as PLA, or PLGA by known methods such as dip-coating or solvent casting. Such films can be applied to surfaces as desired where the encapsulated inhibitor is released to inhibit or prevent biofilm formation on the surface. In an embodiment, biofilm inhibitors of this disclosure can be loaded into nanostructured polymer multilayers, for example, PEMs and other cross-linked multilayers, for example, using a layer-by-layer approach. Multilayers can be applied to or formed on surfaces to release biofilm inhibitor to inhibit or prevent biofilm formation on the surface. Sustained release of the inhibitors can be obtained using such methods. Methods useful for making films or coatings including multilayer films are described, for example, in Lynn and co-workers: Adv. Mater. 2007; Biomacromolecules 2009; Adv. Mater. 2010; Langmuir 2010; ACS App. Mater. Inter. 2010; Langmuir 2010; Chem. Mater. 2010; J. Mater. Chem. 2011; Adv. Biomat. 2011; Biomacromolecules 2011 and in U.S. Pat. Nos. 7,883,720; 8,071,210 and published US applications US20080286345 and US20090105375, each of which is incorporated by reference herein for descriptions of methods and materials, particularly polymers and co-polymers, useful for forming films, multilayer films and the like. It will be appreciated that combinations of the disclosure can be individually encapsulated or otherwise formulated and such individual encapsulated compounds or other individual formulations can be combined in an application, contacting step or administration step to achieve the desired combined effect that is discussed herein.

More generally for contact or administration herein, one or more compounds can applied to a bacterium, an environment of a bacterium or administered to a patient simultaneously or separately, at the same site at the same time or a different time, in the same type of formulation or dosage form or in a different type of formulation or a different dosage form.

In specific embodiments, the disclosure provides films, coatings or hydrogels containing one of or a combination of the inhibitory compound of the disclosure. In specific embodiments, films, coatings and/or hydrogels or the like of this disclosure provide a concentration of an inhibitory compound into the environment to be protected (e.g., a surface) that is effective for inhibiting virulence. In an embodiment, such coatings, inhibit formation of a biofilm or disperse an already formed biofilm. Such coatings can provide for some level of decrease of bacteria on such surfaces. In specific embodiments, films, coatings and/or hydrogels or the like of this disclosure provide a concentration of a one or more inhibitory compounds into the environment to be protected that ranges from the IC50 of the biofilm-inhibitory compound (which can be measured by methods as described herein) to the level of the compound that is cytotoxic to mammalian cells (which can be measured by methods as described herein). In specific embodiments, films, coatings and/or hydrogels or the like of this disclosure provide a concentration of a inhibitory compound into the environment to be protected that ranges from the $IC_{50}$ of the inhibitory compound (which can be measured by methods as described herein) to 0.250 mM. In more specific embodiments, the concentration of inhibitory compound provided to the environment to be protected ranges from 4 microM to 200 microM. In yet more specific embodiment, the concentration ranges from 2-10 time the IC50 of the biofilm-inhibitory compound to 200 microM. In additional embodiments, the concentration ranges from 10-200 microM, 10-100 microM, 20-100 microM, 40-200 microM, or 40 to 100 microM. Combination of the compounds of the disclosure can be achieved by combination of the compounds in a film, coating or hydrogel or can be achieved in a combination of films, coatings or hydrogels wherein each film, coating or hydrogel contains a different compound of the combination of compounds.

In specific embodiments, the loading of the film, coating or hydrogel with the biofilm-inhibitory compound ranges from 0.001 to 1 mg of compound/gram of polymer in the film, coating or hydrogel. In more specific embodiments, the loading of the film, coating or hydrogel with the biofilm-inhibitory compound ranges from 0.005 to 1 mg, 0.01 to 1 mg, 0.05 to 1 mg, 0.1 to 1 mg, 0.5 to 1 mg, 0.01 to 0.5 mg of compound/gram of polymer in the film, coating or hydrogel.

The combination of compounds of the disclosure can be applied to an environment or administered by individual controlled-release of the component compounds of the combination of inhibitory compounds of the disclosure or by combined controlled-release of a combination of compounds. Controlled release can be from a film formed on the surface to be protected or on a surface in the vicinity of the surface to be protected. Similar release can be used to disperse already-formed biofilms. Release from the film provides for spatially localized release at or near the surface to be protected or cleaned of biofilm enhancing the effectiveness of biofilm-inhibition. The rate of release can be controlled by changing the composition of film, coating or hydrogel as is known in the art. The release profile from the film can also be affected by varying the thickness of the films and the concentration of the one or more biofilm-inhibitory compounds in the film. The concentration of biofilm-inhibitory compounds in the film can be generally uniform throughout the film or the concentration may be non-uniform in the film.

The film, coating or hydrogel may be formed on the surface of a selected substrate by any known method. For example, the film may be formed by contacting of the surface with a solution of the polymer and active ingredient (e.g., one or more inhibitory compounds), allowing a film to form on the surface and repeating the contacting step until a film of desired thickness is formed. The concentration of active ingredient(s) can be the same or different in the contacting steps. For example, the solution in one or more steps may contain polymer, but no active ingredient.

The films of this disclosure may also be formed by dip-coating, spin coating, or solvent casting using methods known in the art.

In additional embodiments, the inhibitory compounds of the disclosure can be provided in bulk objects and optionally released from such objects. Bulk objects include disks, slabs and other substrates and other structural elements that can be implanted, incorporated or used in other ways in biomedical or non-biomedical application. For example, one or more inhibitory compounds of a combination of compounds of the disclosure can be incorporated into such objects, e.g., by absorption. In a specific embodiment, one or more biofilm-inhibitory compounds of the disclosure can be introduced into porous matrix of an object to provide for biofilm protection.

In specific embodiments, the inhibitory compounds and combinations thereof of this disclosure are non-bactericidal or can be employed at levels which are inhibitory without being bactericidal. In such embodiments, concerns associated with evolved resistance currently faced by approaches based on the use of conventional microbiocidal agents (e.g., antibiotics) are lessened.

The term alkyl as used herein refers to a saturated hydrocarbon group which is straight-chain or branched. Unless otherwise stated, an alkyl group can have from 1-20 carbon atoms. More specifically, an alkyl group can have from 1-18 carbon atoms. In certain embodiments, an alkyl group can have from 1-3 carbon atoms. In certain embodiments, an alkyl group can have from 1-5 carbon atoms. In certain embodiments, an alkyl group can have 1-6 carbon atoms.

The term alkoxy refers to an —O-alkyl group where the alkyl group is as defined above.

The term haloalkyl refers to an alkyl group substituted with one or more halogens. Halogens include fluorine, chlorine, bromine or iodine. Specific haloalkyl groups include halomethyl groups having 1-3 halogen substituents. Specific haloalkyl groups include —$CF_3$, —$CCl_3$, —$C_2F_5$, —$C_2Cl_5$ among others.

The term haloalkoxy refers to an —O-haloalkyl group where the haloalkyl group is defined herein.

The term alkenyl as used herein refers to a hydrocarbon group which is straight-chain or branched having at least one double bond. Unless otherwise stated, an alkenyl group can have from 2-20 carbon atoms. More specifically, an alkenyl group can have from 2-18 carbon atoms. In certain embodiments, an alkenyl group can have from 2-5 carbon atoms. In certain embodiments, an alkenyl group can have from 2-6 carbon atoms. In specific embodiments, an alkenyl group has one double bond. In certain embodiments, an alkenyl group has a γ-double bond at the end of the group distal from its site of attachment to another moiety. In specific embodiments, an alkenyl group has two double bonds.

The term alkynyl as used herein refers to a hydrocarbon group which is straight-chain or branched having at least one triple bond. Unless otherwise stated, an alkynyl group can have from 2-20 carbon atoms. More specifically, an alkynyl group can have from 2-18 carbon atoms. In certain embodiments, an alkynyl group can have from 2-5 carbon atoms. In certain embodiments, an alkynyl group can have from 2-6 carbon atoms. In specific embodiments, an alkynyl group has one triple bond. In certain embodiments, an alkynyl group has a γ-triple bond at the end of the group distal from its site of attachment to another moiety.

The term alkoxy refers to an —O-alkyl group where the alkyl group is as defined above.

The term haloalkyl refers to an alkyl group substituted with one or more halogens. Halogens include fluorine, chlorine, bromine or iodine. Specific haloalkyl groups include halomethyl groups having 1-3 halogen substituents. Specific haloalkyl groups include —$CF_3$, —$CCl_3$, —$C_2F_5$, —$C_2Cl_5$ among others.

The term haloalkoxy refers to an —O-haloalkyl group where the haloalkyl group is defined herein.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the disclosure, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individual or in any combination. Where a specific enantiomer is described, it is understood that this description includes the substantially pure enantiomer (95% or more pure with respect to the other enantiomer(s)) as well as non-racemic mixtures of enantiomer where the specified enantiomer is present in an amount greater than 50% (by moles) or in an amount greater than 75% (by moles) or in an amount greater than 85% (by moles). Compounds of formula I and II include isotopic variants where the isotopic ratios of one or more atoms of the compound are selectively adjusted, for example, one or more H are replaced with deuterium or tritium, or one or more $^{12}C$ are replaced with $^{13}C$ or $^{14}C$, etc. Such isotopic variants are useful at least in analytical and biological assays.

One of ordinary skill in the art will appreciate that synthetic methods and starting materials, analytical assays, functional assays, Gram-negative bacteria, growth and assay conditions other than those specifically exemplified can be employed in the practice of the disclosure without resort to undue experimentation. All art-known functional equivalents, of any such methods, device elements, starting materials, and synthetic methods are intended to be included in this disclosure. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The disclosure illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the disclosure. It is recognized that regardless of the ultimate correctness of any mechanistic explanation or hypothesis, an embodiment of the disclosure can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure.

THE EXAMPLES

Example 1: Materials and Methods

All chemical reagents were purchased from commercial sources (Alfa-Aesar, Sigma-Aldrich, and Acros) and used without further purification. Solvents were purchased from commercial sources (Sigma-Aldrich and J.T. Baker) and used as obtained, with the exception of dichloromethane ($CH_2Cl_2$), which was distilled over calcium hydride immediately prior to use. Water was purified using a Millipore Analyzer Feed System.

NMR spectra were recorded in deuterated NMR solvents at 300 MHz on a Varian MercuryPlus 300 spectrometer (NSF CHE-0342998) or at 400 MHz on a Bruker Avance-400 with SmartProbe and SampleJet (NSF CHE-1048642). Chemical shifts are reported in parts per million (ppm, δ) using corresponding solvents or tetramethylsilane (TMS) as a reference. Couplings are reported in hertz (Hz).

Electrospray ionization MS measurements were performed on a Waters LCT (NSF Award #CHE-9974839). Samples were dissolved in acetonitrile and sprayed with a sample cone voltage of 20. For exact mass measurements (EMM), an aliquot of a known compound (lock mass) is added to the sample and resprayed.

Reversed-phase high performance liquid chromatography (RP-HPLC) was performed using a Shimadzu system equipped with an SCL-10Avp controller, an LC-20AT pump, an SIL-10AF autosampler, an CTO-20A oven, and an SPD-M20A UV/vis diode array detector. A Phenomenex Gemini C18 column (5 μm, 4.6 mm×250 mm) was used for all analytical RP-HPLC work. Standard RP-HPLC conditions were as follows: flow rates were 1 mL min−1 for analytical separations; mobile phase A=water+0.1% TFA; mobile phase B=acetonitrile+0.1% TFA. Purities were determined by integration of peaks with UV detection at 220 nm FT-IR spectra were recorded with a Bruker Tensor 27 IR spectrometer, outfitted with a single reflection MIRacle Horizontal attenuated total reflectance (ATR) unit from Pike Technologies. A ZnSe crystal with spectral range 20,000 to 650 cm−1 was used for ATR-IR measurements.

All absorbance measurements were made in 200 μL of solution in a clear 96-well microtiter plate (Costar 3370) and pathlength-corrected using a Biotek Synergy 2 plate reader running Gen 5 software (version 1.05). Bacterial growth was assessed by measuring the culture cell density according to absorbance at 600 nm ($OD_{600}$). Assay data were analyzed using Microsoft Excel for Mac 2011 and GraphPad Prism 4 for Mac OS X.

BHL was purchased from Cayman Chemical. Chlorophenol red-β-D-galactopyranoside (CPRG) was purchased from Roche. Ortho-nitorphenyl-β-galactoside (ONPG) and OdDHL were purchased from Sigma Aldrich. Stock solutions of synthetic compounds (100 mM) were prepared in DMSO and stored at −20° C. in sealed vials. The amount of DMSO used in small molecule screens did not exceed 1% (v/v). No compound had an effect on bacterial growth over the concentrations tested.

AHL library compounds were synthesized using previously established solution-phase, EDC-mediated amide coupling procedures,[39] with the following modifications: AHL compounds were prepared from L-homoserine lactone and the respective carboxylic acids in ≥50 mg quantities. The primary base used was triethylamine (two equivalents per one equivalent carboxylic acid). The reaction was catalyzed with 10 mol % 4-dimethylaminopyridine (DMAP). Following washing with 10% v/v HCl, crude products were additionally washed with aqueous saturated $NaHCO_3$ and saturated brine. Exemplary variations of the general protocol were applied for compounds RN2, RN10 and RN11 as detailed below. Compounds RN6, RN3, RN3OH, RN12, RN36 were synthesized by previously established protocols.[55, 56] Compound RN9 head group (s)-3-amino-2-pyrrolidonone was synthesized as previously described,[57] and then coupled to butryl chloride.

Compounds herein are synthesized by methods as described and illustrated herein or by routine adaptation of such methods by choice of starting materials, solvents or reagents.

Herein AHL compound refers specifically to compounds having HG which is:

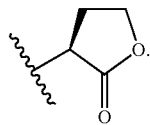 [SMILES: *[C@H]1CCOC1=O]

AHL*compound refers specifically to the enantiomers having HG which is:

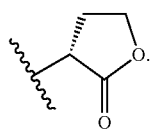 [SMILES: *[C@@H]1CCOC1=O]

AHL* enantiomers are synthesized by analogous method methods to those used to synthesize AHL compounds employing the appropriate enantiomeric starting material D-homoserine lactone. Synthesis of compounds of this disclosure having HG (or HG II) other than AHL were performed by analogous amide coupling methods employing the appropriate starting materials.

Bacterial Strains and Growth Conditions.

All media and reagents for bacterial culture were purchased from commercial sources. Bacteria were cultured in Luria-Bertani broth (LB) at 37° C. with shaking at 200 rpm unless otherwise noted. The bacterial reporter strains used for this study were (i) the heterologous E. coli strain JLD271 (ΔsdiA) harboring the RhlR expression plasmid pJN105R2 and the rhlI-lacZ transcriptional fusion reporter pSC11-rhlI*, (ii) the heterologous E. coli strain JLD271 (ΔsdiA) harboring the LasR expression plasmid pJN105L and the rhlI-lacZ transcriptional fusion reporter pSC11, and (iii) the P. aeruginosa strain PAO-JP2 (ΔlasrhlI) harboring the rhlI-gfp transcriptional fusion reporter prhlI-LVAgfp. Reporter strains JLD271/pJN105R2/pSC11-rhlI* and JLD271/pJN105L/pSC11 were grown in LB containing 100 μg/mL ampicillin and 10 μg/mL gentamicin. Freezer stocks of bacterial strains were maintained at −80° C. in 1:1 LB:50% glycerol.

E. coli RhlR and LasR Reporter Assay Protocol.

To evaluate the modulatory activities of library compounds on RhlR and LasR using E. coli reporters, the strains JLD271/pJN105R2/pSC11-rhlI* and JLD271/pJN105L/pSC11 were used, respectively, as previously described.[38, 51] The following modifications were used in the RhlR agonism reporter assay, non-native compounds (10 μM or 1 mM) were compared to 1 mM BHL as the positive control. Briefly, a subculture was prepared by diluting an overnight culture 1:10 with fresh media containing 100 μg/mL ampicillin and 10 μg/mL gentamicin, and was incubated until it had grown to OD600=0.45. In all assays, L-arabinose was added to a final concentration of 4 mg/mL to induce RhlR expression. For RhlR agonism assays, activities of test compounds were measured relative to 1 mM BHL (the concentration required to induce a maximal level of RhlR activity). For RhlR antagonism assays, test compounds were competed against a concentration of BHL approximately equal to its $EC_{50}$ value (10 μM). Activity was measured relative to 10 μM BHL. Inhibition was calculated by subtracting 100% from the relative activity value. Thus, 0% inhibition mimics represents no competitive displacement of 10 μM BHL by a test compound. In all assays, modifications were made to the standard Miller assay protocol to accommodate the use of the chlorophenol red-β-D-galactopyranoside (CPRG) β-galactosidase substrate. After cell lysis, 150 μL of the aqueous layer was transferred from each well of a solvent-resistant 96-well microtiter plate to the wells of a new clear, flat-bottom 96-well microtiter plate. CPRG (4 mg/mL in phosphate-buffered saline) was added to each well in 25 μL volumes. Plates were incubated at 30° C. until the positive control wells developed a red color (approximately 30 min). The amount of processed CPRG substrate was assessed by measuring the absorbance of each well at 570 nm. Enzymatic activity was calculated using the following equation:

adjusted Miller units=1000·Abs570/($OD_{600}$·t·V), where t is the incubation time of substrate with lysate and V is the volume of culture lysed.

LasR assays were processed using the protocol for the substrate ortho-nitrophenyl-β-galactoside (ONPG) as previously described elsewhere.[53]; and LasR antagonism assays were performed versus the $EC_{50}$ for OdDHL (2 nM).

P. aeruginosa RhlR Reporter Assay Protocol.

To evaluate the RhlR-modulatory activities of selected compounds in P. aeruginosa, the ΔlasIrhlI strain PAO-JP2 harboring plasmid prhlI-LVAgfp was used as previously reported.[38] Briefly, a subculture was prepared by diluting an overnight culture 1:100 in fresh LB and was grown to $OD_{600}$=0.3. Meanwhile, an appropriate amount of synthetic compound stock solution in DMSO (or BHL stock solution in DMSO as a control) was added to wells of black, clear-bottom 96-well microtiter plates (Costar 3904); final DMSO concentration (after addition of cells) did not exceed 1%. Subculture was treated with 100 nM OdDHL (to induce native expression of RhlR) by adding the appropriate amount of OdDHL stock solution in DMSO. The subculture was then dispensed (200 mL aliquots) into each synthetic compound-containing well of the microtiter plate.

Plates were incubated at 37° C. for 6 h, and GFP production was monitored by using a Synergy 2 plate reader ($\lambda_{ex}$=500 nm, $\lambda_{em}$=540 nm; BioTek, Winooski, Vt.) and quantified with Gen5 1.05 software (BioTek). The final $OD_{600}$ for each well was measured to normalize GFP production to cell density. All synthetic compounds were tested in triplicate, and three separate trials were performed with unique cultures. Agonism dose-response analyses were performed by testing compounds over a range of concentrations with the RhlR reporter. $IC_{50}$ values and 95% confidence intervals were calculated in Prism 4 software (GraphPad, San Diego, Calif.).

Example 2: RhlR Modulator Library Design

A goal of this work was non-natural AHLs and compounds with alternative headgroups with increased RhlR-modulatory potency. New libraries of potential RhlR modulators NR library (FIG. 3) and J library (FIG. 4) contain compounds that are believe not to have been tested for RhlR activity.

A first subset of compounds (J library) retains the short-chain alkyl characteristics of native ligand BHL, with compounds designed to probe (i) tail length, and (ii) alkyl substitution about the tail. Compound J18 (isovaleryl HL) is a naturally occurring AHL first found in the soybean symbiont Bradyrhizobium japonicum, it was included due to its close structural similarity to BHL. A second subset of compounds probes the stereochemistry and location of a tail vinyl group, as well as the presence of sp vs. $sp^2$ carbon hybridization. Finally, a third subset of compounds focuses on size and location of small carbon cycles within the acyl tail. It is currently believed that the cyclopentyl ring of compound S4 may lock the acyl tail into a conformation conducive for binding to the RhlR ligand binding site; slightly perturbing the conformation of the acyl tail may result in an even more potent RhlR modulator.

J Library Synthesis

AHL library compounds were synthesized using previously established solution-phase, EDC-mediated amide coupling procedures.[39] Yields were generally modest to good (40-80%), with >90% purity as assessed by HPLC. Two types of compounds generally suffered from lower coupling yields: those with quaternary carbons directly adjacent to the amide, and those with four or fewer carbon atoms in the acyl tail. The AHLs containing quaternary α-carbons in the tail (J20, J21, and J27) were low-yielding presumably due to steric effects during the coupling process. Those with the smallest acyl tails (C3AHL, J2, and J23) were more hydrophilic, likely resulting in loss of compound during the aqueous workup.

Biological Assay Methods

Because LuxR-type receptors are often unstable in solution, preventing the use of in vitro assays to directly assess small molecule agonism and antagonism, reporter gene assays represent a standard method for screening small-molecule libraries for LuxR-type receptor modulation. Previously reported strains for this purpose were used in the current study.[38] Synthetic N-butanoyl L-homoserine lactone (BHL), the native ligand of RhlR, was used as the positive control for receptor activation. Commonly, agonists are measured relative to maximum possible receptor activation within a particular assay medium;[40] because the dose-response curve of BHL is distinctly shallow in these RhlR reporters, a high concentration of BHL is required to maximally activate RhlR. In this study, activation of compounds was measured relative to that elicited by 1 mM BHL (the concentration of BHL used causes no aberrant growth effects in the reporter strain).

Heterologous RhlR Reporter Screen Reveals New Agonists

The RhlR-modulatory activity of the J library compounds was assessed in a heterologous reporter strain (*E. coli* JLD271 harboring plasmids pJN105R2 and pSC11-rhlI*) in order to isolate the RhlR receptor from upstream QS regulation (e.g. regulation by LasR). Thus, the extent to which compounds were directly modulating RhlR could be determined. These assays were performed by incubating compound-treated, mid-log phase *E. coli* reporter cells in 96-well microtiter plates, followed by Miller assay evaluation of ß-galactosidase activity.

RhlR agonism and antagonism screens of each compound were performed initially at 10 μM. Many compounds were quite strong agonists (Table 1), though no compounds were able to inhibit RhlR activity at 10 μM. Thus, compounds were submitted to a second competitive antagonism screen at 1 mM against 10 μM BHL (Table 1). Even at concentrations as high as 1 mM, only J20 and J27 were capable of inhibiting RhlR activity to a statistically significant extent. Both compounds contain a quaternary α-carbon with respect to the amide carbonyl group. This amount of steric bulk in close proximity to the HL head appears to significantly decrease compound potency, though it is interestingly the only structural feature in this study that allows short-tail AHLs to exhibit RhlR antagonism.

The agonism screen excitingly revealed multiple compounds with equal or higher efficacy than RhlR native ligand 1 (BHL). The most active compounds were J18 and J24 (86% and 79% activation, respectively), each capable of agonizing RhlR at levels equal to or higher than the strong RhlR agonist, S4. In assessing the effect of structural perturbation on compound activity on RhlR, the most influential structural feature appears to be substitution of the acyl tail α-carbon. Compounds with tertiary α- or β-carbons appear to be well accommodated by RhlR, though quaternary carbons abolish activity (see above). For example, compounds C5AHL J17, J18 and J19 showed comparable RhlR activation to that of BHL, whereas J20 and J21 were inactive as agonists. Similarly, cyclic-tail compounds J24 and J25 (70% activation) were strong

TABLE 1

RhlR agonism and antagonism data for exemplary compounds

| Compound | % activation[b] | % inhibition (10 μM)[c] | % inhibition (1 mM)[d] |
|---|---|---|---|
| BHL | 51 | — | — |
| D8 | 54 | −21 | −88 |
| S4 | 76 | −52 | −95 |
| C3-AHL | 25 | −5 | −66 |
| C5-AHL | 53 | −18 | −91 |
| J17 | 62 | −30 | −112 |
| J18 | 86 | −62 | −123 |
| J19 | 55 | −24 | −101 |
| J20 | 1 | 0 | 25 |
| J21 | 5 | 3 | 7 |
| J22 | 28 | 2 | −66 |
| J2 | 39 | 6 | −110 |
| J3 | 41 | −4 | −69 |
| J4 | 21 | 9 | −47 |
| J5 | 52 | −12 | −74 |
| J7 | 45 | −7 | −83 |
| J8 | 34 | −2 | −76 |
| J24 | 79 | −66 | −110 |
| J23 | 32 | −2 | −69 |
| J25 | 70 | −47 | −108 |
| J27 | 2 | 2 | 24 |
| S5 | 34 | 2 | −43 |
| B8[e] | 1 | 8 | 31 |
| RN6 | 1 | 8 | 55 |
| RN7 | 0 | 4 | 6 |
| RN5 | 2 | 1 | 11 |
| RN8 | 71 | −8 | −75 |
| RN9 | 1 | −1 | 35 |
| RN3 | 35 | −37 | −82 |
| RN4 | 0 | 9 | 45 |
| RN2 | 0 | −5 | 20 |
| RN3OH | 2 | 4 | 12 |
| RN11 | 0 | −3 | −1 |
| RN10 | 0 | 1 | 57 |
| RN12 | 56 | −39 | −98 |
| RN15 | 88 | −85 | −114 |
| RN36 | 42 | −35 | −122 |
| RN37 | 85 | −59 | −81 |
| RN13 | 0 | 24 | 25 |
| RN39 | 0 | 11 | 31 |
| RN17[f] | 1 | 6 | 24 |
| RN23 | 0 | 6 | 61 |
| RN22 | 1 | 28 | 74 |
| OdDHL[e] | 5 | 18 | 53 |

[a]Assays were performed using the heterologous RhlR reporter strain JLD271/pJN105R2/pSC11-rhlI*. SEM of n = 3 trials did not exceed ± 10%.
[b]Library compounds were screened at 10 μM. RhlR activity was measured relative to that of 1 mM BHL.
[c]Library compounds were screened at 10 μM in the presence of 10 μM BHL. Negative numbers indicate agonism stronger than that of 10 μM BHL alone.
[d]Library compounds were screened at 1 mM in the presence of 10 μM BHL. Negative numbers indicate agonism stronger than that of 10 μM BHL alone.
[e]Screened at a maximal concentration of 200 microM due to solubility concerns at higher concentrations.
[f]Screened at a maximal concentration of 100 microM due to solubility concerns at higher concentrations.

agonists, though 1-methyl-cylclopropanoyl AHL J27 was inactive. AHLs with 3-carbon tails significantly reduce the ability to activate RhlR, though AHLs with tails containing 4-6 carbons can be accommodated by RhlR. Compounds C3AHL, J2, and J23, the shortest in each class, were comparably less active than their respective counterparts.

The presence of an alkene or alkyne in the acyl tail had relatively little effect on compound activity. Compounds J5 and J7 were the most active of all compounds with unsaturated acyl tails: both displayed activities statistically insignificant from native ligand BHL. Of the subtle effects that this AHL group's tail structure conferred on activity, the most surprising was that decreasing carbon tail length from a pentenoyl tail (D8) to a butenoyl tail (J2) decreased activity, despite the native ligand BHL having a butanoyl tail.

Of the cyclic-tail AHLs tested, cyclobutanoyl AHL J24 displayed the strongest RhlR-agonistic activity (79% agonism). Though compound J23, with a cyclopropanoyl tail alone, appears to suffer in its ability to activate RhlR (32% activation), agonism was fully recovered in compound J25 (70% activation) by inserting a methylene group between the ring and the amide. Cyclohexyl tails are likely too large to be accommodated by RhlR, thus AHLs incorporating 3-5-membered rings in the acyl tail appear to be preferred for RhlR activation.

Dose-Response Studies of Selected RhlR Agonists Reveal Multiple Compounds More Potent than Native Ligand BHL With multiple compounds capable of strongly activating RhlR in hand, a subset of the J library was submitted to dose-response assays in the *E. coli* RhlR bioreporter to determine compound potency. Compounds that showed activity comparable to or greater than that of BHL were evaluated (Table 2). Of the new library compounds tested, AHLs J17, J18, J24, and J25 were significantly more potent than BHL. Cyclobutyl AHL J24 rivaled in potency that of S4, and J18 was significantly ($p<0.05$) more potent than 3. This naturally-occurring AHL, then, is the most potent activator of RhlR observed in this *E. coli* bioassay. Compound J18 is, in fact, almost 10-fold more potent than the native ligand.

TABLE 2

$EC_{50}$ values for RhlR activation by exemplary compounds in *E. coli* JLD271/pJN105R2/pSC11-rhlI*).[a]

| Compound | $EC_{50}$ ($\mu$M)[b] | 95% CI ($\mu$M) | Maximum Activation (%)[c] |
|---|---|---|---|
| BHL | 8.95 | 5.86-13.7 | 100 |
| D8 | 7.93 | 6.23-10.02 | 90 |
| S4 | 1.58 | 1.32-1.90 | 100 |
| C5 AHL | 10.83 | 6.59-17.80 | 80 |
| J17 | 4.89 | 3.67-6.53 | 95 |
| J18 | 1.02 | 0.67-1.55 | 105 |
| J19 | 7.77 | 5.61-10.8 | 95 |
| J5 | 6.93 | 5.52-8.71 | 80 |
| J24 | 1.78 | 1.37-2.31 | 100 |
| J25 | 2.76 | 2.23-3.42 | 95 |
| RN8 | 4.87 | 3.46-6.84 | 102 |
| RN3 | 27.4 | 16.1-46.6 | 92 |
| RN12 | 5.94 | 4.19-8.41 | 93 |
| RN15 | 1.72 | 1.34-2.21 | 106 |
| RN36 | 7.58 | 5.80-9.90 | 101 |
| RN37 | 0.463 | 0.336-0.640 | 93 |

[a]Determined by testing AHLs over a range of concentrations ($\leq 1$ mM). Assays were performed in triplicate, and 95% confidence intervals were calculated from the SEM of n $\geq 3$ trials.
[b]Denotes the highest value of LasR activation seen for each compound at any concentration within the dose-response assay. Exemplary agonism traces are illustrated in FIGS. 8A-8J.

Generally, the shapes of the dose curves were very consistent across the tested compounds. The dose-response of BHL is shallower (Hill slope=0.7) than most AHL-LuxR-type receptor interactions (Hill slope=~1.0) previously observed. This characteristic was conserved across all agonists. Shallow dose-response curves are often indicative of negative cooperativity of the small molecule binding to multiple sites on the receptor.[42] Since RhlR functions as a dimer, this negative cooperativity scenario is feasible if binding of an agonist to RhlR reduces binding affinity of the second dimer site for the agonist. Nevertheless, since the Hill slopes of all compound dose-response curves were consistently around 0.7, the single-concentration efficacy and overall compound potency tracked each other quite closely for each compound. Armed with a small set of compounds boasting potencies significantly higher than that of BHL, we chose to submit the two most potent library compounds, J18 and J24, to screening for RhlR-agonistic potency in a reporter housed in the native organism, *P. aeruginosa*. Compounds with high potencies in *P. aeruginosa* are generally more valuable in a range of contexts.

Top RhlR Modulators Fully Retain Potency in *P. aeruginosa*

Library compounds J18 and J24, as well as controls BHL and S4, were evaluated for potency in the native genetic background of RhlR by using the *P. aeruginosa* strain PAO-JP2 ($\Delta$lasIrhlI) harboring the RhlR reporter plasmid prhlI-LVAgfp (Table 3). Because the production of RhlR is dependent on LasR (in LB medium), all assays were performed in the presence of 100 nM OdDHL, enabling immediate transcription of RhlR via LasR activation. Interestingly, in the *P. aeruginosa* background, all four dose-response curves had Hill slopes much closer to 1, suggesting that the shallow dose-response relationships common in the *E. coli* reporter may be artifacts of heterologous expression. All compounds also retained similar potencies when screened in the *P. aeruginosa* background. Notably, the new RhlR modulators J18, J24 along with S4 are two of the most potent RhlR agonists now known. These data are particularly encouraging in light of many previous studies showing significantly decreased potency of compounds with larger acyl tails, when moving from *E. coli* bio-reporter assays to *P. aeruginosa* assays.

In particular, studies have shown that both active efflux pumps and AHL-degrading enzymes produced by *P. aeruginosa* (each of which could- or do-contribute to lower intracellular availability of non-native AHLs) recognize AHLs with acyl tails generally 6-14 carbons in length. Additionally, short-chain AHLs such as BHL diffuse across the *P. aeruginosa* cell membrane at a much higher rate than longer chain AHLs such as OdDHL. Because all of the compounds tested herein contain short ($\leq 6$ carbon) acyl tails, it is not surprising that compound potencies between the *E. coli* and *P. aeruginosa* reporter strains match so well. Compounds of this type appear to display an element of quorum-quenching "stealth," an extremely rare quality among the range of known AHL-based QS modulators.

TABLE 3

$EC_{50}$ values for RhlR activation by exemplary compounds in *P. aeruginosa* PAO-JP2/prhlI-LVAgfp).[a]

| Compound | $EC_{50}$ ($\mu$M)[b] | 95% CI ($\mu$M) | Maximum Activation (%)[c] |
|---|---|---|---|
| BHL | 8.08 | 6.09-10.7 | 100 |
| S4 | 1.22 | 1.03-1.45 | 106 |
| J18 | 1.42 | 1.08-1.86 | 94 |
| J24 | 1.41 | 1.14-1.74 | 95 |
| RN8 | 14.3 | 8.76-23.5 | 94 |
| RN3 | 3.82 | 2.57-5.66 | 95 |
| RN12 | 7.35 | 5.26-10.3 | 96 |
| RN15 | 1.65 | 1.24-2.21 | 90 |
| RN36 | 11.24 | 7.41-17.1 | 96 |
| RN37 | 2.58 | 1.86-3.56 | 91 |

[a]Determined by testing AHLs over a range of concentrations ($\leq 1$ mM). Assays were performed in triplicate, and 95% confidence intervals were calculated from the SEM of n $\geq 3$ trials.
[b]Denotes the highest value of LasR activation seen for each compound at any concentration within the dose-response assay. For the exemplary agonism traces, see FIGS. 9A-D.

Non-native compounds generally displayed non-monotonic dose curves (e.g. curves that increase in activity at low concentrations, followed by a decrease at high concentrations-often referred to as an "inverted U-shape" curve). A non-monotonic dose-response phenomenon had been observed in two contexts previously: (i) Many potent LasR inhibitors upturn to agonism at high concentrations (U-shaped),[43-46] and (ii) Compound S4 displayed an inverted U-shaped biphasic dose-response. The U-shaped curves were due to two different binding events at different concentrations. Notably, the high-concentration binding event exhibited partial agonism. It may be the case that these compounds are displaying partial agonism at high concentrations, as well. Nevertheless, these non-native agonists display efficacious RhlR agonism at low-micromolar concentrations, making them promising candidates for further antivirulence study.

Compound S4 is one of the most potent inhibitors of pyocyanin production in wild-type *P. aeruginosa* (and it exerts its inhibitory activity through RhlR activation), and both compounds J18 and J24 show comparable RhlR-modulatory potency. These compounds expand the chemical space known to be necessary for RhlR activation and open up new possibilities for future ligand design. Finally, due to the conservation of these compounds' potency in *P. aeruginosa* bioreporters (as compared to potencies in *E. coli* bioreporters), these compounds are bypassing mechanisms such as active efflux and degradation that often plague small-molecule modulation of *P. aeruginosa* intracellular receptors. Future compound design could focus on compounds with alternative head groups that bypass the hydrolytic instability of homoserine lactones.

Example 3: Preparation and Assessment of RN Library

Figures 1, 3A:
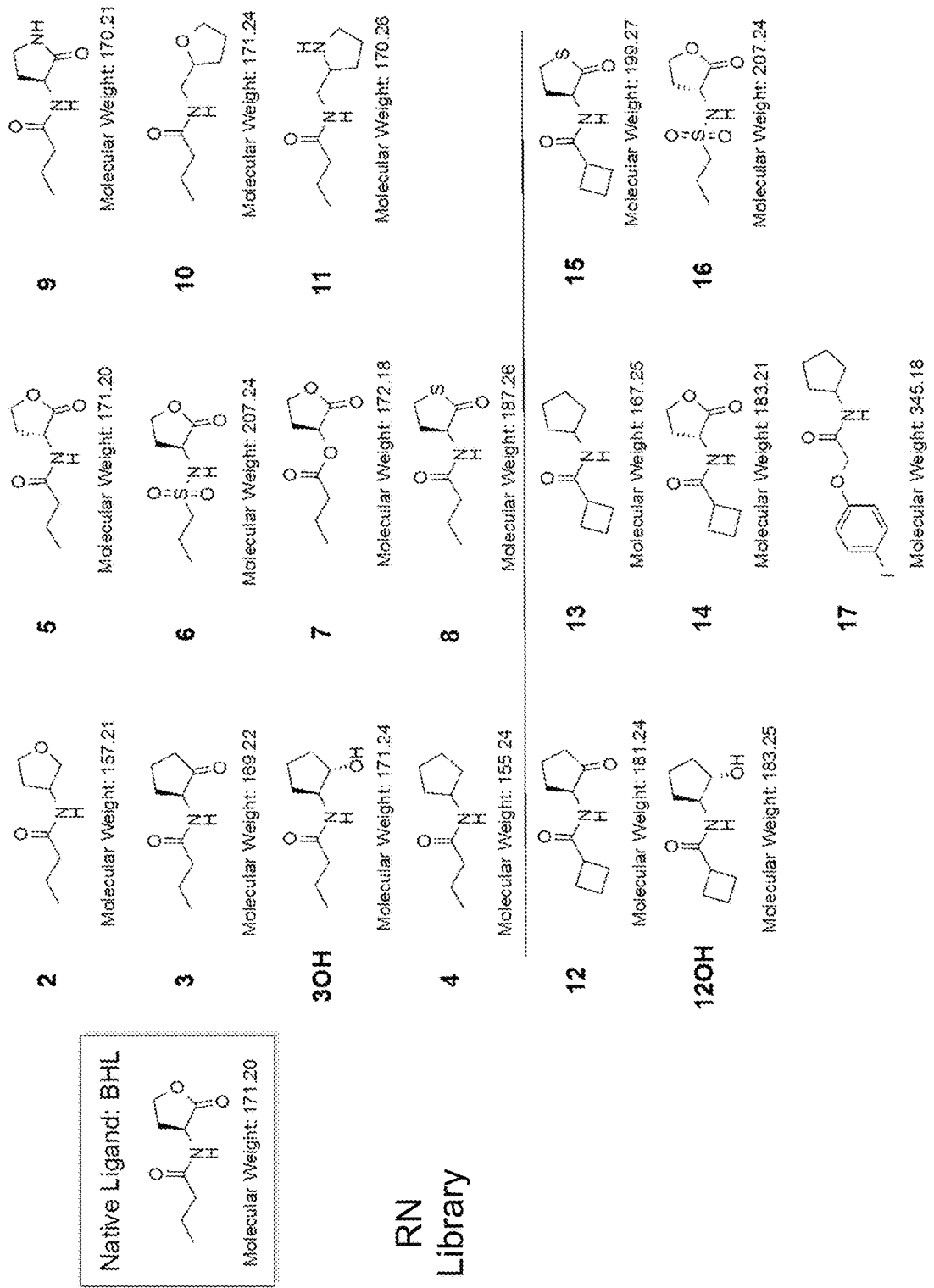
FIG. 3A (2 sheets) illustrates structures of compounds of the NR library.
Figures 2, 3A:
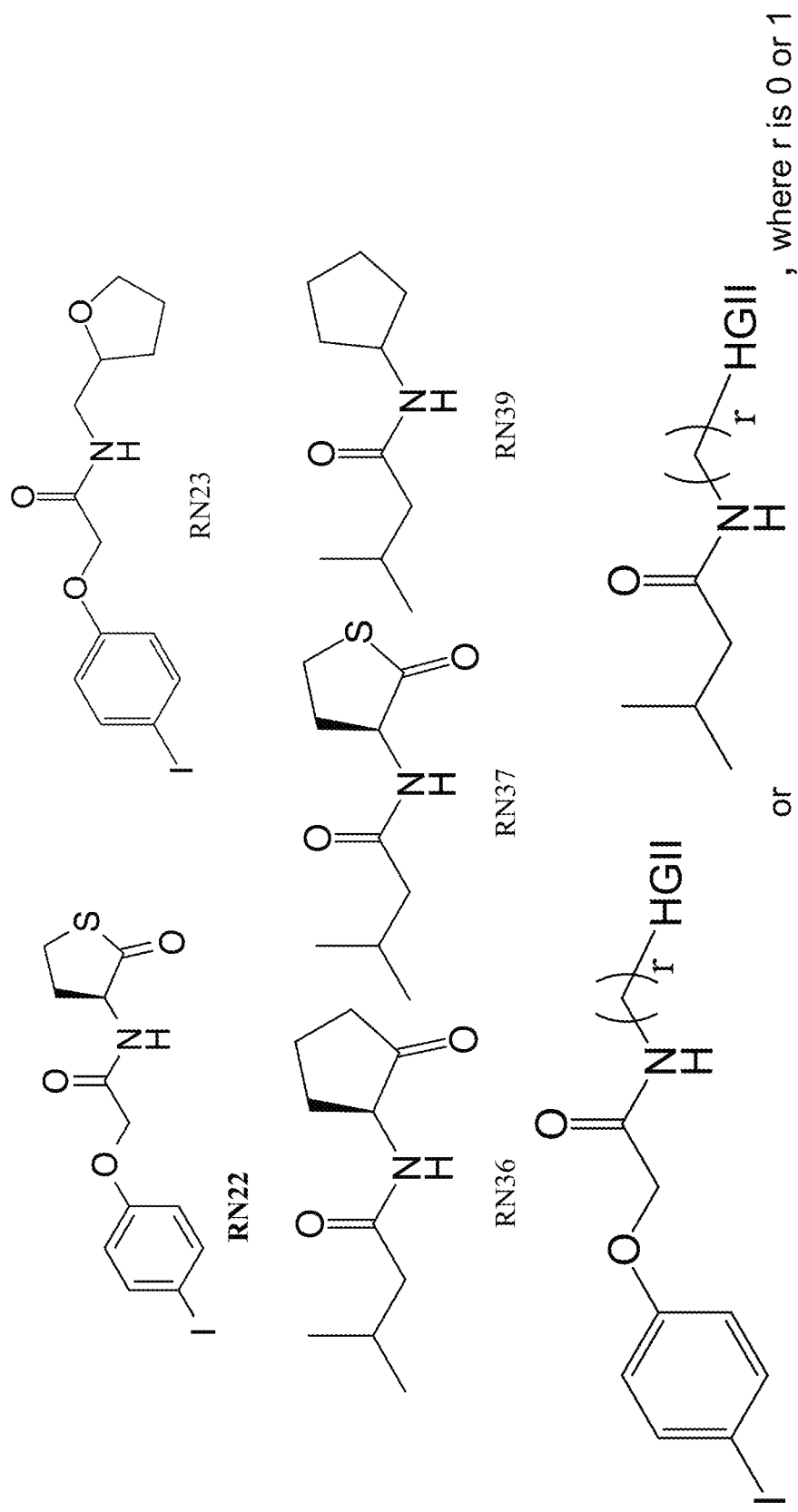
Figure 3B:
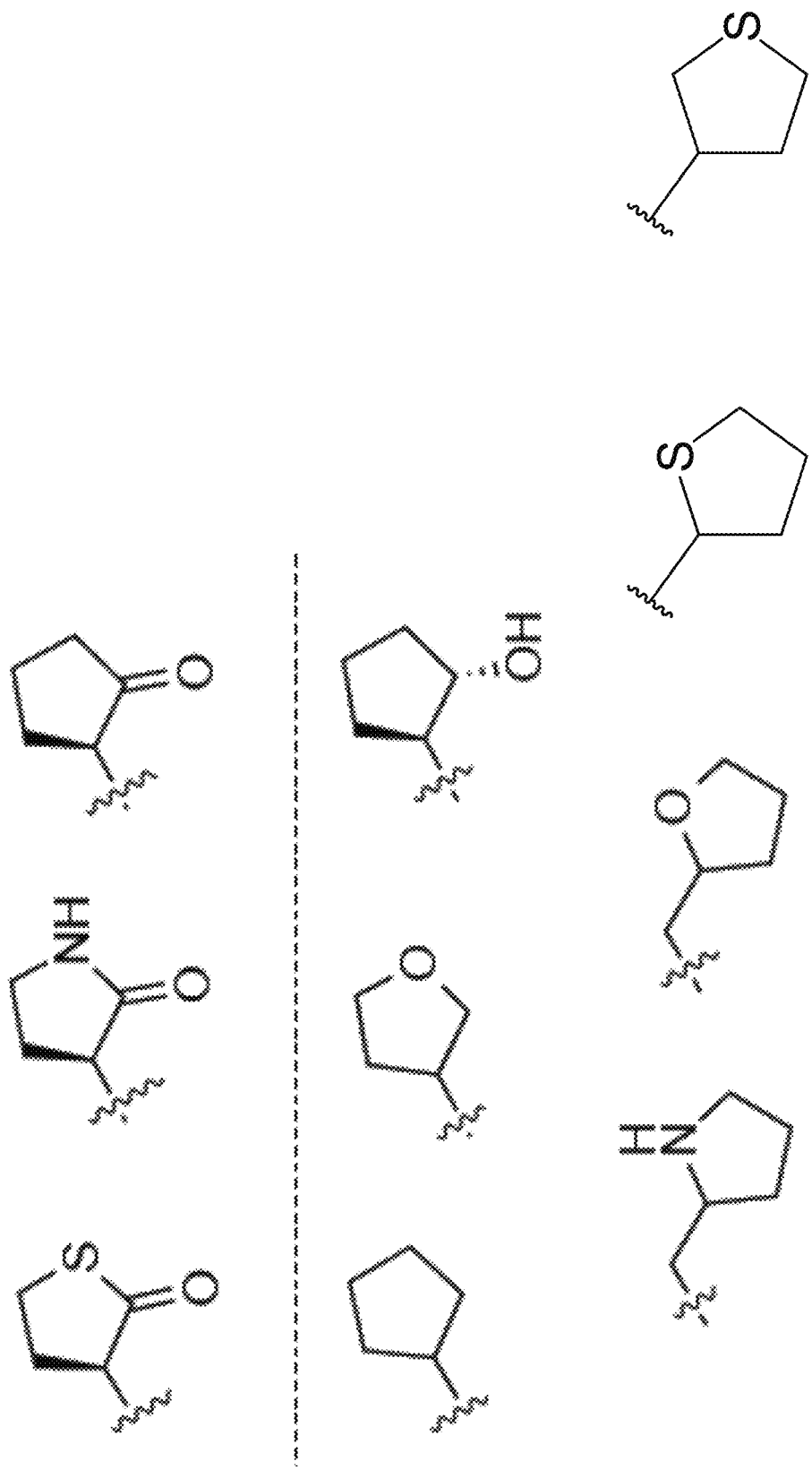
FIG. 3B illustrates exemplary structures of head groups of RhlR modulators.
Figure 4:
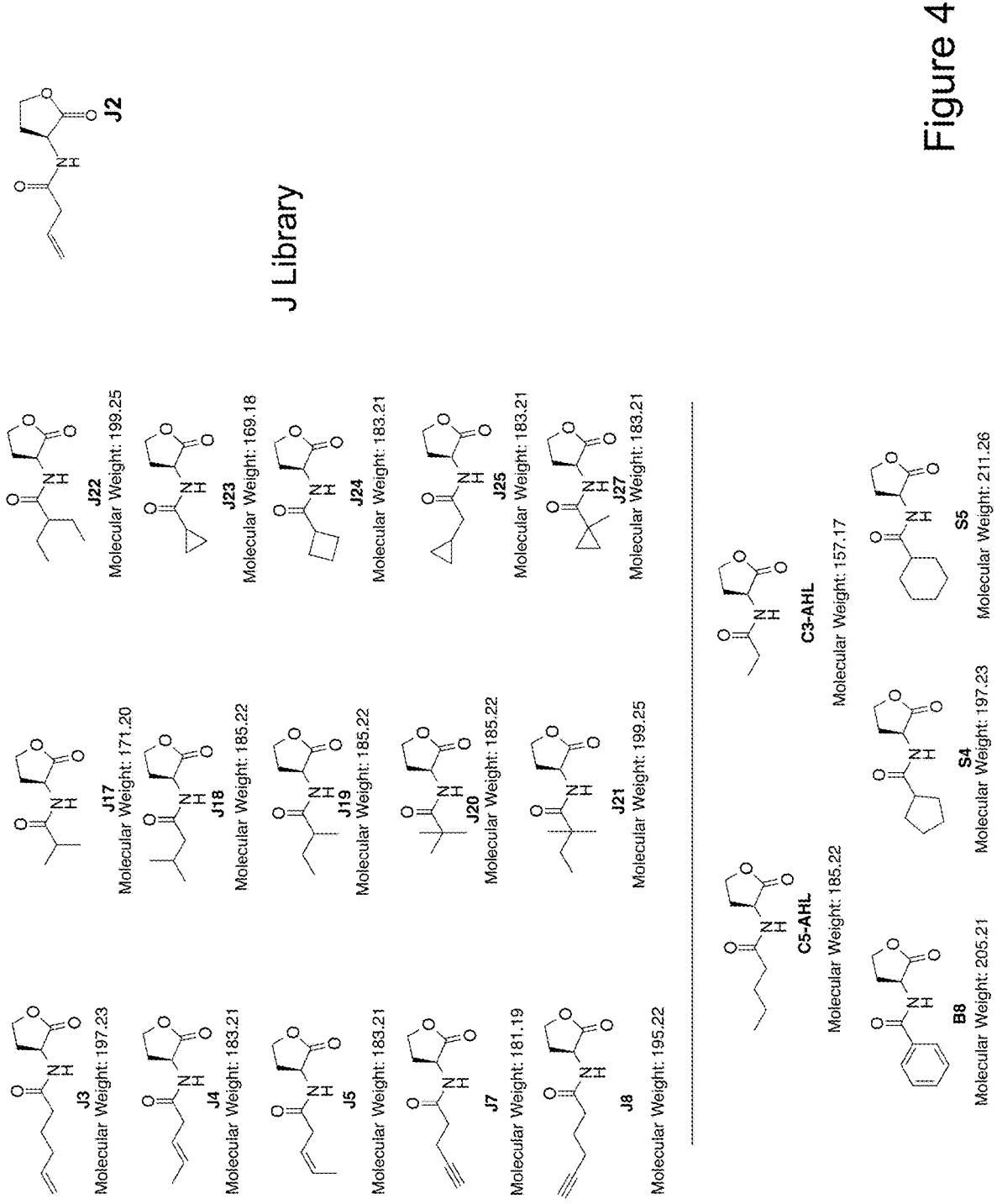
FIG. 4 illustrates structures of compounds of the J library.

The RN library as exemplified in FIG. 3 was prepared employing EDC-mediated or related amide coupling procedures. The RN library (compounds RN2-RN17 and RN3OH and RN12OH) was designed at least in part to assess the effect of changes in head groups (HG or HGII groups) on biological activity with respect to tail groups (A and AII) assessed in the J library. Table 1 provides exemplary *E. coli* reporter data with respect to antagonists of RhlR. Tables 1 2 and 3 provide exemplary *E. coli* reporter and *P. aeruginosa* reporter data with respect to agonists of RhlR.

Example 4: Exemplary Thiolactones

The synthesis of thiolactones of formula I is exemplified by the synthesis of compound RN22

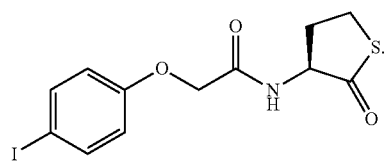 [SMILES: O=C(COc1ccc(I)cc1)N[C@H]1CCSC1=O]

This compound was synthesized using previously established solution-phase, EDC-mediated amide coupling procedures.[39] The two starting materials, 4-iodophenoxyacetic acid and 1,4-thiolactone hydrochloride, were purchased from Sigma Aldrich. The final product was purified using flash column chromatography in a EtOAc/Hex gradient, and purity was checked via NMR and Mass spectrometry (MS).

Characterization Data:
$^1$H NMR (500 MHz, CDCl$_3$) δ 7.70-7.48 (m, 2H), 6.94 (d, J=7.6 Hz, 1H), 6.77-6.68 (m, 2H), 4.61 (dt, J=13.2, 6.7 Hz, 1H), 4.50 (d, J=2.6 Hz, 2H), 3.39 (td, J=11.8, 5.1 Hz, 1H), 3.32-3.27 (m, 1H), 3.02-2.88 (m, 1H), 2.01 (qd, J=12.4, 7.0 Hz, 1H); $^{13}$C NMR (126 MHz, CDCl$_3$) δ 204.7, 168.4, 157.0, 138.8, 117.2, 84.9, 67.4, 59.1, 31.8, 27.7; Expected [M+H]$^+$: 377.9655, observed: 377.9650; IR (cm$^{-1}$): 3282, 2974, 2926, 2858, 1696, 1655, 1536, 1233

Figure 10A:
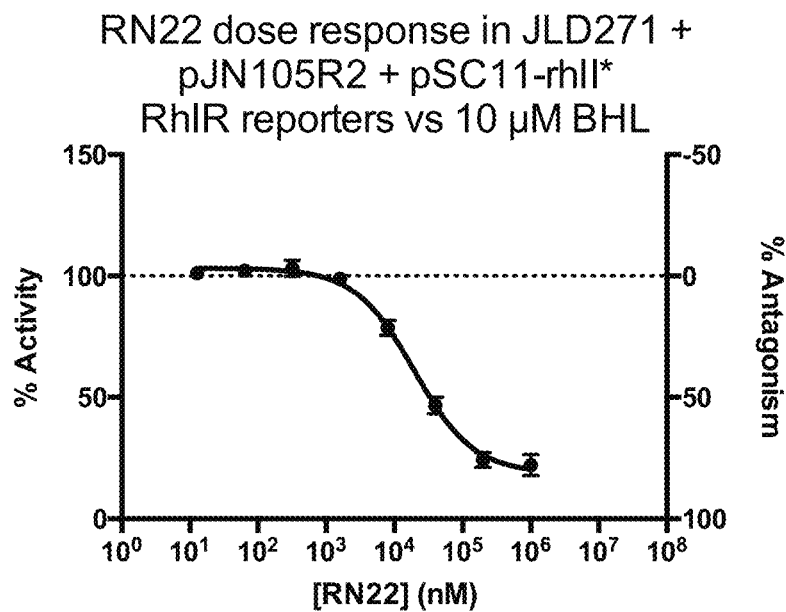
FIGS. 10A and B illustrate exemplary dose-response curves for RhlR antagonism in the *E. coli* JLD271/pJN105R2/pSC11-rhlI* reporter strain vs. 10 µM BHL (FIG. 10A) and in the *P. aeruginosa* PAO-JP2/prhlI-LVAgfp reporter strain vs. 10 µM BHL (FIG. 10B). $IC_{50}$ values and associated 95% Confidence Intervals (see Example XII) were calculated using GraphPad Prism.
Figure 10B:
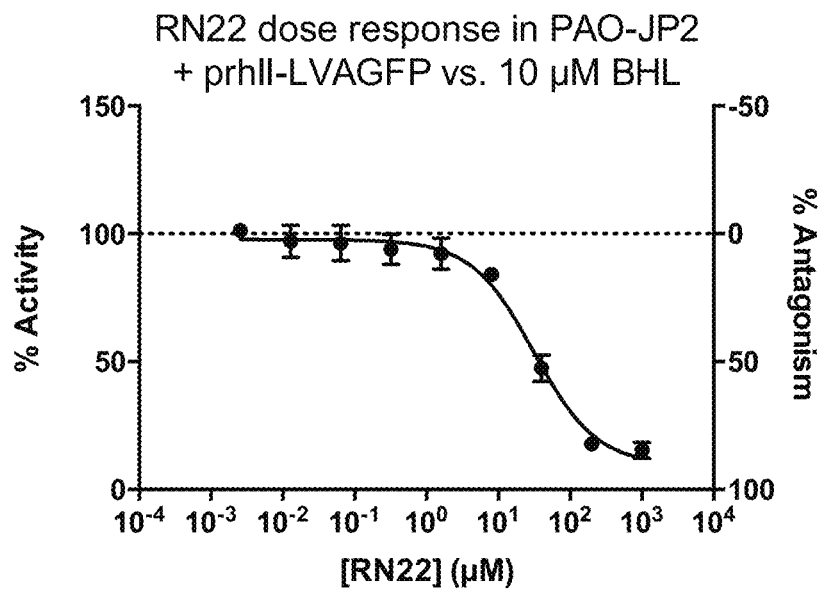

Antagonism activity data for thiolactone compound RN22 were collected as described above in the *E. coli* reporter (FIG. 10A) and the *P. aeruginosa* reporter (FIG. 10B). For the *E. coli* reporter the results were: IC$_{50}$: 19.6 μM and 95% CI: 14.3 μM-26.9 μM. For the *P. aeruginosa* reporter the results were: IC$_{50}$: 31.4 μM and 95% CI: 19.6 μM-50.4 μM. Few RhlR inhibitors have been reported, and compound RN22 is amongst the most potent RhlR inhibitors (IC$_{50}$=31 μM in *P. aeruginosa*). For context, the native ligand QS ligand for RhlR has an EC$_{50}$ of ~8 μM, so compound RN22 can block the activity of the native ligand by 50% at a less than 4-fold higher concentration.

Compounds RN17 and RN23 having a p-I-phenyloxy A group were prepared by methods as described herein above.

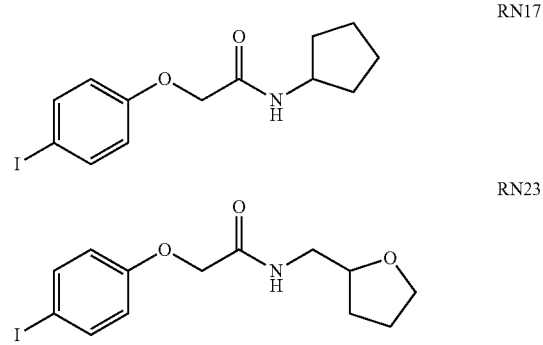

These compounds tested as described above for the corresponding thiolactone were found to be antagonists of RhlR in the *E. coli* reporter screen as described herein above. Compound RN17 exhibited maximum inhibition of 31% vs. 10 μM BHL. Compound RN23 exhibited maximum inhibition of 56% vs. 10 μM BHL. In contrast, the corresponding thiolactone exhibited maximum inhibition of 815 vs. 10 μM BHL in an analogous assay.

Example 5: Hybrid Compounds Generated by Combining Head Groups and Tail Groups

In an attempt to generate more potent modulators, promising head groups and tail groups identified in earlier screening experiments and prior studies were combined. Such compounds could provide modulators with desirable monotonic dose response curves.

An exemplary probe for new RhlR agonist structures, combined agonists head groups and tail groups, specifically the cyclopentanone and thiolactone head groups with the isovaleryl or cyclobutanoyl tails (RN12, RN15, RN36 and RN37). An exemplary probe for RhlR antagonists, combined the cyclopentylamine head group with the isovaleryl or cyclobutanoyl tails (RN13 an RN39). Again with an eye toward antagonism, cyclopentylamine, tetrahydrofurfurylamine, and thiolactone head groups were combined with the tail group from the potent RhlR antagonist E22 identified in an earlier study[51] to generate compounds RN17, RN23 and RN22. E22 is highly selective for RhlR over other LuxR-type receptors in *P. aeruginosa* and can strongly inhibit rhamnolipid production.[51]

These hybrid compounds were synthesized with the same EDC-based coupling protocol outlined above, and yields were generally moderate to good (40% to quantitative yield). Hybrid compounds were subjected to the same single point agonism and antantagonism screens in an *E. coli* RhlR reporter (Table 1) as well as the LasR reporter (Table XX). In the RhlR agonism screen, compounds RN12, RN15, RN36 and RN37 proved very active at 10 μM (Table 1) as well as at 1 mM with greater than 50% activity at 10 M. Compounds RN13, RN23, and RN22 showed potent antagonist activity, with compounds RN23 and RN22 inhibiting RhlR activity by greater than 50% at 1 mM. These three compounds were also submitted to dose response screening versus 10 μM BHL.

When assayed in a follow-up dose response experiment, all four compounds proved more potent than the native ligand BHL (Table XX). The addition of a bulkier tail group improved the potency of both the cyclopentanone and thiolactone head groups over the normal alkyl chain. Compound RN15 maintains activity that is equipotent to the cyclobutanoic tail group parent, compound J24. Importantly, the addition of a thiolactone to the isovaleryl tail in compound RN37 improves potency two-fold over the homoserine lactone variant and previous lead compound S4. Compound RN37 is the most potent RhlR agonist found in the *E. coli* reporter.

maximum inhibition decreased substantially. Additionally, the curve for RN13 showed undesirable non-monotonic behavior problematic for some AHL antagonists.[52] Compound RN23 showed a negligible maximum potency difference from its head group parent compound RN10. Compound RN22 showed activity comparable to previously identified compound E22. Previous studies have noted the lactone carbonyl to be important for compound activity, and E22 is able to retain the important interaction between Trp68, a residue conserved in all AHL binding LuxR-type receptors, and the carbonyl oxygen.

Agonist compounds RN12, RN15, RN36, and RN37 were carried into the *P. aeruginosa* reporter assay and dose response curves were performed. While compounds RN12 and RN13 maintained activity between the two different reporters, compounds RN36 and RN37 were not able to retain potency. Both of these latter two compounds utilized the isovaleryl tail group, possibly suggesting hybrids with this tail are more susceptible to *P. aeruginosa*'s arsenal of pumps and proteases or even processed by its complex metabolism. Methyl-branched compounds such as isovalerate are catabolized by *P. aeruginosa*.[54] Despite the reduction in potency seen in the hybrid compounds, no non-monotonic dose behavior was observed.

TABLE 4

$EC_{50}$ values for RhlR activation by certain hybrid compounds in *E. coli* or *P. aeruginosa*[a]

| | E. coli | | | P. aeruginosa | | |
|---|---|---|---|---|---|---|
| Compound | EC50 (μM)[b] | 95% CI (μM) | Maximum Activation (%)[c] | $EC_{50}$ (μM)[b] | 95% CI (μM) | Maximum Activation (%)[c] |
| RN12 | 5.94 | 4.19-8.41 | 93 | 7.35 | 5.26-10.3 | 96 |
| RN15 | 1.72 | 1.34-2.21 | 106 | 1.65 | 1.24-2.21 | 90 |
| RN36 | 7.58 | 5.80-9.90 | 101 | 11.24 | 7.41-17.1 | 96 |
| RN37 | 0.463 | 0.336-0.640 | 93 | 2.58 | 1.86-3.56 | 91 |

[a]Assays were performed using *E. coli* JLD271 (pJN105R2/pSC11-rhlI*) or *P. aeruginosa* PAO-JP2 (prhlI-LVAgfp); see Experimental Section. For both assays, $EC_{50}$ values were determined by testing AHLs over a range of concentrations (≤1 mM). Assays were performed in triplicate, and 95% confidence intervals (CIs) were calculated from the SEM of n ≥3 trials.
[b]Denotes the highest value of RhlR activation seen for each compound at any concentration within the dose-response assay. For the full agonism traces, see FIG. S1.
[c]RhlR activity was measured relative to that of 1 mM BHL.

TABLE 5

$IC_{50}$ values for RhlR inhibition by hybrid library members in *E. coli* and *P. aeruginos*[a]

| | E. coli | | | P. aeruginosa | | |
|---|---|---|---|---|---|---|
| Compound | $IC_{50}$ (μM)[b] | 95% CI (μM) | Maximum Inhibition (%)[c] | $IC_{50}$ (μM)[b] | 95% CI (μM) | Maximum Inhibition (%)[c] |
| RN13 | 26.7 | 10.1-71.0 | 32 | | | |
| RN23 | >100 | — | 56 | | | |
| RN22 | 19.6 | 14.3-26.9 | 81 | 31.4 | 19.6-50.4 | 85 |
| E22[35] | 17.3 | 12.1-24.6 | 74 | 23.9 | 16.6-31.6 | 96 |

[a]Determined by testing AHLs over a range of concentrations (≤1 mM). Assays were performed in triplicate, and 95% confidence intervals were calculated from the SEM of n ≥ 3 trials.
[b]Denotes the highest value of RhlR activation seen for each compound at any concentration within the dose-response assay.
[c]Values are expressed relative to activation of 10 μM BHL alone.

Dose response data for antagonist RN13 (with cyclobutyl tail) showed two-fold increased potency as measured by $IC_{50}$ over parent compound RN4 (with n-butyl tail), but the When competed versus 10 μM BHL in the *P. aeruginosa* antagonism assay, compound RN22 maintained its strong inhibitory profile. However, unlike the shorter chain RhlR agonists, its $IC_{50}$ decreased as compared to its activity in *E. coli*, likely due to the longer acyl chain's susceptibility to active efflux pumps and acylases.[46] Related compound E22 fared slightly better, with its $IC_{50}$ decreasing only ~1.4 fold and maximum inhibition increasing more than 20%. Compounds E22 and RN22 are thus among the most potent antagonists of RhlR identified.

Example 6: Selectivity of RhlR Agonist Over LAS Agonism

The selectivity of certain compounds for RhlR over LasR was measured using a LasR reporter strain (details above). Table 6 provides a comparison of selectivity of RhlR agonism over LasR agonism for exemplary compounds. Table 7 provides a comparison of selectivity of RhlR antagonism over LasR antagonism for exemplary compounds.

TABLE S4

Fold selectivity of RhlR agonists over LasR agonism.[a]

| | Tested Concentration | |
|---|---|---|
| | 10 μm | 1 mM |
| BHL | 56 | 18 |
| D8 | >54[b] | 3.7 |
| S4 | 12 | 4.4 |
| J18 | 255 | >99[b] |
| J24 | >79[b] | 48 |
| RN8 | 17 | 4.5 |
| RN3 | >36[b] | 11 |
| RN12 | >56[b] | 6.8 |
| RN15 | >88[b] | 11 |
| RN36 | 105 | >84[b] |
| RN37 | >85[b] | 13 |

[a] Values calculated by dividing RhlR % activity by LasR % activity.
[b] Compound showed negligible activity in LasR reporter.

TABLE S5

Fold selectivity of RhlR antagonist 42 over LasR antagonism.[a]

| | Tested Concentration | |
|---|---|---|
| | 10 μm | 1 mM |
| RN22 | 1.5 | 74 |

[a] Values calculated by dividing RhR % antagonism by LasR % antagonism.

Example 7

To assess the relative stability of the thiolactone and homoserine lactone moieties, stability studies were performed as reported previously,[53] with the following changes. Compounds RN22 and E22 (50 μM) were dissolved in either 1 mM 2-(N-morpholino)-ethanesulfonic acid (MES) buffer at pH 6, or 1 mM tris(hydroxymethyl)-aminomethane (TRIS) buffer at pH 7, pH 8, or pH 9. Solutions were placed static at room temperature, and 150 μL aliquots were taken every two hours for eight hours, then again at 24 hours. Samples were immediately separated via HPLC, and the area under the curve (AUC) at 220 nm was calculated and compared to the area at t=0. Caffeine (50 μM) was added as an internal standard (0.15% DMSO) and maintained the same AUC throughout the assay (error ≤1-5%). Degradation of both compounds to the hydrolysis product was confirmed via mass spectrometry of the resulting byproduct peak.

Figure 11A:
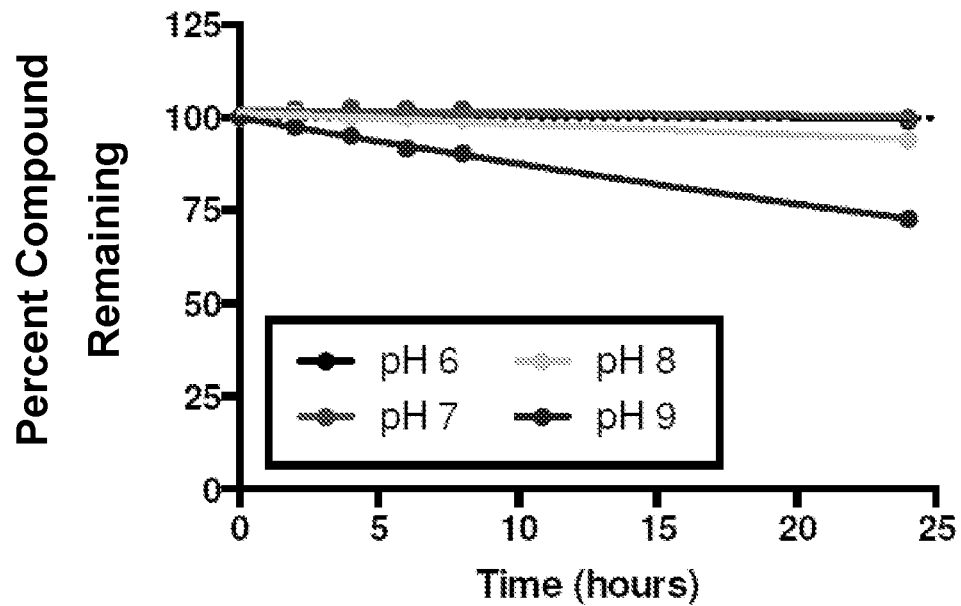
FIGS. 11A and 11B are graphs comparing stability of compounds RN22 (FIG. 11A) and E22 (FIG. 11B) at varying pH over time.
Figure 11B:
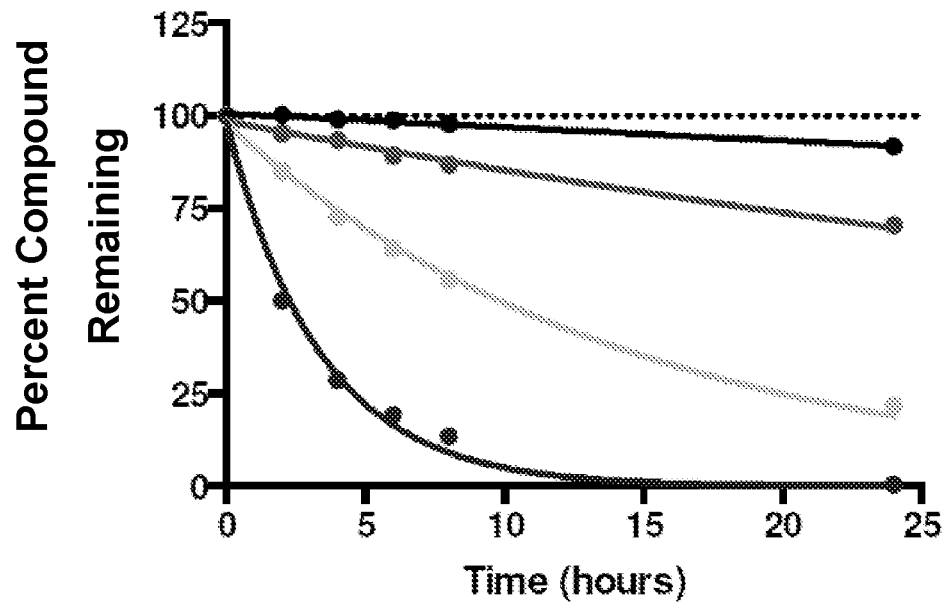

P. aeruginosa media is observed to become more alkaline over time, making the hydrolytic instability of the homoserine lactone head group a concern in developing AHL-type modulators for use in the wild-type organism. Certain thiolactone derivatives have increased hydrolytic stability relative to AHLs in Luria-Bertani medium as monitored via a biosensor assay.[71] Several of the most active RhlR modulators identified in this study contain the thiolactone headgroup. To evaluate their stability in a more direct assay, the stability of thiolactone RN22 relative to its lactone homolog E22 was monitored over time and at varying pH values using HPLC. The amount of compound RN22 remaining over 24 h was compared to E22. The thiolactone in this assay displayed remarkable stability, with half lives ranging from approximately 6 to 23 times longer than the half lives of the homoserine lactone headgroup at varying pH values (FIGS. 11A and 11B, half lives reported in Table 8). Degradation products were confirmed to be the hydrolyzed lactone head groups via mass spectroscopy.

TABLE 8

Half lives of compounds 42 and E22 in varying pH buffers

| | Half Life (hours) | | | |
|---|---|---|---|---|
| Compound | pH 6 | pH 7 | pH 8 | pH 9 |
| RN22 | 1055.0 | 1132.0 | 237.2 | 52.4 |
| E22 | 182.5 | 48.1 | 10.1 | 2.3 |

Example 8: Synthesis and Characterization of Exemplary Compounds $^1$H and $^{13}$C NMR, ESI MS, and IR data are reported below for certain non-native RhlR modulators.

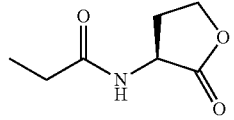

C3-AHL:
$^1$H NMR: (400 MHz, CDCl$_3$) δ 6.30 (NH, br d, J=6.5 Hz, 1H), 4.61 (lac CH, ddd, J=11.6, 8.6, 6.2 Hz, 1H), 4.47 (lac CH, td, J=9.0, 1.3 Hz, 1H), 4.29 (lac CH, ddd, J=11.3, 9.3, 5.9 Hz, 1H), 2.82 (lac CH, dddd, J=12.6, 8.7, 5.9, 1.3 Hz, 1H), 2.30 (CH$_2$, qd, J=7.7, 1.1 Hz, 2H), 2.16 (lac CH, dtd, J=12.4, 11.4, 8.8 Hz, 1H), 1.17 (CH$_3$, t, J=7.6 Hz, 3H); $^{13}$C NMR (101 MHz, CDCl$_3$) δ 175.78, 174.39, 66.13, 49.14, 30.44, 29.16, 9.47; ESI MS: Expected [M+H]$^+$: 158.0812, observed: 158.0810; IR (cm$^{-1}$): 3311, 2980, 2939, 1792, 1641, 1535, 1170, 1028.

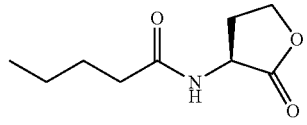

C5-AHL:
$^1$H NMR (400 MHz, CDCl$_3$) δ 6.09 (NH, br s, 1H), 4.56 (lac CH, ddd, J=11.6, 8.6, 5.9 Hz, 1H), 4.47 (lac CH td, J=9.0, 1.2 Hz, 1H), 4.29 (lac CH ddd, J=11.3, 9.3, 5.8 Hz, 1H), 2.86 (lac CH, dddd, J=12.6, 8.6, 5.9, 1.2 Hz, 1H), 2.26 (CH$_2$, dd (apparent t), J=8.3, 7.0 Hz, 2H), 2.13 (lac CH, dtd, J=12.4, 11.4, 8.8 Hz, 1H), 1.64 (CH$_2$, p, J=8.2, 7.6 Hz, 2H), 1.36 (CH$_2$, h, J=7.3 Hz, 2H), 0.92 (CH$_3$, t, J=7.3 Hz, 3H); $^{13}$C NMR (101 MHz, CDCl$_3$) δ 175.60, 173.75, 66.13, 49.25, 35.91, 30.65, 27.51, 22.33, 13.78; ESI MS: Expected [M+H]$^+$: 186.1125, observed: 186.1123; IR (cm$^{-1}$): 3309, 3078, 2950, 1774, 1649, 1545, 1169, 933

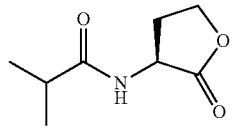

J17:

¹H NMR (400 MHz, CDCl₃) δ 6.05 (NH, br s, 1H), 4.53 (lac CH, ddd, J=11.7, 8.7, 5.8 Hz, 1H), 4.48 (lac CH, td, J=9.2, 0.8 Hz, 1H), 4.29 (lac CH, ddd, J=11.4, 9.3, 5.9 Hz, 1H), 2.87 (lac CH, dddd, J=12.6, 8.6, 5.8, 1.2 Hz, 1H), 2.45 (CH, hept, J=6.9 Hz, 1H), 2.12 (lac CH, dtd, J=12.6, 11.5, 8.8 Hz, 1H), 1.19 (CH₃, dd, J=6.9 Hz, 3H), 1.18 (CH₃, d, J=6.9 Hz, 3H); ¹³C NMR (101 MHz, CDCl₃) δ 177.58, 175.61, 66.13, 49.23, 35.22, 30.72, 19.50, 19.37; ESI MS: Expected [M+H]⁺: 172.0969, observed: 172.0963; IR (cm⁻¹): 3305, 2968, 2930, 1178, 1655, 1550, 1170, 1015.

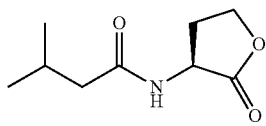

J18:

¹H NMR (400 MHz, CDCl₃) δ 5.96 (NH, br s, 1H), 4.54 (lac CH, ddd, J=11.6, 8.6, 5.7 Hz, 1H), 4.48 (lac CH, td, J=9.1, 1.2 Hz, 1H), 4.29 (lac CH, ddd, J=11.3, 9.3, 5.9 Hz, 1H), 2.88 (lac CH, dddd, J=12.9, 8.6, 6.1, 1.2 Hz, 1H), 2.21-2.02 (tail CH₂+tail CH+lac CH, m, 4H), 1.02-0.93 (CH₃, m, 6H); ¹³C NMR (101 MHz, CDCl₃) δ 175.44, 173.06, 66.11, 49.29, 45.44, 30.71, 26.14, 22.46, 22.38; ESI MS: Expected [M+H]⁺: 186.1125, observed: 186.1118; IR (cm⁻¹): 3308, 2956, 2869, 1774, 1642, 1546, 1169, 1014.

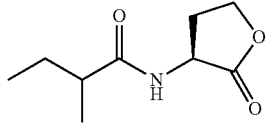

J19: 2 Diastereomers—Analogous Overlapping Signals are Reported Together.

¹H NMR (400 MHz, CDCl₃) δ 6.01 (NH, br s, diastereomers overlapping, 1H), 4.54 (lac CH, diastereomers 0.008 ppm apart, ddd, J=11.0, 8.0, 5.4 Hz, 1H), 4.48 (lac CH, diastereomers 0.005 ppm apart, td, J=9.0, 1.2 Hz, 1H), 4.29 (lac CH, diastereomers 0.002 ppm apart, ddd, J=11.4, 9.4, 6.0 Hz, 1H), 2.88 (lac CH, diastereomers 0.015 ppm apart), ddd, J=13.0, 8.7, 5.9, 1.3 Hz, 1H), 2.26-2.06 (tail CH+lac CH, diastereomers overlapping, m, 2H), 1.75-1.62 (tail CH₂, diastereomers overlapping, m, 1H), 1.54-1.41 (tail CH₂, diastereomers overlapping, m, 1H), 1.17 (tail CH₃, diastereomers 0.003 ppm apart, d, J=6.9 Hz, 3H), 0.93 (tail CH₃, diastereomers 0.02 ppm apart, t, J=7.4 Hz, 3H); ¹³C NMR (101 MHz, CDCl₃) δ 177.13, 177.07, 175.55, 175.50, 66.13, 66.10, 49.26, 49.19, 42.64 (2C), 30.77, 30.70, 27.35, 27.20, 17.28, 17.21, 11.81 (2C); ESI MS: Expected [M+H]⁺: 186.1125, observed: 186.1119; IR (cm⁻¹): 3306, 2967, 2926, 1776, 1645, 1545, 1174, 1016.

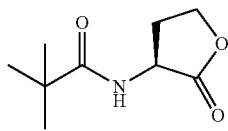

J20:

¹H NMR (400 MHz, CDCl₃) δ 6.18 (NH, br s, 1H), 4.53-4.43 (lac CH, m, 2H), 4.30 (lac CH, ddd, J=11.1, 9.3, 5.9 Hz, 1H), 2.87 (lac CH, dddd, J=12.6, 8.6, 6.0, 1.3 Hz, 1H), 2.12 (lac CH, dtd, J=12.5, 11.3, 8.9 Hz, 1H), 1.23 (t-Bu CH₃, S, 9H); ¹³C NMR (101 MHz, CDCl₃) δ 179.19, 175.66, 66.13, 49.37, 38.71, 30.62, 27.44; ESI MS: Expected [M+H]⁺: 186.1125, observed: 186.1123; IR (cm⁻¹): 3324, 2963, 1779, 1643, 1525, 1165, 1013.

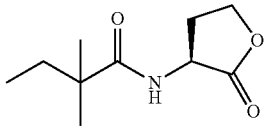

J21:

¹H NMR (400 MHz, CDCl₃) δ 6.16 (NH, br s, 1H), 4.54-4.43 (lac CH, m, 2H), 4.29 (lac CH, ddd, J=11.1, 9.3, 6.0 Hz, 1H), 2.86 (lac CH, dddd, J=13.0, 8.6, 6.0, 1.3 Hz, 1H), 2.12 (lac CH, dtd, J=12.4, 11.2, 8.9 Hz, 1H), 1.65-1.50 (tail CH₂, ABX₃ qq, J_{AB}=13.5 Hz, J_{AX}=~7 Hz, J_{BX}=~7 Hz, 2H), 1.19 (tail CH₃, s, 3H), 1.19 (tail CH₃, s, 4H), 0.86 (tail CH₃, t, J=7.5 Hz, 3H); ¹³C NMR (101 MHz, CDCl₃) δ 178.50, 175.64, 66.12, 49.36, 42.42, 33.89, 30.58, 24.84, 24.77, 9.13; ESI MS: Expected [M+H]⁺: 200.1282, observed: 200.1273; IR (cm⁻¹): 3312, 2967, 2914, 1770, 1632, 1530, 1170, 1028.

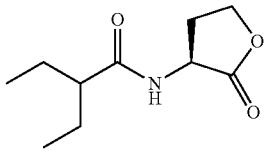

J22:

¹H NMR (400 MHz, CDCl₃) δ 6.00 (NH, br s, 1H), 4.54 (lac CH, ddd, J=11.5, 8.6, 5.6 Hz, 1H), 4.48 (lac CH, td, J=9.0, 1.3 Hz, 1H), 4.29 (lac CH, ddd, J=11.2, 9.3, 5.9 Hz, 1H), 2.94-2.83 (lac CH, m, 1H), 2.13 (lac CH, dtd, J=12.7, 11.4, 8.8 Hz, 1H), 1.97 (tail CH, tt, J=9.0, 5.3 Hz, 1H), 1.71-1.44 (tail CH₂, m, 4H), 0.92 (tail CH₃, t, J=7.4 Hz, 3H), 0.90 (tail CH₃, t, J=7.4 Hz, 3H); ¹³C NMR (101 MHz, CDCl₃) δ 176.47, 175.44, 66.12, 50.81, 49.25, 30.71, 25.70, 25.63, 12.03, 12.00; ESI MS: Expected [M+H]⁺: 200.1282, observed: 200.1280; IR (cm⁻¹): 3300, 2969, 2923, 1777, 1645, 1543, 1169, 1020.

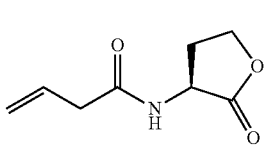

J2:

¹H NMR (400 MHz, CDCl₃) δ 6.44 (NH, br d, J=4.9 Hz, 1H), 5.94 (alkene CH, ddt, J=16.2, 11.0, 7.1 Hz, 1H), 5.30-5.20 (alkene CH, m, 2H), 4.59 (lac CH, ddd, J=11.6, 8.7, 6.4 Hz, 1H), 4.47 (lac CH, td, J=9.1, 1.3 Hz, 1H), 4.29 (lac CH, ddd, J=11.2, 9.2, 5.9 Hz, 1H), 3.08 (tail CH₂, dt, J=7.1, 1.3 Hz, 2H), 2.80 (lac CH, dddd, J=12.3, 8.7, 6.0, 1.2 Hz, 1H), 2.27-2.09 (lac CH, m, 1H); ¹³C NMR (101 MHz, CDCl₃) δ 175.49, 171.28, 130.56, 120.16, 66.09, 49.19, 41.01, 30.24; ESI MS: Expected [M+H]⁺: 170.0812, observed: 170.0809; IR (cm$^{-1}$) 3312, 3073, 2957, 2932, 1174, 1644, 1543, 1171, 1013

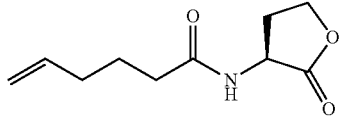

J3:
$^1$H NMR (300 MHz, CDCl$_3$) δ 6.18 (NH, br d, J=6.3 Hz, 1H), 5.78 (alkene CH, ddt, J=16.9, 10.2, 6.7 Hz, 1H), 5.04 (alkene CH, dq, J=16.5, 1.6 Hz, 1H), 4.99 (alkene CH, dq, J=9.4, 1.0 Hz, 1H), 4.58 (lac CH, ddd, J=11.6, 8.6, 6.1 Hz, 1H), 4.47 (lac CH, td, J=9.1, 1.3 Hz, 1H), 4.29 (lac CH, ddd, J=11.2, 9.3, 5.9 Hz, 1H), 2.83 (lac CH, dddd, J=12.5, 8.6, 5.9, 1.3 Hz, 1H), 2.27 (CH$_2$, dd (apparent t), 2H), 2.25-2.03 (tail CH$_2$+lac CH, m, 3H), 1.76 (tail CH$_2$, p, J=7.5 Hz, 2H); $^{13}$C NMR (75 MHz, CDCl$_3$) δ 175.80, 173.66, 137.86, 115.72, 66.31, 49.40, 35.47, 33.23, 30.72, 24.62; ESI MS: Expected [M+H]$^+$: 198.1125, observed: 198.1119; IR (cm$^{-1}$): 3312, 3077, 2935, 1774, 1643, 1544, 1169, 1013.

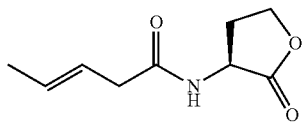

J4:
$^1$H NMR (400 MHz, CDCl$_3$) δ 6.16 (NH, br d, J=5.7 Hz, 1H), 5.68 (alkene CH, dqt, J=14.6, 6.3, 1.2 Hz, 1H), 5.55 (alkene CH, dtq, J=14.5, 7.2, 1.6 Hz, 1H), 4.54 (lac CH, ddd, J=11.6, 8.6, 5.9 Hz, 1H), 4.47 (lac CH, td, J=9.0, 1.1 Hz, 1H), 4.28 (lac CH, ddd, J=11.3, 9.3, 5.9 Hz, 1H), 3.00 (tail CH$_2$, dt, J=7.0, 1.3 Hz, 2H), 2.85 (lac CH, dddd, J=12.5, 8.9, 5.8, 1.2 Hz, 1H), 2.14 (lac CH, qd, J=11.7, 8.8 Hz, 1H), 1.74 (tail CH$_3$, dd, J=6.5, 1.6 Hz, 3H); $^{13}$C NMR (101 MHz, CDCl$_3$) δ 175.33, 171.98, 131.77, 122.84, 66.07, 49.29, 40.03, 30.56, 18.08; ESI MS: Expected [M+H]$^+$: 184.0969, observed: 184.0964; IR (cm$^{-1}$): 3326, 3292, 2946, 1773, 1644, 1166, 1015, 962.

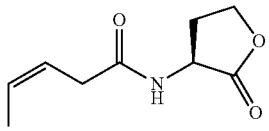

J5:
$^1$H NMR (400 MHz, CDCl$_3$) δ 6.16 (NH, br s, 1H), 5.81 (alkene CH, dqt, J=11.0, 6.9, 1.4 Hz, 1H), 5.59 (alkene CH, dtq, J=11.1, 7.5, 1.8 Hz, 1H), 4.54 (lac CH, ddd, J=11.7, 8.5, 5.8 Hz, 1H), 4.47 (lac CH, td, J=9.0, 1.2 Hz, 1H), 4.28 (lac CH, ddd, J=11.4, 9.3, 5.8 Hz, 1H), 3.09 (CH$_2$, br d, J=7.5 Hz, 2H), 2.86 (lac CH, dddd, J=12.6, 8.6, 5.9, 1.2 Hz, 1H), 2.12 (lac CH, dtd, J=12.5, 11.5, 8.8 Hz, 1H), 1.68 (CH$_3$, ddt, J=7.0, 1.9, 0.9 Hz, 3H); $^{13}$C NMR (101 MHz, CDCl$_3$) δ 175.35, 171.58, 129.89, 121.89, 66.06, 49.25, 34.43, 30.50, 12.99; ESI MS: Expected [M+H]$^+$: 184.0974, observed: 184.0978; IR (cm$^{-1}$) 3305, 2943, 1773, 1647, 1542, 1165, 999, 944.

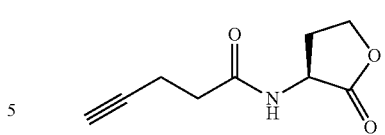

J7:
$^1$H NMR (400 MHz, CDCl$_3$) δ 6.23 (NH, br d, J=5.7 Hz, 1H), 4.57 (lac CH, ddd, J=11.6, 8.5, 5.7 Hz, 1H), 4.48 (lac CH, td, J=9.1, 1.2 Hz, 1H), 4.30 (lac CH, ddd, J=11.4, 9.3, 5.8 Hz, 1H), 2.88 (lac CH, dddd, J=12.7, 8.6, 5.8, 1.2 Hz, 1H), 2.59-2.52 (CH$_2$, m, 2H), 2.52-2.42 (CH$_2$, m, 2H), 2.16 (lac CH, dtd, J=12.5, 11.4, 8.8 Hz, 1H), 2.03 (C≡C—H, t, J=2.5 Hz, 1H); $^{13}$C NMR (101 MHz, CDCl$_3$) δ 175.28, 171.55, 82.51, 69.68, 66.15, 49.43, 34.84, 30.64, 14.67; ESI MS: Expected [M+H]$^+$: 182.0812, observed: 182.0817; IR (cm$^{-1}$): 3339, 3254, 2921, 1783, 1648, 1540, 1178, 1020, 709.

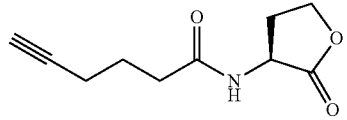

J8:
$^1$H NMR (300 MHz, CDCl$_3$) δ 6.32 (NH, br s, 1H), 4.59 (lac CH, ddd, J=11.6, 8.7, 6.3 Hz, 1H), 4.47 (lac CH, td, J=9.1, 1.3 Hz, 1H), 4.29 (lac CH, ddd, J=11.1, 9.3, 5.9 Hz, 1H), 2.81 (lac CH, dddd, J=12.5, 8.7, 5.9, 1.3 Hz, 1H), 2.41 (CH$_2$, t, J=7.5 Hz, 2H), 2.28 (CH$_2$, td, J=6.9, 2.6 Hz, 2H), 2.17 (lac CH, dtd, J=12.6, 11.4, 8.9 Hz, 1H), 1.99 (C≡C—H, t, J=2.6 Hz, 1H), 1.88 (CH$_2$, p, J=7.1 Hz, 2H); $^{13}$C NMR (75 MHz, CDCl$_3$) δ 175.75, 173.09, 83.51, 77.68, 77.25, 76.83, 69.58, 66.30, 49.40, 34.66, 30.54, 24.10, 18.01; ESI MS: Expected [M+H]$^+$: 196.0969, observed: 196.0966; IR (cm$^{-1}$): 3325, 3279, 2946, 1772, 1646, 1543, 1166, 1013.

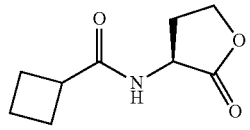 [SMILES: O=C(N[C@H]1CCOC1=O)C1CCC1]

J24:
$^1$H NMR (400 MHz, CDCl$_3$) δ 5.97 (lac CH, br s, 1H), 4.55 (lac CH, ddd, J=11.6, 8.6, 5.9 Hz, 1H), 4.47 (lac CH, td, J=9.1, 1.2 Hz, 1H), 4.29 (lac CH, ddd, J=11.3, 9.3, 5.9 Hz, 1H), 3.07 (CH, pd, J=8.5, 1.0 Hz, 1H), 2.86 (lac CH, dddd, J=12.9, 8.6, 5.8, 1.3 Hz, 1H), 2.38-2.06 (tail CH$_2$+lac CH, m, 5H), 2.06-1.83 (tail CH$_2$, m, 2H); $^{13}$C NMR (101 MHz, CDCl$_3$) δ 175.63, 175.57, 66.12, 49.17, 39.39, 30.68, 25.27, 25.23, 18.15; ESI MS: Expected [M+H]$^+$: 184.0969, observed: 184.0972; IR (cm$^{-1}$): 3307, 2980, 2943, 1777, 1643, 1550, 1172, 1014.

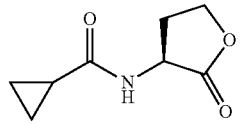 [SMILES: O=C(N[C@H]1CCOC1=O)C1CC1]

J18:

¹H NMR (400 MHz, CDCl₃) δ 6.32 (NH, br s, 1H), 4.60 (lac CH, ddd, J=11.6, 8.6, 5.9 Hz, 1H), 4.52-4.42 (lac CH, m, 1H), 4.29 (lac CH, ddd, J=11.3, 9.3, 5.8 Hz, 1H), 2.84 (lac CH, dddd, J=12.6, 8.6, 5.9, 1.2 Hz, 1H), 2.16 (lac CH, dtd, J=12.5, 11.5, 8.8 Hz, 1H), 1.46 (tail CH, tt, J=7.9, 4.6 Hz, 1H), 1.07-0.94 (tail CH₂, m, 2H), 0.88-0.74 (tail CH₂, m, 2H); ¹³C NMR (101 MHz, CDCl₃) δ 175.74, 174.28, 66.13, 49.43, 30.72, 14.46, 7.85 (2C); ESI MS: Expected [M+H]⁺: 170.0812, observed: 170.0806; IR (cm⁻¹): 3317, 3084, 3012, 2945, 1778, 1641, 1556, 1169.

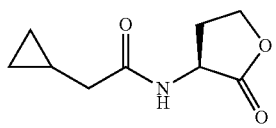 [SMILES: O=C(CC1CC1)N[C@H]1CCOC1=O]

J19:

¹H NMR (400 MHz, CDCl₃) δ 6.52 (NH, br d, J=6.1 Hz, 1H), 4.58 (lac CH, ddd, J=11.6, 8.6, 6.0 Hz, 1H), 4.46 (lac CH, td, J=9.1, 1.2 Hz, 1H), 4.28 (lac CH, ddd, J=11.2, 9.3, 5.9 Hz, 1H 2.84 (dddd, J=12.8, 8.4, 5.9, 1.3 Hz, 1H), 2.27-2.08 (lac CH+tail CH₂, m, 3H), 1.06-0.91 (cyclopropyl CH, m, 1H), 0.69-0.54 (diastereotopic cyclopropyl CH₂, m, 2H), 0.29-0.13 (diastereotopic cyclopropyl CH₂, m, 2H); ¹³C NMR (101 MHz, CDCl₃) δ 175.69, 173.23, 66.22, 49.28, 41.14, 30.65, 7.06, 4.80, 4.75; ESI MS: Expected [M+H]⁺: 184.0969, observed: 184.0962; IR (cm⁻¹): 3315, 2951, 1174, 1648, 1543, 1171, 1015, 999.

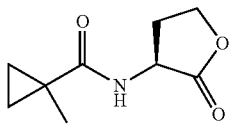

J20:

¹H NMR (400 MHz, CDCl₃) δ 6.31 (NH, br s, 1H), 4.53 (lac CH, ddd, J=11.6, 8.7, 5.7 Hz, 1H), 4.47 (lac CH, td, J=9.2, 1.3 Hz, 1H), 4.28 (lac CH, ddd, J=11.2, 9.3, 5.9 Hz, 1H), 2.83 (lac CH, dddd, J=12.9, 8.6, 6.1, 1.3 Hz, 1H), 2.14 (lac CH, dtd, J=12.5, 11.4, 8.8 Hz, 1H), 1.36 (tail CH₃, S, 3H), 1.29-1.15 (diastereotopic cyclopropyl CH₂, m, 2H), 0.69-0.59 (diastereotopic CH₂, m, 2H); ¹³C NMR (101 MHz, CDCl₃) δ 175.79, 175.73, 66.13, 49.61, 30.64, 19.38, 18.98, 16.69, 16.64; ESI MS: Expected [M+H]⁺: 184.0969, observed: 184.0967; IR (cm⁻¹): 3299, 2918, 1764, 1636, 1524, 1170, 1022, 938

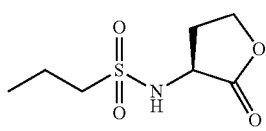

RN6:

¹H NMR (300 MHz, CDCl₃) δ 5.16 (d, J=7.0 Hz, 1H), 4.43 (t, J=9.0 Hz, 1H), 4.38-4.18 (m, 2H), 3.16 (dd, J=9.1, 6.6 Hz, 2H), 2.82-2.61 (m, 1H), 2.28 (qd, J=11.9, 9.1 Hz, 1H), 1.88 (dtt, J=14.1, 6.7, 3.3 Hz, 2H), 1.06 (t, J=7.4 Hz, 3H); ¹³C NMR (126 MHz, CDCl₃) δ 174.6, 65.8, 56.2, 52.3, 31.6, 17.7, 13.0; Expected [M+H]⁺: 225.0904, observed: 225.0901; IR (cm⁻¹): 3248, 2970, 1767, 1318, 1187, 1139, 999, 767

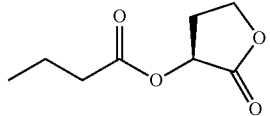

RN7:

¹H NMR (400 MHz, CDCl₃) δ 5.44 (dd, J=9.5, 8.8 Hz, 1H), 4.48 (td, J=9.1, 2.5 Hz, 1H), 4.32 (td, J=9.6, 6.5 Hz, 1H), 2.72 (dddd, J=12.9, 8.8, 6.5, 2.5 Hz, 1H), 2.47-2.24 (m, 3H), 1.69 (h, J=7.4 Hz, 2H), 0.98 (t, J=7.4 Hz, 3H); ¹³C NMR (126 MHz, CDCl₃) δ 172.9, 172.7, 67.5, 65.1, 35.8, 29.1, 18.4, 13.7; Expected [M+H]⁺: 173.0808, observed: 173.0808; IR (cm⁻¹): 2967, 1786, 1740, 1381, 1161, 1102, 1011

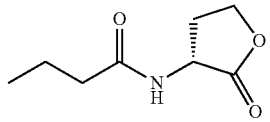

RN5:

¹H NMR (400 MHz, CDCl₃) δ 5.93 (s, 1H), 4.54 (ddd, J=11.7, 8.6, 5.7 Hz, 1H), 4.47 (t, J=8.9 Hz, 1H), 4.29 (ddd, J=11.3, 9.3, 5.8 Hz, 1H), 2.99-2.78 (m, 1H), 2.24 (td, J=7.3, 1.3 Hz, 2H), 2.20-2.03 (m, 1H), 1.69 (h, J=7.4 Hz, 2H), 0.97 (t, J=7.4 Hz, 3H); ¹³C NMR (126 MHz, CDCl₃) δ 175.6, 173.7, 66.3, 49.5, 38.2, 30.9, 19.0, 13.8; ESI MS: Expected [M+H]⁺: 172.0968, observed: 172.0967; IR (cm⁻¹): 3308, 2958, 1775, 1643, 1546, 1365, 1170, 1007, 649

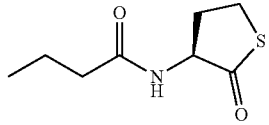

RN8:

¹H NMR (300 MHz, CDCl₃) δ 6.10 (s, 1H), 4.53 (dt, J=13.0, 6.6 Hz, 1H), 3.49-3.14 (m, 2H), 2.89 (dt, J=12.1, 5.9 Hz, 1H), 2.20 (t, J=7.5 Hz, 2H), 2.04-1.78 (m, 1H), 1.65 (h, J=7.5 Hz, 2H), 0.93 (t, J=7.4 Hz, 3H); ¹³C NMR (126 MHz, CDCl₃) δ 205.8, 194.6, 173.6, 173.60, 59.7, 38.44, 32.4, 27.78, 19.1, 13.8;

Expected [M+H]⁺: 188.0740, observed: 188.0739; IR (cm⁻¹): 3264, 2963, 1693, 1641, 1543, 1442, 981, 692

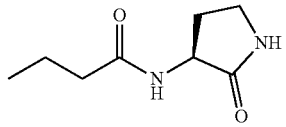

RN9:

To a solution of (3S)-3-amino-2-pyrrolidinone (50 mg, 0.50 mmol, 1 eq) and triethylamine (168 μL, 1 mmol, 2 eq) in acetonitrile (5 mL), butyryl chloride (78 μL, 0.75 mmol, 1.5 eq) was added at room temperature. The solution was allowed to stir for 1 hour at room temperature, after which the solvent was removed under reduced pressure. The remaining solid was purified using flash column chromatography (90/10 DCM/MeOH) to afford product (55.3 mg, 65% yield). ¹H NMR (400 MHz, CDCl₃) δ 6.96 (s, 1H), 6.76-6.33 (m, 1H), 4.37 (ddd, J=10.6, 8.3, 6.1 Hz, 1H), 3.46-3.22 (m, 2H), 2.82-2.58 (m, 1H), 2.26-2.08 (m, 2H), 2.01-1.77 (m, 1H), 1.63 (h, J=7.4 Hz, 2H), 0.91 (t, J=7.4 Hz, 3H); ¹³C NMR (126 MHz, CDCl₃) δ 175.5, 173.9, 50.8, 39.3, 38.4, 30.6, 19.1, 13.9; Expected [M+H]⁺: 171.1128, observed: 171.1127; IR (cm⁻¹): 3273, 2961, 2874, 1687, 1638, 1540, 1291

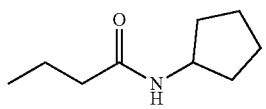

RN4:
¹H NMR (400 MHz, CDCl₃) δ 5.34 (s, 1H), 4.21 (h, J=7.1 Hz, 1H), 2.11 (t, J=7.5 Hz, 2H), 1.99 (dq, J=12.0, 6.5, 6.0 Hz, 2H), 1.70-1.56 (m, 6H), 1.35 (dq, J=13.0, 6.3 Hz, 2H), 0.94 (t, J=7.4 Hz, 3H); ¹³C NMR (126 MHz, CDCl₃) δ 172.6, 51.2, 39.1, 33.4, 23.9, 19.4, 13.9; ESI MS: Expected [M+H]⁺: 156.1383, observed: 156.1382; IR (cm⁻¹): 3295, 2956, 2869, 1636, 1542, 1453, 1218, 695

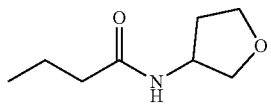

RN2:
To a solution of butyric acid (253 mg, 2.9 mmol) dissolved in 15 mL of water at ambient temperature, was added N-hydroxysuccinimide (330 mg, 2.9 mmol) followed by EDC.HCl (550 mg, 2.9 mmol). The reaction was stirred for 30 min before 3-aminotetrahydrofuran (250 mg, 2.9 mmol) was added. After 24 h, the solution was extracted with chloroform (3×5 mL). The combined chloroform layers were washed with a saturated aqueous solution of sodium bicarbonate (2×5 mL), dried with MgSO₄, filtered and the solvent removed under reduced pressure to afford 22 as a clear oil. Yield: 82.3 mg, 18% yield. ¹H NMR (600 MHz, CDCl₃): δ 5.81 (s, 1H), 4.52-4.46 (m, 1H), 3.88 (ddd, 1H, J=8.0 Hz), 3.77 (dd, 1H, J=5.4, 9.4 Hz), 3.76-3.72 (m, 1H), 3.61 (dd, 1H, J=2.5, 9.4 Hz), 2.26-2.18 (m, 1H), 2.10 (t, 2H, J=7.4 Hz), 1.79-1.71 (m, 1H), 1.61 (sex, 2H, J=7.4 Hz), 0.90 (t, 3H, J=7.4 Hz); ¹³C NMR (150 MHz, CDCl₃): δ 172.7, 73.6, 66.8, 50.1, 38.6, 33.2, 19.1, 13.7; ESI MS: Expected [M+H]⁺: 158.1176, observed: 158.1175; IR (cm⁻¹): 3282, 3068, 2963, 2935, 2873, 1740, 1639, 1540, 1450, 1379, 1286, 1213, 1143, 1063, 908, 802.

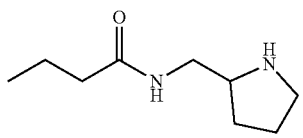

RN11:
To a solution of butyric acid (82 mg, 0.9 mmol) dissolved in 10 mL of water at ambient temperature, was added N-hydroxysuccinimide (106 mg, 0.9 mmol) followed by EDC.HCl (177 mg, 0.9 mmol). The reaction was stirred for 15 min before 1-BOC-2-(aminomethyl)pyrrolidine (185 mg, 0.9 mmol) was added. After 24 h, the solution was then extracted with chloroform (3×5 mL). The combined chloroform layers were washed with a saturated aqueous solution of sodium bicarbonate (3×5 mL), dried with MgSO₄, filtered and the solvent removed to afford the BOC-protected product (an oil). The following BOC deprotection procedure used was adapted from the protocol of Liu et al.⁵⁸ The oil was dissolved in dichloromethane (5 mL) and Amberlyst 15 resin (0.625 g) was added. The mixture was stirred for 24 h, filtered and the resin washed with hexane (5 mL), THF (5 mL) and MeOH (2×5 mL). The resin was then placed in a 4 M ammonia methanolic solution (5 mL) and stirred for 2 hours. Dichloromethane (5 mL) was added to the mixture, which was stirred for an additional 20 h. The resin was then filtered and the solution evaporated under reduced pressure to yield a brown oil. The oil was dissolved in dichloromethane (5 mL) and colored impurities removed using activated charcoal. Filtration and removal of the solvent afforded III as a yellow oil. Yield: 56.9 mg, 36% yield. ¹H NMR (600 MHz, CDCl₃): δ 6.49 (s, 1H), 3.56 (s, 1H), 3.38-3.33 (m, 1H), 3.28-3.22 (m, 1H), 3.08-3.01 (m, 1H), 2.88 (t, 2H), 2.10 (t, 2H), 1.86-1.79 (m, 1H), 1.78-1.71 (m, 1H), 1.70-1.63 (m, 1H), 1.59 (sex, 2H), 1.39-1.31 (m, 1H), 0.87 (t, 3H); ¹³C NMR (150 MHz, CDCl₃): δ 173.5, 58.1, 46.3, 43.1, 38.6, 28.9, 25.6, 19.2, 13.8; ESI MS: Expected [M+H]⁺: 171.1492, observed: 171.1490; IR (cm⁻¹): 3296, 3077, 2961, 2872, 1642, 1548, 1458, 1429, 1363, 1284, 1250, 1209, 1119, 1039, 999, 892

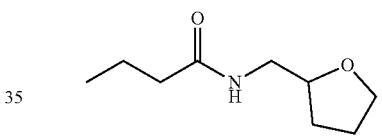

RN10:
To a solution of butyric acid (218 mg, 2.5 mmol) dissolved in 15 mL of water at ambient temperature, was added N-hydroxysuccinimide (285 mg, 2.5 mmol) followed by EDC.HCl (474 mg, 2.5 mmol). The reaction was stirred for 30 min before 2-(aminomethyl)tetrahydrofuran (250 mg, 2.5 mmol) was added. After 48 h, the aqueous solution was extracted with chloroform (4×5 mL). The combined chloroform layers were washed with a saturated aqueous solution of sodium bicarbonate (3×5 mL), dried with MgSO₄, filtered and the solvent removed under reduced pressure to afford I as an oil. Yield: 210.4 mg, 50% yield. ¹H NMR (600 MHz, CDCl₃): δ 5.92 (s, 1H), 3.92-3.86 (m, 1H), 3.82-3.76 (m, 1H), 3.72-3.66 (m, 1H), 3.55-3.49 (m, 1H), 3.10-3.03 (m, 1H), 2.10 (t, 2H, J=7.4 Hz), 1.95-1.87 (m, 1H), 1.86-1.80 (m, 1H), 1.60 (sex, 2H, J=7.4 Hz), 1.52-1.43 (m, 1H), 0.88 (t, 3H, J=7.4 Hz); ¹³C NMR (150 MHz, CDCl₃): δ 173.1, 77.8, 68.0, 43.0, 38.6, 28.6, 25.8, 19.1, 13.7; ESI MS: Expected [M+H]⁺: 172.1332, observed: 172.1331; IR (cm⁻¹): 3297, 2963, 2933, 2873, 1643, 1545, 1459, 1378, 1284, 1252, 1210, 1073, 1026, 922, 821.

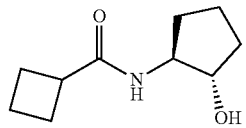 [SMILES: O=C(N[C@H]1CCC[C@@H]1O)C1CCC1]

Precursor to RN12OH:

¹H NMR (400 MHz, CDCl₃) δ 5.71 (s, 1H), 4.80 (s, 1H), 3.91 (q, J=6.7 Hz, 1H), 3.78 (ddt, J=14.3, 8.8, 5.3 Hz, 1H), 3.00 (p, J=8.5 Hz, 1H), 2.26-1.61 (m, 11H), 1.40 (dq, J=12.8, 8.3 Hz, 1H); ¹³C NMR (126 MHz, CDCl₃) δ 177.4, 80.0, 61.1, 39.7, 32.8, 30.7, 25.6, 25.5, 21.5, 18.2; Expected [M+H]⁺: 184.1332, observed: 184.1331; IR (cm⁻¹): 3275, 2941, 2866, 1635, 1548, 1258, 685.

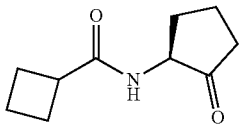 [SMILES: O=C(N[C@H]1CCCC1=O)C1CCC1]

RN12:

¹H NMR (300 MHz, CDCl₃) δ 5.79 (s, 1H), 4.22-3.96 (m, 1H), 3.15-2.90 (m, 1H), 2.76-2.55 (m, 1H), 2.47-1.76 (m, 11H), 1.57 (qd, J=12.3, 6.9 Hz, 1H); ¹³C NMR (101 MHz, CDCl₃) δ 215.6, 175.5, 58.2, 39.7, 35.1, 30.4, 25.5, 25.4, 18.3, 18.2; Expected [M+H]⁺: 182.1176, observed: 182.1176; IR (cm⁻¹): 3250, 2923, 2859, 1742, 1635, 1548, 1270.

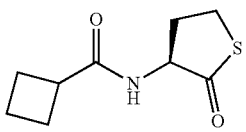 [SMILES: O=C(N[C@H]1CCSC1=O)C1CCC1]

RN15:

¹H NMR (400 MHz, CDCl₃) δ 6.08 (d, 1H), 4.51 (dt, J=13.1, 6.7 Hz, 1H), 3.33 (td, J=11.8, 5.2 Hz, 1H), 3.21 (dd, J=11.1, 6.7 Hz, 1H), 3.04 (p, J=8.5 Hz, 1H), 2.92-2.78 (m, 1H), 2.34-2.06 (m, 4H), 2.00-1.76 (m, 3H); ¹³C NMR (126 MHz, CDCl₃) δ 205.8, 175.6, 59.6, 39.8, 32.4, 27.8, 25.5, 25.5, 18.3; Expected [M+H]⁺: 200.0740, observed: 200.0739; IR (cm⁻¹): 3250, 2975, 2933, 1686, 1637, 1552, 1257, 913.

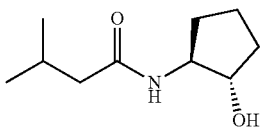

Precursor to RN36OH:

¹H NMR (500 MHz, CDCl₃) δ 5.56 (s, 1H), 4.60 (s, 1H), 3.95 (q, J=6.4 Hz, 1H), 3.89-3.73 (m, 1H), 2.19-1.97 (m, 5H), 1.80 (dtdd, J=12.5, 9.2, 6.4, 2.7 Hz, 1H), 1.75-1.62 (m, 2H), 1.41 (dq, J=12.8, 8.3 Hz, 1H), 0.97 (dd, J=6.3, 6H); ¹³C NMR (126 MHz, CDCl₃) δ 175.0, 80.1, 61.2, 45.8, 32.8, 30.8, 26.4, 22.6, 22.5, 21.6; Expected [M+H]⁺: 186.1489, observed: 186.1487; IR (cm⁻¹): 3286, 3088, 2953, 2925, 2867, 1636, 1551, 1049.

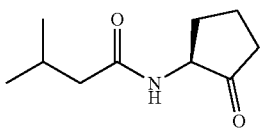

RN36:

¹H NMR (300 MHz, CDCl₃) δ 5.84 (s, 1H), 4.24-3.98 (m, 1H), 2.66 (dddd, J=14.0, 7.9, 3.7, 1.6 Hz, 1H), 2.49-2.34 (m, 1H), 2.27-1.99 (m, 5H), 1.86 (tddd, J=13.0, 10.7, 8.9, 6.1 Hz, 1H), 1.58 (qd, J=12.3, 6.9 Hz, 1H), 0.95 (dd, J=6.5, 3.2 Hz, 5H); ¹³C NMR (126 MHz, CDCl₃) δ 215.4, 173.0, 58.3, 45.8, 35.0, 30.3, 26.3, 22.6, 22.5, 18.2; Expected [M+H]⁺: 184.1332, observed: 184.1331; IR (cm⁻¹): 3256, 3073, 2958, 2869, 17480, 1637, 1550, 1372.

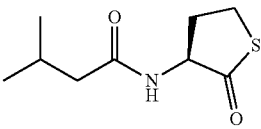

RN37:

¹H NMR (300 MHz, CDCl₃) δ 6.04 (s, 1H), 4.53 (dt, J=12.9, 6.5 Hz, 1H), 3.35 (td, J=11.7, 5.1 Hz, 1H), 3.29-3.16 (m, 1H), 2.99-2.83 (m, 1H), 2.08 (d, J=6.5 Hz, 3H), 1.91 (qd, J=12.4, 7.0 Hz, 1H), 1.00-0.88 (m, 6H); ¹³C NMR (126 MHz, CDCl₃) δ 205.8, 173.1, 59.5, 45.8, 32.2, 27.7, 26.3, 22.6, 22.5; Expected [M+H]⁺: 202.0896, observed: 202.0893; IR (cm⁻¹): 3267, 3071, 2952, 2924, 2866, 1690, 1638, 1548, 917.

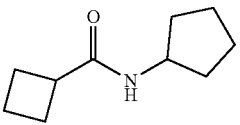 [SMILES: O=C(NC1CCCC1)C1CCC1]

RN13:

¹H NMR (400 MHz, CDCl₃) δ 5.81 (d, 1H), 4.09 (h, J=7.1 Hz, 1H), 2.91 (p, J=8.4 Hz, 1H), 2.18 (pd, J=9.2, 2.3 Hz, 2H), 2.07-1.95 (m, 2H), 1.94-1.68 (m, 4H), 1.66-1.40 (m, 4H), 1.28 (dq, J=14.1, 7.5, 7.0 Hz, 2H); ¹³C NMR (126 MHz, CDCl₃) δ 174.6, 51.1, 40.2, 33.4, 25.5, 23.9, 18.2; Expected [M+H]⁺: 168.1383, observed: 168.1381; IR (cm⁻¹): 3290, 2946, 2865, 1636, 1545, 1257, 678.

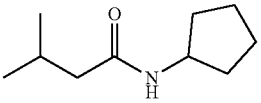

RN39:

¹H NMR (500 MHz, CDCl₃) δ 5.31 (d, J=10.9 Hz, 1H), 4.22 (h, J=7.0 Hz, 1H), 2.10 (dp, J=13.2, 6.6 Hz, 1H), 2.03-1.94 (m, 4H), 1.71-1.54 (m, 4H), 1.42-1.28 (m, 2H), 0.94 (d, J=6.6 Hz, 6H); ¹³C NMR (126 MHz, CDCl₃) δ 172.1, 51.2, 46.5, 33.4, 26.4, 23.8, 22.6; Expected [M+H]⁺: 170.1539, observed: 170.1537; IR (cm⁻¹): 297, 3073, 2954, 2868, 1633, 1541.

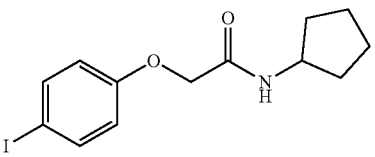 [SMILES: O=C(COc1ccc(I)cc1)NC1CCCC1]

RN17:

$^1$H NMR (400 MHz, CDCl$_3$) δ 7.59 (d, J=8.7 Hz, 2H), 6.70 (d, J=8.7 Hz, 2H), 6.39 (s, 1H), 4.42 (s, 2H), 4.29 (h, J=7.0 Hz, 1H), 2.01 (dd, J=12.4, 5.7 Hz, 2H), 1.66 (dt, J=19.4, 7.9 Hz, 4H), 1.41 (dd, J=12.6, 6.3 Hz, 2H); $^{13}$C NMR (101 MHz, CDCl$_3$) δ 167.2, 157.2, 138.7, 117.1, 84.6, 67.6, 50.9, 33.1, 23.8; Expected [M+H]$^+$: 346.0299, observed: 346.0290; IR (cm−1): 3271, 2925, 2865, 1647, 1553, 1482, 1453, 1234, 843.

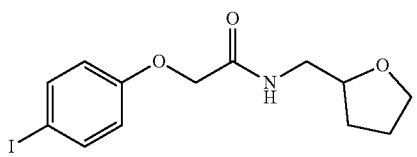 [SMILES: O=C(COc1ccc(I)cc1)NCC1CCCO1]

RN23:

$^1$H NMR (500 MHz, CDCl$_3$) δ 7.60-7.53 (m, 2H), 6.88-6.77 (m, 1H), 6.75-6.66 (m, 2H), 4.46 (s, 2H), 3.98 (qd, J=7.1, 3.4 Hz, 1H), 3.86-3.69 (m, 2H), 3.61 (ddd, J=13.8, 6.4, 3.4 Hz, 1H), 3.32-3.21 (m, 1H), 2.01-1.90 (m, 1H), 1.86 (dq, J=14.0, 6.9, 6.4 Hz, 2H), 1.51 (dq, J=12.1, 7.6 Hz, 1H); $^{13}$C NMR (126 MHz, CDCl$_3$) δ 167.9, 157.2, 138.7, 117.1, 84.5, 77.6, 68.4, 67.5, 42.7, 28.7, 26.0; Expected [M+H]$^+$: 362.0248, 362.0241; IR (cm$^{-1}$): 3277, 2969, 2924, 2864, 1655, 1547, 1481, 1240, 1058.

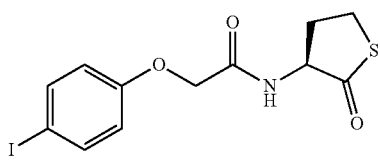 [SMILES: O=C(COc1ccc(I)cc1)N[C@H]1CCSC1=O]

RN22:

$^1$H NMR (500 MHz, CDCl$_3$) δ 7.70-7.48 (m, 2H), 6.94 (d, J=7.6 Hz, 1H), 6.77-6.68 (m, 2H), 4.61 (dt, J=13.2, 6.7 Hz, 1H), 4.50 (d, J=2.6 Hz, 2H), 3.39 (td, J=11.8, 5.1 Hz, 1H), 3.32-3.27 (m, 1H), 3.02-2.88 (m, 1H), 2.01 (qd, J=12.4, 7.0 Hz, 1H); $^{13}$C NMR (126 MHz, CDCl$_3$) δ 204.7, 168.4, 157.0, 138.8, 117.2, 84.9, 67.4, 59.1, 31.8, 27.7; Expected [M+H]: 377.9655, observed: 377.9650; IR (cm$^{-1}$): 3282, 2974, 2926, 2858, 1696, 1655, 1536, 1233.

REFERENCES (1) Camilli, A.; Bassler, B. L., *Science* 2006, 311, 1113-1116.
(2) Williams, P.; Winzer, K.; Chan, W. C.; Camara, M., *Philos. Trans. R. Soc., B* 2007, 362, 1119-1134.
(3) Fuqua, C.; Greenberg, E. P., *Nat. Rev. Mol. Cell Biol.* 2002, 3, 685-695.
(4) Pearson, J. P.; Van Delden, C.; Iglewski, B. H., *J. Bacteriol.* 1999, 181, 1203-1210.
(5) Rutherford, S. T.; Bassler, B. L., *Cold Spring Harb Perspect Med* 2012, 2.
(6) Estrela, A. i. B.; Heck, M. G.; Abraham, W.-R., *Curr. Med. Chem.* 2009, 16, 1512-1530.
(7) Hentzer, M.; Givskov, M., *J. Clin. Invest.* 2003, 112, 1300-1307.
(8) Palumbi, S. R., *Science* 2001, 293, 1786-1790.
(9) O'Connell, K. M.; Hodgkinson, J. T.; Sore, H. F.; Welch, M.; Salmond, G. P.; Spring, D. R., *Angew. Chem., Int. Ed.* 2013, 52, 10706-10733.
(10) Clatworthy, A. E.; Pierson, E.; Hung, D. T., *Nat. Chem. Biol.* 2007, 3, 541-548.
(11) Sully, E. K.; Malachowa, N.; Elmore, B. O.; Alexander, S. M.; Femling, J. K.; Gray, B. M.; DeLeo, F. R.; Otto, M.; Cheung, A. L.; Edwards, B. S.; Sklar, L. A.; Horswill, A. R.; Hall, P. R.; Gresham, H. D., *PLoS Pathog.* 2014, 10, e1004174.
(12) Gerdt, J. P.; Blackwell, H. E., *ACS Chem. Biol.* 2014, 9, 2291-2299.
(13) Mellbye, B.; Schuster, M., *mBio* 2011, 2, e00131-11.
(14) O'Connor, C. J.; Laraia, L.; Spring, D. R., *Chem. Soc. Rev.* 2011, 40, 4332-4345.
(15) Praneenararat, T.; Palmer, A. G.; Blackwell, H. E., *Org. Biomol. Chem.* 2012, 10, 8189-8199.
(16) Kerr, K. G.; Snelling, A. M., *J. Hosp. Infect.* 2009, 73, 338-344.
(17) Folkesson, A.; Jelsbak, L.; Yang, L.; Johansen, H. K.; Ciofu, O.; Hoiby, N.; Molin, S., *Nat. Rev. Microbiol.* 2012, 10, 841-851.
(18) Mesaros, N.; Nordmann, P.; Plesiat, P.; Roussel-Delvallez, M.; Van Eldere, J.; Glupczynski, Y.; Van Laethem, Y.; Jacobs, F.; Lebecque, P.; Malfroot, A.; Tulkens, P. M.; Van Bambeke, F., *Clin. Microbiol. Infect.* 2007, 13, 560-578.
(19) D'Agata, E., *Pseudomonas aeruginosa* and Other *Pseudomonas* Species. In *Mandell, Douglas, and Bennett's Principles and Practice of Infectious Diseases*, 8th ed.; Bennett, J. E.; Dolin, R.; Blaser, M. J., Eds. Saunders: Philadelphia, Pa., 2015; Vol. 221, pp 2518-2531.e3.
(20) Lister, P. D.; Wolter, D. J.; Hanson, N. D., *Clin. Microbiol. Rev.* 2009, 22, 582-610.
(21) Schuster, M.; Greenberg, E. P., *Int. J. Med. Microbiol.* 2006, 296, 73-81.
(22) Gambello, M. J.; Kaye, S.; Iglewski, B. H., *Infect. Immun.* 1993, 61, 1180-1184.
(23) Brint, J. M.; Ohman, D. E., *J. Bacteriol.* 1995, 177, 7155-7163.
(24) Rumbaugh, K. P.; Griswold, J. A.; Iglewski, B. H.; Hamood, A. N., *Infect. Immun.* 1999, 67, 5854-5862.
(25) Pearson, J. P.; Feldman, M.; Iglewski, B. H.; Prince, A., *Infect. Immun.* 2000, 68, 4331-4334.
(26) Wu, H.; Song, Z.; Givskov, M.; Doring, G.; Worlitzsch, D.; Mathee, K.; Rygaard, J.; Hoiby, N., *Microbiology* 2001, 147, 1105-1113.
(27) Venturi, V., *FEMS Microbiol. Rev.* 2006, 30, 274-291.
(28) Smith, R., *Curr. Opin. Microbiol.* 2003, 6, 56-60.
(29) Schuster, M.; Lostroh, C. P.; Ogi, T.; Greenberg, E. P., *J. Bacteriol.* 2003, 185, 2066-2079.
(30) Wagner, V. E.; Bushnell, D.; Passador, L.; Brooks, A. I.; Iglewski, B. H., *J. Bacteriol.* 2003, 185, 2080-2095.
(31) Geske, G. D.; O'Neill, J. C.; Blackwell, H. E., *Chem. Soc. Rev.* 2008, 37, 1432-1447.
(32) Galloway, W.; Hodgkinson, J. T.; Bowden, S. D.; Welch, M.; Spring, D. R., *Chem. Rev.* 2011, 111, 28-67.
(33) Van Delden, C.; Pesci, E. C.; Pearson, J. P.; Iglewski, B. H., *Infect. Immun.* 1998, 66, 4499-4502.
(34) Dekimpe, V.; Déziel, E., *Microbiology* 2009, 155, 712-723.
(35) Bjarnsholt, T.; Jensen, P. O.; Jakobsen, T. H.; Phipps, R.; Nielsen, A. K.; Rybtke, M. T.; Tolker-Nielsen, T.; Givskov, M.; Hoiby, N.; Ciofu, O., *PLoS ONE* 2010, 5, e10115.
(36) Lee, J.; Wu, J.; Deng, Y.; Wang, J.; Wang, C.; Chang, C.; Dong, Y.; Williams, P.; Zhang, L. H., *Nat. Chem. Biol.* 2013, 9, 339-343.

(37) O'Loughlin, C. T.; Miller, L. C.; Siryaporn, A.; Drescher, K.; Semmelhack, M. F.; Bassler, B. L., *Proc. Natl. Acad. Sci. U.S.A.* 2013, 110, 17981-17986.
(38) Welsh, M. A.; Eibergen, N. R.; Moore, J. D.; Blackwell, H. E., *J. Am. Chem. Soc.* 2015, 137, 1510-1519.
(39) Morkunas, B.; Galloway, W. R.; Wright, M.; Ibbeson, B. M.; Hodgkinson, J. T.; O'Connell, K. M.; Bartolucci, N.; Della Valle, M.; Welch, M.; Spring, D. R., *Org. Biomol. Chem.* 2012, 10, 8452-8464.
(40) Kenakin, T., *ACS Chem. Biol.* 2009, 4, 249-260.
(41) Kent, A. D.; Triplett, E. W., *Annu. Rev. Microbiol.* 2002, 56, 211-236.
(42) Prinz, H., *J. Chem. Biol.* 2010, 3, 37-44.
(43) Geske, G. D.; O'Neill, J. C.; Miller, D. M.; Mattmann, M. E.; Blackwell, H. E., *J. Am. Chem. Soc.* 2007, 129, 13613-13625.
(44) Geske, G. D.; Mattmann, M. E.; Blackwell, H. E., *Bioorg. Med. Chem. Lett.* 2008, 18, 5978-5981.
(45) Mattmann, M. E.; Shipway, P. M.; Heth, N. J.; Blackwell, H. E., *ChemBioChem* 2011, 12, 942-949.
(46) Moore, J. D.; Gerdt, J. P.; Eibergen, N. R.; Blackwell, H. E., *ChemBioChem* 2014, 15, 435-442.
(47) Galloway, W. R.; Hodgkinson, J. T.; Bowden, S.; Welch, M.; Spring, D. R., *Trends Microbiol.* 2012, 20, 449-458.
(48) Chen, G.; Swem, L. R.; Swem, D. L.; Stauff, D. L.; O'Loughlin, C. T.; Jeffrey, P. D.; Bassler, B. L.; Hughson, F. M., *Mol. Cell* 2011, 42, 199-209.
(49) Grant D. Geske, Jennifer C. O'Neill, and Helen E. Blackwell (2007) N-Phenylacetanoyl-L-Homoserine Lactones Can Strongly Antagonize or Superagonize Quorum Sensing in *Vibrio fischeri*," ACS Chem. Biol. 2(5), 315-320.
(50) Grant D. Geske, Jennifer C. O'Neill, David M. Miller, Rachel J. Wezeman, Margrith E. Mattmann, Qi Lin, and Helen E. Blackwell (2008) "Comparative Analyses of N-Acylated Homoserine Lactones Reveal Unique Structural Features that Dictate Their Ability to Activate or Inhibit Quorum Sensing," ChemBioChem 9:389-400.
(51) Eibergen, N. A., et al. (2015) "Potent and Selective Modulation of the RhlR Quorum Sensing Receptor by Using Non-native Ligands: An Emerging Target for Virulence Control in *Pseudomonas aeruginosa*," Chem BioChem, 16, 2348-2356.
(52) Moore, J. D.; Rossi, F. M.; Welsh, M. A.; Nyffeler, K. E.; Blackwell, H. E. *J. Am Chem Soc* 2015, 137, 14626.
(53) O'Reilly, M. C.; Blackwell, H. E. *ACS Infectious Diseases* 2016, 2, 32.
(54) Förster-Fromme, K.; Jendrossek, D. *FEMS Microbiology Letters* 2008, 286, 78.
(55) Published PCT application WO2003106445 A1. (Nielsen and Givakov)
(56) Jog, G. J.; Igarashi, J.; Suga, H. Chemistry and Biology 2006, 13, 123.
(57) Skowronek, P.; Gawronski, J. Tetrahedron: Asymmetry 1999, 10, 4585.
(58) Liu et al. (1998) J. Org. Chem. 63:3471-3473.
(59) Yates, E. A.; Philipp, B.; Buckley, C.; Atkinson, S.; Chhabra, S. R.; Sockett, R. E.; Goldner, M.; Dessaux, Y.; Camara, M.; Smith, H.; Williams, P. Infect. Immun. 2002, 70, 5635.
(60) Igarashi, J.; Suga, H. In Quorum Sensing: Methods and Protocols; Rumbaugh, K. P., Ed. 2011; Vol. 692, p 265.
(61) Lao, W.; Kjelleberg, S.; Kumar, N.; deNys, R.; Read, R. W.; Steinberg, P. Magn. Reson. Chem. 1999, 37, 157.
(62) Lindemann, A.; Pessi, G.; Schaefer, A. L.; Mattmann, M. E.; Christensen, Q. H.; Kessler, A.; Hennecke, H.; Blackwell, H. E.; Greenberg, E. P.; Harwood, C. S. Proc. Natl. Acad. Sci. U.S.A. 2011, 108, 16765.
(63) Kim, C.; Kim, J.; Park, H.-Y.; Mclean, R. J. C.; Kim, C. K.; Jeon, J.; Yi, S.-S.; Kim, Y. G.; Lee, Y.-S.; Yoon, J. J. Microbiol. Biotechnol. 2007, 17, 1598.
(64) Stacy, D. M.; Le Quement, S. T.; Hansen, C. L.; Clausen, J. W.; Tolker-Nielsen, T.; Brummond, J. W.; Givskov, M.; Nielsen, T. E.; Blackwell, H. E. Org. Biomol. Chem. 2013, 11, 938.
(65) Zhu, J.; Beaber, J. W.; More, M. I.; Fuqua, C.; Eberhard, A.; Winans, S. C. J. Bacteriol. 1998, 180, 5398.
(66) Petersen, M.; Kalbermatten, G. 2001, WO2001018231 A2.
(67) Ikeda, T.; Kajiyama, K.; Kita, T.; Takiguchi, N.; Kuroda, A.; Kato, J.; Ohtake, H. Chemistry Letters 2001, 314.
(68) Mcclean, K. H.; Winson, M. K.; Fish, L.; Taylor, A.; Chhabra, S. R.; Camara, M.; Daykin, M.; John, H.; Swift, S.; Bycroft, B. W.; Stewart, G. S. a. B.; Williams, P. Microbiology 1997, 143, 3703.
(69) Ishida, T.; Ikeda, T.; Takiguchi, N.; Kuroda, A.; Ohtake, H.; Kato, J. Applied and Environmental Microbiology 2007, 73, 3183.
(70) Zirvi, K. A.; Jarboe, C. H. J. Chem. Soc. B 1971, 1603.
(71) McInnis, C. E.; Blackwell, H. E. *Bioorganic & medicinal chemistry* 2011, 19, 4820.
(72) Boursier, M. E.; Moore, J. D.; Heitman, K. M.; Shepardson-Fungairino, S. P.; Combs, J. B.; Koenig, L. C.; Shin, D.; Brown, E. C.; Nagarajan, N.; Blackwell, H. E. (2018) ACS Chem. Biol. 13(9):2655-2662.

The invention claimed is:
1. A compound of formula:

A-W-HG where:
—W— is —CO—NH—, —SO$_2$—NH—, —CO—NH—CH$_2$—, or —SO$_2$—NH—CH$_2$—;
A is selected from cyclobutyl, and —CH$_2$—cyclopropyll and
HG is selected from the group of moieties of formula:

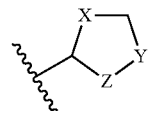

where:
X is CH$_2$
Y is O or S and
Z is C=O or CH(OH).
2. The compound of claim 1, wherein X=CH$_2$, Y=O and Z=CO or CH(OH).
3. The compound of claim 1 which is:

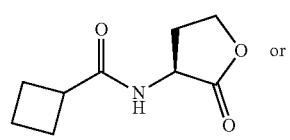

-continued

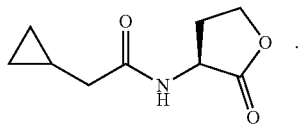
J25

4. The compound of claim 1 which is:

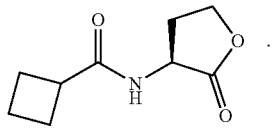
J24

5. The compound of claim 2, wherein W is —CO—NH—.
6. The compound of claim 1, wherein W is —CO—NH—.
7. The compound of claim 1, wherein HG is:

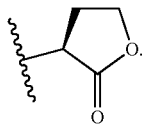

8. The compound of claim 7, wherein A is cyclopropyl, cyclobutyl, or CH₂ cyclopropy.
9. The compound of claim 8, wherein W is —CO—NH—.
10. A compound of formula:

A-W-HG where:
—W— is —CO—NH—, —SO₂—NH—, —CO—NH—CH₂—, or —SO₂—NH—CH₂—;

A is selected from cyclopropyl, cyclobutyl, and —CH₂—cyclopropyl; and
HG is selected from the group of moieties of formula:

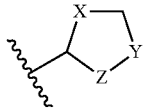

where:
X is CH₂
Y is S; and
Z is C=O or CH(OH).

11. The compound of claim 10, wherein X=CH₂; Y=S; and Z=CO.
12. The compound of claim 10, wherein A is cyclobutyl or —CH₂—cyclopropyl.
13. The compound of claim 11, wherein W is —CO—NH—.
14. The compound of claim 10, wherein W is —CO—NH—.
15. A method for modulating RhlR of a Gram-negative bacterium which comprises contacting the bacterium with one or more compounds of claim 1.
16. A method of treating an infection of a Gram-negative bacterium by administering to an individual in need of treatment a therapeutically effective amount of a compound of claim 1.
17. A method of treating an infection of a Gram-negative bacterium by administering to an individual in need of treatment a therapeutically effective amount of a compound of claim 10.
18. A method for modulating RhlR of a Gram-negative bacterium which comprises contacting the bacterium with one or more compounds of claim 10.

* * * * *

UNITED STATES PATENT AND TRADEMARK OFFICE
CERTIFICATE OF CORRECTION

PATENT NO. : 11,247,976 B2
APPLICATION NO. : 16/097541
DATED : February 15, 2022
INVENTOR(S) : Helen Blackwell et al.

It is certified that error appears in the above-identified patent and that said Letters Patent is hereby corrected as shown below:

In the Claims

Column 64, Claim 1, Line 41, replace "and -$CH_2$-cyclopropyll" with --and -$CH_2$-cyclopropyl;--.

Column 64, Claim 1, Line 53, replace "X is $CH_2$°" with --X is $CH_2$;--.

Column 64, Claim 1, Line 54, replace "Y is O or S and" with --Y is O or S; and--.

Column 65, Claim 8, Lines 30-31, replace "The compound of claim 7, wherein A is cyclopropyl, cyclobutyl, or $CH_2$ cyclopropy" with --The compound of claim 7, wherein A is cyclobutyl--.

Column 66, Claim 10, Line 12, replace "X is $CH_2$" with --X is $CH_2$;--.

Signed and Sealed this
Tenth Day of May, 2022

Katherine Kelly Vidal
*Director of the United States Patent and Trademark Office*